(12) United States Patent
Spector et al.

(10) Patent No.: US 9,376,474 B1
(45) Date of Patent: *Jun. 28, 2016

(54) **CHROMATOGRAPHY MATRICES INCLUDING NOVEL *STAPHYLOCOCCUS AUREUS* PROTEIN A BASED LIGANDS**

(71) Applicant: EMD Millipore Corporation, Billerica, MA (US)

(72) Inventors: Shari Spector, Lexington, MA (US); Robert Smith, Stow, MA (US); Joe Orlando, Waltham, MA (US); Nanying Bian, Lexington, MA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/970,610

(22) Filed: Dec. 16, 2015

Related U.S. Application Data

(63) Continuation of application No. 14/683,738, filed on Apr. 10, 2015, now Pat. No. 9,234,010, which is a continuation of application No. 14/534,999, filed on Nov. 6, 2014, now Pat. No. 9,018,305, which is a continuation of application No. 14/298,332, filed on Jun. 6, 2014, now Pat. No. 8,895,706, which is a continuation of application No. 13/489,999, filed on Jun. 6, 2012, now Pat. No. 8,754,196.

(60) Provisional application No. 61/494,701, filed on Jun. 8, 2011.

(51) Int. Cl.
  *C07K 14/31* (2006.01)
  *C07K 1/22* (2006.01)
  *C07K 16/12* (2006.01)

(52) U.S. Cl.
  CPC . *C07K 14/31* (2013.01); *C07K 1/22* (2013.01); *C07K 16/1271* (2013.01)

(58) Field of Classification Search
  None
  See application file for complete search history.

(56) References Cited

U.S. PATENT DOCUMENTS

| | | |
|---|---|---|
| 4,617,266 A | 10/1986 | Fahnestock |
| 4,879,378 A | 11/1989 | Foster et al. |
| 5,084,559 A | 1/1992 | Profy |
| 5,143,844 A | 9/1992 | Abrahmsen et al. |
| 5,151,350 A | 9/1992 | Colbert et al. |
| 5,198,531 A | 3/1993 | Webber et al. |
| 5,240,680 A | 8/1993 | Zuckermann et al. |
| 5,260,373 A | 11/1993 | Profy et al. |
| 5,580,757 A | 12/1996 | Desnick et al. |
| 6,013,763 A | 1/2000 | Braisted et al. |
| 6,060,596 A | 5/2000 | Lerner et al. |
| 6,197,927 B1 | 3/2001 | Braisted et al. |
| 6,399,750 B1 | 6/2002 | Johansson |
| 6,602,977 B1 | 8/2003 | Ljungqvist et al. |
| 6,831,161 B1 | 12/2004 | Uhlen et al. |
| 7,026,446 B1 | 4/2006 | Atwell et al. |
| 7,083,948 B1 | 8/2006 | Sassenfeld et al. |
| 7,163,686 B1 | 1/2007 | Silverman |
| 7,192,738 B2 | 3/2007 | Lowman et al. |
| 7,311,918 B2 | 12/2007 | Choi et al. |
| 7,691,608 B2 | 4/2010 | Peyser |
| 7,709,209 B2 | 5/2010 | Hober et al. |
| 7,833,723 B2 | 11/2010 | Bian et al. |
| 7,834,158 B2 | 11/2010 | Hober |
| 7,846,682 B2 | 12/2010 | Bian et al. |
| 7,847,071 B2 | 12/2010 | Bonnerjea et al. |
| 8,329,860 B2 | 12/2012 | Hall et al. |
| 8,754,196 B2 | 6/2014 | Spector et al. |
| 2003/0059910 A1 | 3/2003 | Moloney et al. |
| 2005/0100970 A1 | 5/2005 | Uhlen et al. |
| 2005/0143566 A1 | 6/2005 | Hober |
| 2005/0171339 A1 | 8/2005 | Sugo et al. |
| 2006/0030696 A1 | 2/2006 | Bonnerjea et al. |
| 2006/0134805 A1 | 6/2006 | Berg et al. |
| 2006/0194950 A1 | 8/2006 | Hober et al. |
| 2006/0194955 A1 | 8/2006 | Hober et al. |
| 2006/0205016 A1 | 9/2006 | Silverman |
| 2007/0207500 A1 | 9/2007 | Bian et al. |
| 2008/0096819 A1 | 4/2008 | Grabstein et al. |
| 2008/0108053 A1 | 5/2008 | Patchornik |
| 2008/0210615 A1 | 9/2008 | Joehnck et al. |
| 2008/0255027 A1 | 10/2008 | Moya et al. |
| 2009/0093017 A1 | 4/2009 | Peyser |
| 2009/0246885 A1 | 10/2009 | Bian et al. |
| 2009/0299035 A1 | 12/2009 | Iwakura et al. |
| 2009/0317381 A1 | 12/2009 | Plaut et al. |
| 2010/0022760 A1 | 1/2010 | Hober et al. |

(Continued)

FOREIGN PATENT DOCUMENTS

| | | |
|---|---|---|
| CN | 1642976 A | 7/2005 |
| CN | 101522278 A | 9/2009 |

(Continued)

OTHER PUBLICATIONS

"MabSelect SuRe—Studies on Ligand Toxicity, Leakage, Removal of Leached Ligand, and Sanitization", 11-0011-64 AA, Nov. 2004, Amersham Application Note, Process-scale antibody purification, Amersham Biosciences, pp. 1-6.

(Continued)

*Primary Examiner* — Suzanne M Noakes
(74) *Attorney, Agent, or Firm* — EMD Millipore Corporation

(57) ABSTRACT

The present invention relates to chromatography matrices including ligands based on one or more domains of immunoglobulin-binding proteins such as, *Staphylococcus aureus* Protein A (SpA), as well as methods of using the same.

15 Claims, 9 Drawing Sheets

(56) References Cited

U.S. PATENT DOCUMENTS

| | | | |
|---|---|---|---|
| 2010/0048876 | A1 | 2/2010 | Hall et al. |
| 2010/0063256 | A1 | 3/2010 | Spector |
| 2010/0130721 | A1 | 5/2010 | Iwakura et al. |
| 2010/0168395 | A1 | 7/2010 | Sato |
| 2010/0221844 | A1 | 9/2010 | Bian et al. |
| 2010/0286373 | A1 | 11/2010 | Majima et al. |
| 2012/0149875 | A1 | 6/2012 | Johansson et al. |

FOREIGN PATENT DOCUMENTS

| | | | |
|---|---|---|---|
| CN | 101704879 | A | 5/2010 |
| CN | 101775069 | A | 7/2010 |
| EP | 0230869 | A2 | 8/1987 |
| EP | 0550771 | A1 | 7/1993 |
| EP | 1564286 | A1 | 8/2005 |
| EP | 1123389 | B1 | 10/2005 |
| EP | 1601697 | B1 | 5/2007 |
| EP | 1972689 | A2 | 9/2008 |
| EP | 1992692 | A1 | 11/2008 |
| EP | 2014359 | A1 | 1/2009 |
| EP | 2066419 | A1 | 6/2009 |
| EP | 2157099 | A1 | 2/2010 |
| EP | 2202310 | A2 | 6/2010 |
| JP | 2005-538693 | A | 12/2005 |
| JP | 2006-304633 | A | 11/2006 |
| JP | 2007-525412 | A | 9/2007 |
| JP | 2007-537700 | A | 12/2007 |
| JP | 2009-071766 | A | 4/2009 |
| JP | 5480558 | B2 | 4/2014 |
| WO | 84/00773 | A1 | 3/1984 |
| WO | 90/02182 | A1 | 3/1990 |
| WO | 90/09237 | A1 | 8/1990 |
| WO | 95/19374 | A1 | 7/1995 |
| WO | 97/17361 | A1 | 5/1997 |
| WO | 97/36614 | A1 | 10/1997 |
| WO | 00/23580 | A1 | 4/2000 |
| WO | 00/63243 | A1 | 10/2000 |
| WO | 00/69457 | A1 | 11/2000 |
| WO | 03/080655 | A1 | 10/2003 |
| WO | 2005/003156 | A1 | 1/2005 |
| WO | 2006/004067 | A1 | 1/2006 |
| WO | 2006/070416 | A1 | 7/2006 |
| WO | 2006/092338 | A2 | 9/2006 |
| WO | 2007/019376 | A2 | 2/2007 |
| WO | 2007/138328 | A2 | 12/2007 |
| WO | 2008/039141 | A1 | 4/2008 |
| WO | 2008/091740 | A2 | 7/2008 |
| WO | 2008/127457 | A2 | 10/2008 |
| WO | 2009/138484 | A2 | 11/2009 |
| WO | 2009/146755 | A1 | 12/2009 |
| WO | 2010/080065 | A1 | 7/2010 |
| WO | 2010/110288 | A1 | 9/2010 |
| WO | 2012/074463 | A1 | 6/2012 |
| WO | 2012/087230 | A1 | 6/2012 |

OTHER PUBLICATIONS

"Peptide Metabolism in Cytoplasm of Brain Cells", 665th Meeting, University of Southampton, 1 page.

Extended European Search Report and Search Opinion received for EP Patent Application No. 012171045.3, mailed on Mar. 5, 2013, 19 pages.

Partial European Search Report received for EP Patent Application No. 012171045.3, mailed on Sep. 24, 2012, 8 pages.

Extended European Search Report received for EP Patent Application No. 09167670.0, mailed on Dec. 30, 2009, 7 pages.

Extended European Search Report received for EP Patent Application No. 09180615.8, mailed on Sep. 16, 2010, 18 pages.

Notice of Opposition received in European Patent Application No. 09180615.8 on Dec. 19, 2013, 24 pages.

Observation filed for the European application No. 09180615.8 on Jun. 3, 2014, 17 pages.

Partial European Search Report received for EP Patent Application No. 09180615.8, mailed on May 20, 2010, 8 pages.

Extended European Search Report and European Search Opinion received for European Patent Application No. 12163614.6, mailed on Aug. 8, 2012, 8 pages.

Extended European Search Report and European Search Opinion received for European Patent Application No. 12163615.3, mailed on Aug. 8, 2012, 8 pages.

Extended European Search Report and European Search Opinion received for European Patent Application No. 12171108.9, mailed on Oct. 2, 2012, 16 pages.

Extended European Search Report and European Search Opinion received for European Patent Application No. 14163423.8, mailed on Oct. 7, 2014, 10 pages.

Unpublished Japanese Patent Application No. 2009-71766, filed on Mar. 24, 2009, Yoshida et al., titled "Protein having Affinity for Immunoglobulin, and Immunoglobulin-Binding Affinity Ligand" (Corresponds to U.S 20120208234 A1).

Altschul et al., "Basic Local Alignment Search Tool", Journal of Molecular Biology, vol. 215, 1990, pp. 403-410.

Amersham Biosciences, "rmp Protein A Sepharose Fast flow", Data File, Affinity Chromatography, 2000, pp. 1-4.

Arshady, "Styrene Based Polymer Supports Developed by Suspension Polymerization", Chimica e L'Industria, vol. 70, No. 9, 1988, pp. 70-75.

Atkins et al., "S. Aureus IgG-Binding Proteins SpA and Sbi: Host Specificity and Mechanisms of Immune Complex Formation", Molecular Immunology, vol. 45, 2008, pp. 1600-1611.

Ausubel et al. "Current Protocols in Molecular Biology", Edited by Ausubel et al., John Wiley & Sons, 1988.

Bowie et al., "Deciphering the Message in Protein Sequences: Tolerance to Amino Acid Substitutions", Science, vol. 247, Mar. 16, 1990, pp. 1306-1310.

Boyle et al., "Bacterial Fc Receptors", Nature Biotechnology, vol. 5, 1987, pp. 697-703.

Braisted et al., "Minimizing a Binding Domain from Protein A", Proc. Natl. Acad. Sci. USA, vol. 93, Jun. 1996, pp. 5688-5692.

Brown et al., "A Study of the Interactions Between an IgG-Binding Domain Based on the B Domain of Staphylococcal Protein A and Rabbit IgG", Molecular Biotechnology, vol. 10, 1998, pp. 9-16.

Brown et al., "Affinity Purification of Human IgG using Immobilised, Mutated Immunoglobulin-Binding Domains from Protein A of *Staphylococcus aureus*", Biochemical Society Transactions, vol. 26, 1998, pp. S249.

Cedergren et al., "Mutational Analysis of the Interaction between Staphylococcal Protein A and Human IgC", Protein Engineering, vol. 6, 1993, pp. 441-448.

Chen et al., "Immobilized protein ZZ, an Affinity Tool for Immunoglobulin Isolation and Immunological Experimentation", Biotechnology and Applied Biochemistry, vol. 45, 2006, pp. 87-92.

Database WPI, "Week 200702", Thomson Scientific, London GB, AN 2007-012290, XP002683879.

Deisenhofer, Johann, "Crystallographic Refinement and Atomic Models of a Human Fc Fragment and its complex with Fragment B of Protein A From *Staphylococcus aureus* at 2.9- and 2.8-Å Resolution", Biochemistry, vol. 20, No. 9, Apr. 28, 1981, pp. 2361-2370.

Flatmark et al., "Multiple Forms of Cytochrome C in the Rat Precursor-Product Relationship Between the Main Component Cy I and the Minor Components Cy II and Cy 3 in Vivo", The Journal of Biological Chemistry, vol. 243, No. 7, Apr. 10, 1968, pp. 1623-1629.

Flatmark, "On the Heterogeneity of Beef Heart Cytochrome C", Acta Chemica Scandinavica, vol. 18, 1964, pp. 1656-1666.

Füglistaller, Paul, "Comparison of Immunogloublin Binding Capacities and Ligand Leakage Using Eight Different Protein A Affinity Chromatography Matrices", Journal of Immunological Methods, vol. 124, 1989, pp. 171-177.

GE Healthcare, "Affinity Chromatography—Principles and Methods", Oct. 2007, pp. 28-37.

Geiger et al., "Deamidation, Isomerization, and Racemization at Asparaginyl and Aspartyl Residues in Peptides", Journal of Biological Chemistry, vol. 262, No. 2, Jan. 15, 1987, pp. 785-794.

Geneseq, "*S. aureus* SpA Protein Inmunoglobul In-Binding Domain SpA-C", retrieved from EBI accession No. GSP: AOD36812, Apr. 17, 2008, 2 pages.

(56) References Cited

OTHER PUBLICATIONS

Ghose et al., "Antibody Variable Region Interactions With Protein A: Implications for the Development of Generic Purification Processes", Biotechnology and Bioengineering, vol. 92, No. 6, Dec. 20, 2005, pp. 665-673.

Ghose et al., "Protein A Affinity Chromatography for Capture and Purification of Monoclonal Antibodies and Fc-Fusion Proteins: Practical Considerations for Process Development", Chapter 16: Process Scale Bioseparations for the Biopharmaceutical Industry, edited by Shukla et al. CRC Press, 2007, pp. 463-489.

Godfrey et al., "A Sensitive Enzyme-Linked Immunosorbent Assay (ELISA) for the Detection of Staphylococcal Protein A (SpA) Present as a Trace Contaminant of Murine Immunoglobulins Purified on Immobilized Protein A", Journal of Immunological Methods, vol. 149, 1992, pp. 21-27.

Graille et al., "Crystal Structure of a *Staphylococcus aureus* Protein A Domain Complexed with the Fab Fragment of a Human IgM Antibody: Structural Basis for Recognition of B-Cell Receptors and Superantigen Activity", Proceedings of the National Academy of Sciences, vol. 97, No. 10, May 9, 2000, pp. 5399-5404.

Gronberg et al., "Rapid Development of CIP Protocols for Affinity Media", Poster Presented at the SPICA Conference, Zurich, Sep. 29-Oct. 1, 2008, 1 page.

Gulich et al., "Protein Engineering of an IgG-Binding Domain Allows Milder Elution Conditions During Affinity Chromatography", Journal of Biotechnology, vol. 76, No. 2-3, Jan. 21, 2000, pp. 233-243.

H3YRJ6, "UniProt Database Accession No. H3YRJ6", Available online at <http://www.uniprot.org/uniprot/H3YRJ6.txt>, retrieved on May 3, 2013, Published on Apr. 18, 2012, 1 page.

H3Z2S0, "UniProt Database Accession No. H3Z2S0", Available online at <http://www.uniprot.org/uniprot/H3Z2S0.txt>, retrieved on May 3, 2013, Published on Apr. 18, 2012, 1 page.

Hale et al., "Repeated Cleaning of Protein A Affinity Column with Sodium Hydroxide", Journal of Immunological Methods, vol. 171, 1994, pp. 15-21.

Henikoff et al., "Amino Acid Substitution Matrices from Protein Blocks", Proceedings of the National Academy of Sciences, vol. 89, Nov. 1992, pp. 10915-10919.

Hermanson et al., "Activation Methods", Chapter 2, Affinity Ligand Techniques, Academic Press, 1992, pp. 51-136.

Hjerten, Stellan, "The Preparation of Agarose Spheres for Chromatography of Molecules and Particles", Biochimica et Biophysica Acta, vol. 79, No. 2, Mar. 30, 1964, pp. 393-398.

Hober et al., "Protein A Chromatography for Antibody Purification", Journal of Chromatography B, vol. 848, No. 1, Mar. 15, 2007, pp. 40-47.

Hulett et al., "The Second and Third Extracellular Domains of FcγRI (CD64) Confer the Unique High Affinity Binding of IgG2a", Molecular Immunology, vol. 35, 1998, pp. 989-996.

Huston et al., "Multisite Association by Recombinant Proteins Can Enhance Binding Selectivity", Biophysical Journal, vol. 62, 1992, pp. 87-91.

Jansson et al., "All Individual Domains of Staphylococcal Protein A Show Fab Binding", FEMS Immunology & Medical Microbiology, vol. 20, No. 1, Jan. 1998, pp. 69-78.

Linhult et al., "Mutational Analysis of the Interaction between Albumin-Binding Domain from Streptococcal Protein G and Human Serum Albumin", Protein Science, vol. 11, 2002, pp. 206-213.

Ljungberg et al., "The Interaction Between Different Domains of Staphylococcal Protein A and Human Polyclonal IgG, IgA, IgM and F(ab')2: Separation of Affinity from Specificity", Molecular Immunology, vol. 30, No. 14, Oct. 1993, pp. 1279-1285.

Ljungquist et al., "Thiol-Directed Immobilization of Recombinant IgG-Binding Receptors", European Journal of Biochemistry, vol. 186, No. 3, Dec. 22, 1989, pp. 557-561.

McKerrow et al., "Deamidation of Asparaginyl Residues as a Hazard in Experimental Protein and Peptide Procedures", Anal Biochem., vol. 42, No. 2, Aug. 1971, pp. 565-568.

McKerrow et al., "Primary Sequence Dependence of the Deamidation of Rabbit Muscle Aldolase", Science, vol. 183, No. 4120., Jan. 11, 1974, p. 85.

Murray et al., "Harper's Biochemistry", 23rd Edition, Chapter 4, Section I, "Structure and Functions of Proteins and Enzymes", Amino Acids, 1993, pp. 23-28.

Needleman et al., "A General Method Applicable to the Search for Similarities in the Amino Acid Sequence of Two Proteins", Journal of molecular biology, vol. 48, 1970, pp. 443-453.

Nilsson et al., "A Synthetic IgG-Binding Domain Based on Staphylococcal Protein A", Protein Engineering, vol. 1, No. 2, Jan. 1, 1987, pp. 107-113.

Nord et al., "Binding Proteins Selected from Combinatorial Libraries of an α-Helical Bacterial Receptor Domain", Nature Biotechnology, vol. 15, Aug. 1997, pp. 772-777.

O'Cuinn, G., "Peptide Metabolism in Cytoplasm of Brain Cell", Biochemical Society Transactions, vol. 26, No. 3, 1998, pp. 279-292.

Pace et al., "How to Measure and Predict the Molar Absorption Coefficient of a Protein", Protein Science, vol. 4, 1995, pp. 2411-2423.

PALL Life Sciences, "Protein A Ceramic Hyper D F—Affinity Chromatography Sorbent", Product Note LPN PN702-004, 2004, 6 pages.

Palmer et al., "Design of stability at Extreme Alkaline pH in Streptococcal Protein G", Journal of Biotechnology, vol. 134, 2008, pp. 222-230.

Patel et al., "Chemical Pathways of Peptide Degradation II Kinetics of Deamidation of an Asparaginyl Residue in a Model Hexapeptide", Pharmaceutical Research, vol. 7, No. 7, 1990, pp. 703-711.

International Preliminary Report on Patentability Received for PCT Patent Application No. PCT/US2012/041070, mailed on Dec. 27, 2013, 13 pages.

International Search Report and Written Opinion Received for PCT Patent Application No. PCT/US2012/041070, mailed on Aug. 14, 2013, 7 pages.

Pearson et al., "Improved Tools for Biological Sequence Comparison", Proceedings of the National Academy of Sciences, vol. 85, No. 8, Apr. 1, 1988, pp. 2444-2448.

Popplewell et al., "Synthesis and Mutagenesis of an IgG-Binding Protein Based upon Protein A of *Staphylococcus aureus*", Protein Engineering, vol. 4, No. 8, 1991, pp. 963-970.

Porath et al., "Group Fractionation of Plasma Proteins on Dipolar Ion Exchangers", Journal of Chromatography A, vol. 51, 1970, pp. 479-489.

Q683L6, "UniProt Database Accession No. Q683L6", Available online at <http://www.uniprot.org/uniprot/Q683L6.txt>, Published on Oct. 11, 2004, Retrieved on May 3, 2013, 1 page.

Robinson et al. "Controlled Deamidation of Peptides and Proteins: An Experimental Hazard and a Possible Biological Timer", Proceedings of the National Academy of Sciences, vol. 66, No. 3, Jul. 1970, pp. 753-757.

Robinson et al., "Rates of Nonenzymatic Deamidation of Glutaminyl and Asparaginyl Residues in Pentapeptides", Journal of the American Chemical Society, vol. 95, No. 24, 1973, pp. 8156-8159.

Robinson et al., "Sequence Dependent Deamidation Rates for Model Peptides of Cytochrome C", International Journal of Peptide and Protein Research, vol. 6, No. 1, 1974, pp. 31-35.

Robinson et al., "Sequence Dependent Deamidation Rates for Model Peptides of Histone IV", International Journal of Peptide and Protein Research, vol. 6, No. 5, 1974, pp. 279-282.

Roque et al., "Affinity-Based Methodologies and Ligands for Antibody Purification: Advances and Perspectives", Journal of Chromatography A, vol. 1160, 2007, pp. 44-55.

Saito et al., "High Level Expression of a Synthetic Gene Coding for IgC-Binding Domain B of Staphylococcal Protein A", Protein Engineering, vol. 2, 1989, pp. 481-487.

Sambrook et al., "Molecular Cloning: A Laboratory Manual", Cold Spring Harbor Laboratory, 1989.

Scotchler et al., "Deamidation of Glutaminyl Residues: Dependence on pH, Temperature, and Ionic strength", Analytical Biochemistry, vol. 59, No. 1, May 1974, pp. 319-322.

(56) References Cited

OTHER PUBLICATIONS

Sjodahl, Jorgen, "Structural Studies on the Four Repetitive Fc-Binding Regions in Protein A from *Staphylococcus aureus*", European Journal of Biochemistry, vol. 78, No. 2, Sep. 1977, pp. 471-490.

Smith et al., "Comparison of Biosequences", Advances in Applied Mathematics, vol. 2, No. 4, Dec. 1981, pp. 482-489.

Starovasnik et al., "Antibody Variable Region Binding by Staphylococcal Protein A: Thermodynamic Analysis and Location of the Fv Binding Site on E-Domain", Protein Science, vol. 8, No. 7, Jul. 1999, pp. 1423-1431.

Ulhen et al., "Complete Sequence of the Staphylococcal Gene Encoding Protein A. A Gene Evolved through Multiple Duplications" The Journal of Biological Chemistry, vol. 259, Feb. 10, 1984, pp. 1695-1702.

```
E  -------AQQNAFYQVLNMPNLNADQRNGFIQSLKDDPSQSANVLGEAQKLNDSQAPK  51 (SEQ ID NO:1)
D  ADAQQNKFNKDQQSAFYEILNMPNLNEEQRNGFIQSLKDDPSQSTNVLGEAKKLNESQAPK  61 (SEQ ID NO:5)
A  --ADNN-FNKEQQNAFYEILNMPNLNEEQRNGFIQSLKDDPSQSANLLAEAKKLNESQAPK  58 (SEQ ID NO:2)
B  ---ADNKFNKEQQNAFYEILHLPNLNEEQRNGFIQSLKDDPSQSANLLAEAKKLNDAQAPK  58 (SEQ ID NO:3)
C  ---ADNKFNKEQQNAFYEILHLPNLTEEQRNGFIQSLKDDPSVSKEILAEARKLNDAQAPK  58 (SEQ ID NO:4)
Z  ---VDNKFNKEQQNAFYEILHLPNLNEEQRNAFIQSLKDDPSQSANLLAEAKKLNDAQAPK  58 (SEQ ID NO:6)
```

Figure 1. amino acid sequence alignment

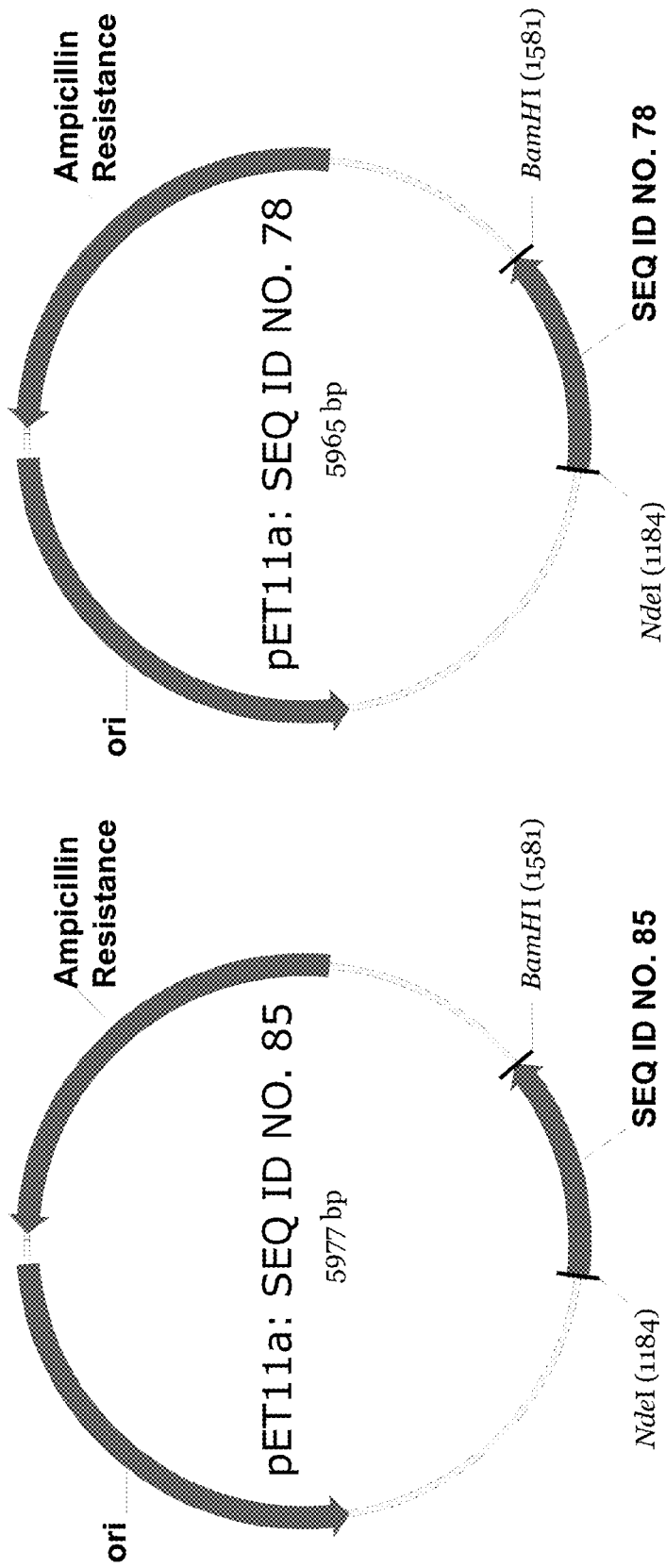
Figure 2. plasmid map

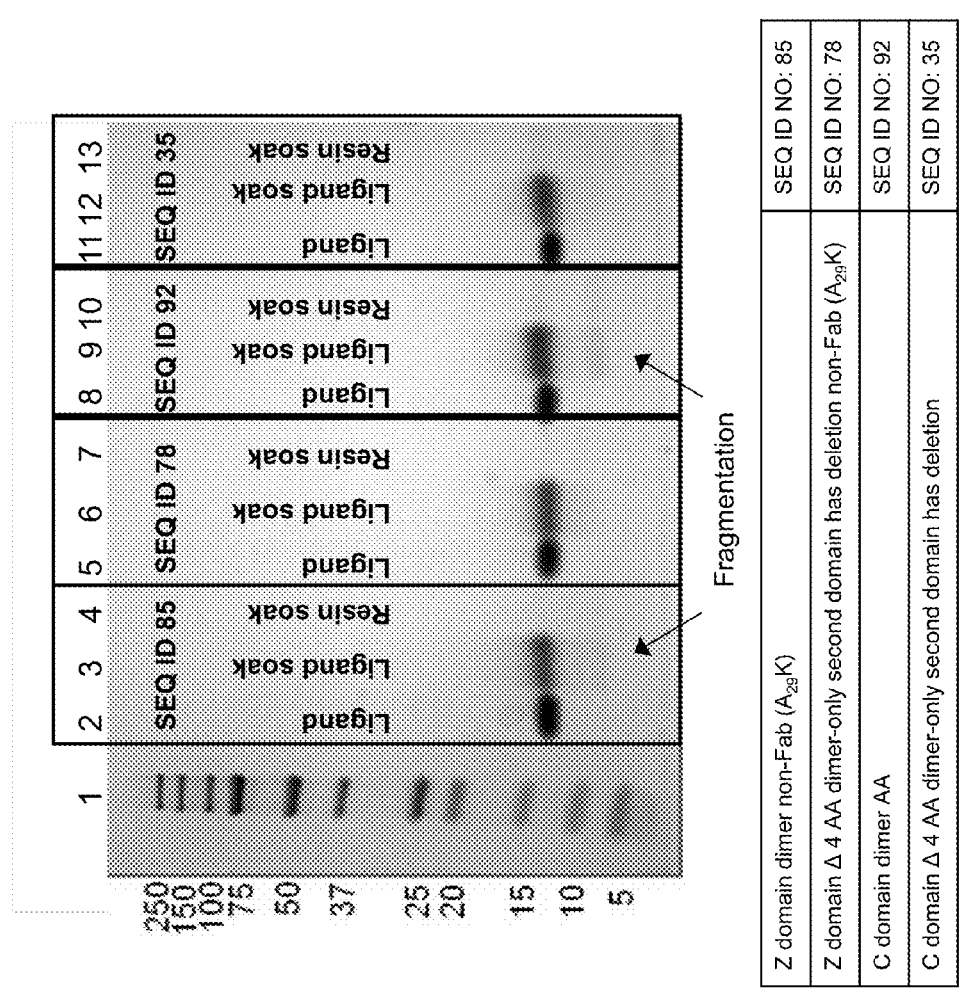
Figure 3. SDS-PAGE comparison of ligands (before and after extended caustic soak) and immobilized ligands (after extended caustic soak)

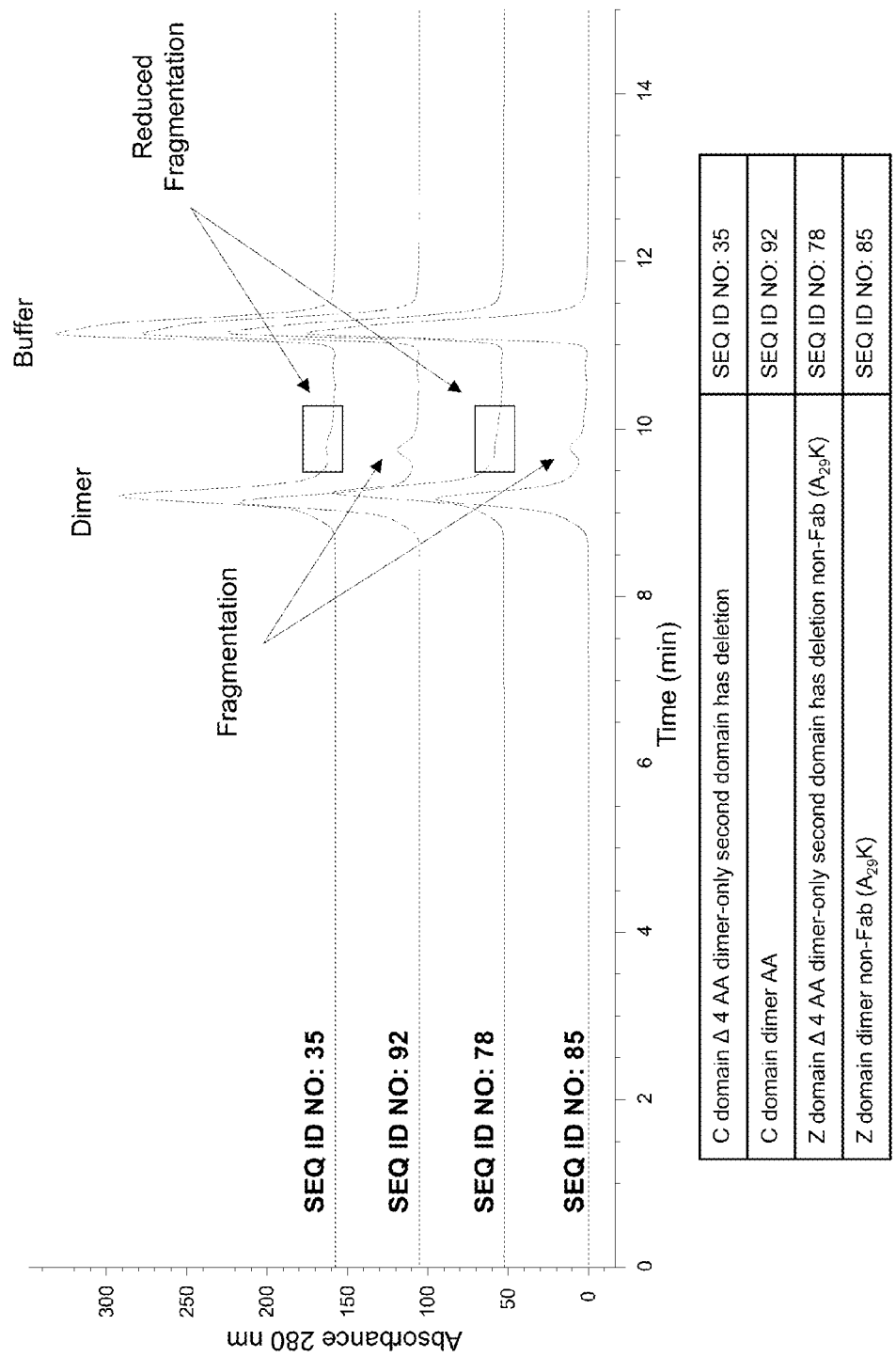
Figure 4. SEC comparison of ligands after extended caustic soak

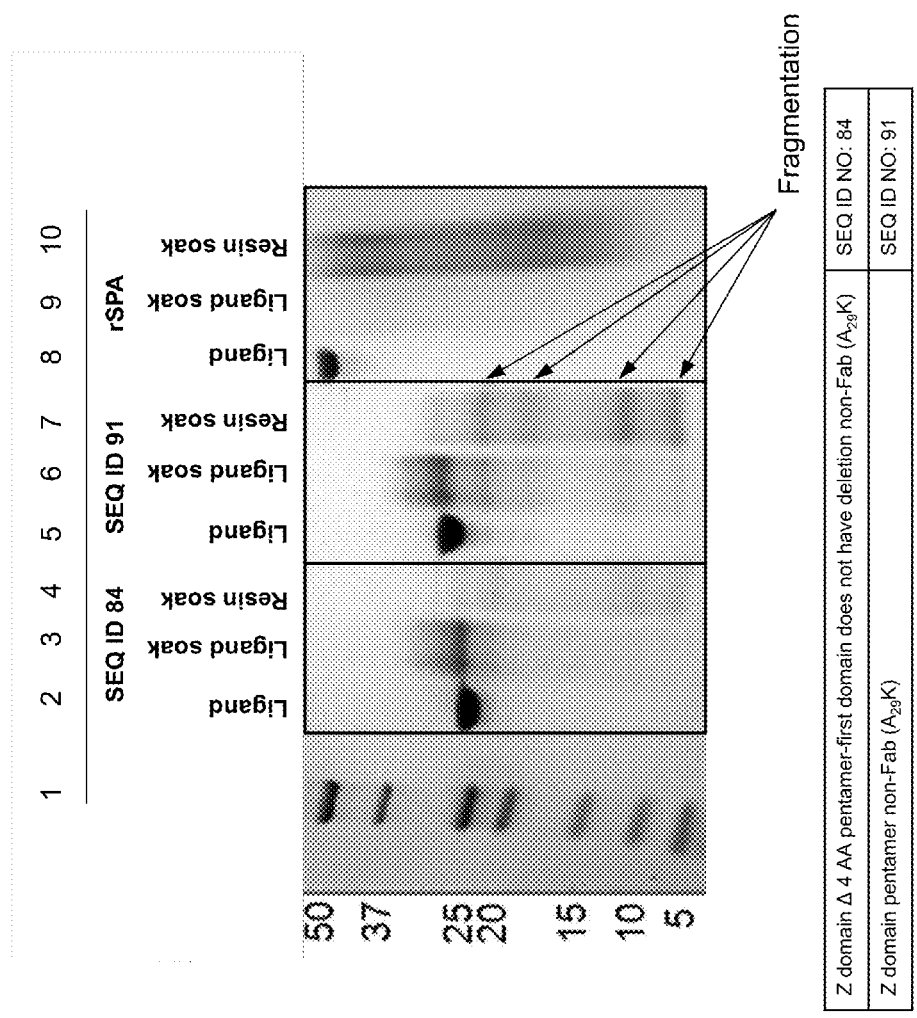
Figure 5. SDS-PAGE comparison of ligands (before and after extended caustic soak) and immobilized ligands (after extended caustic soak)

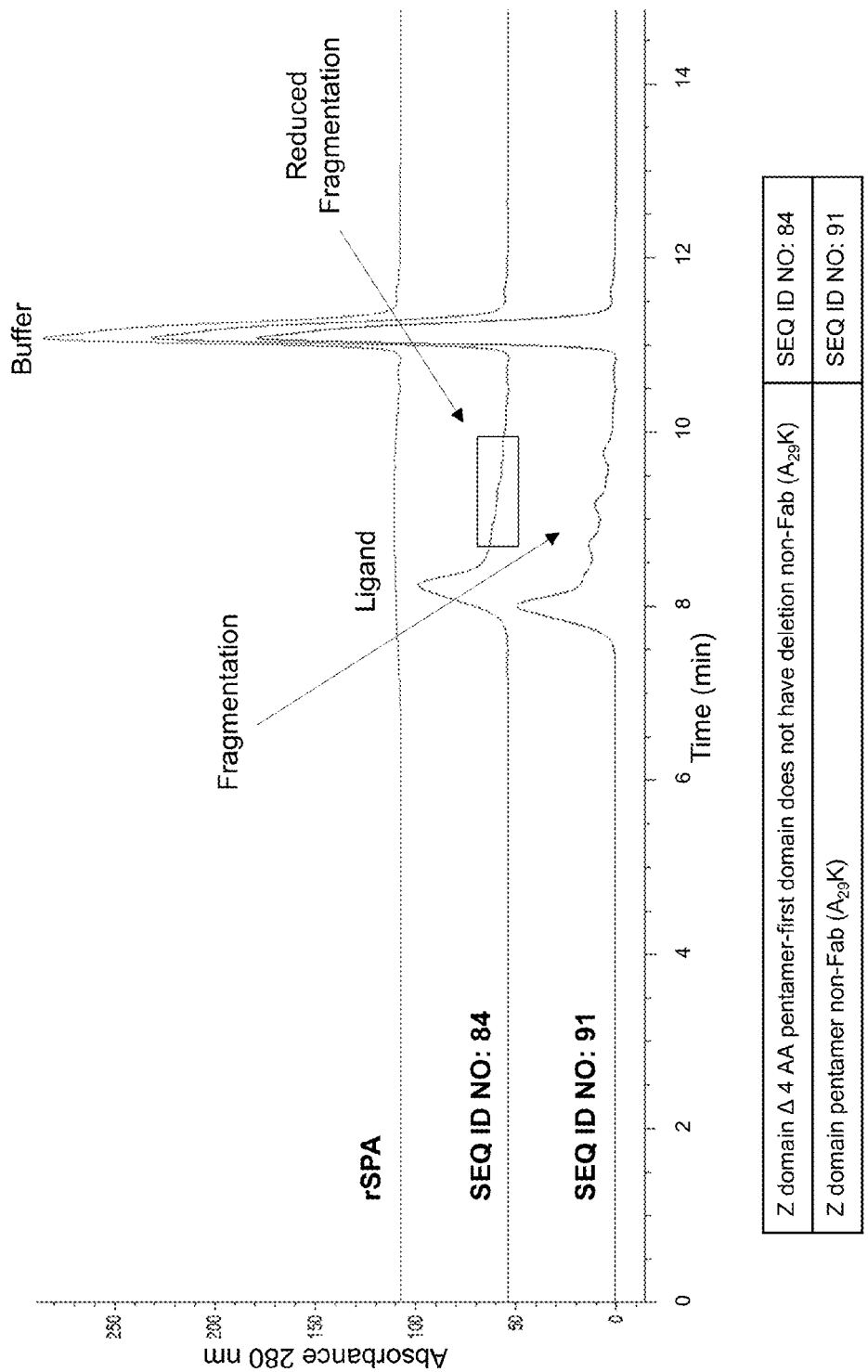
Figure 6. SEC comparison of ligands after extended caustic soak

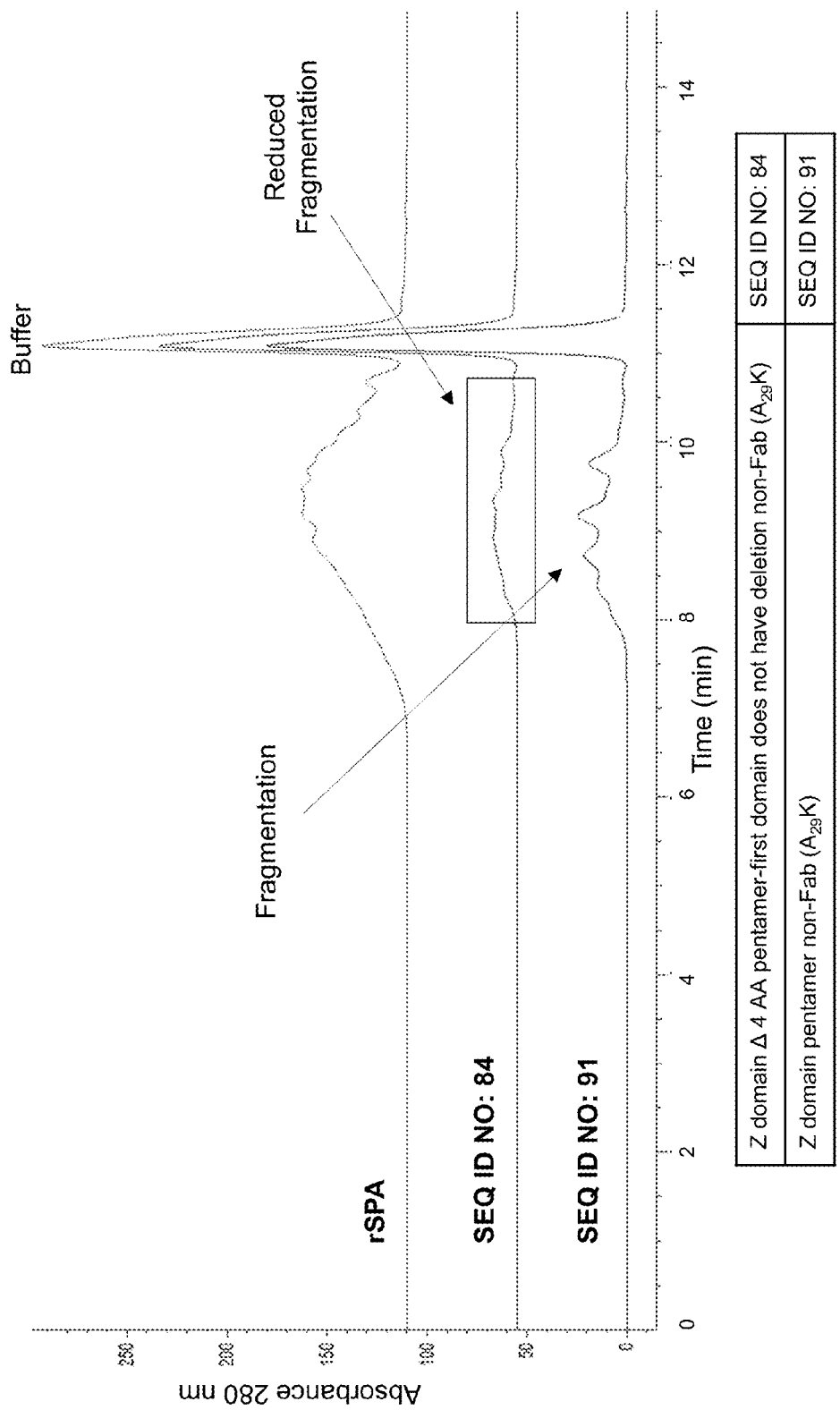
Figure 7. SEC comparison of immobilized ligands after extended caustic soak

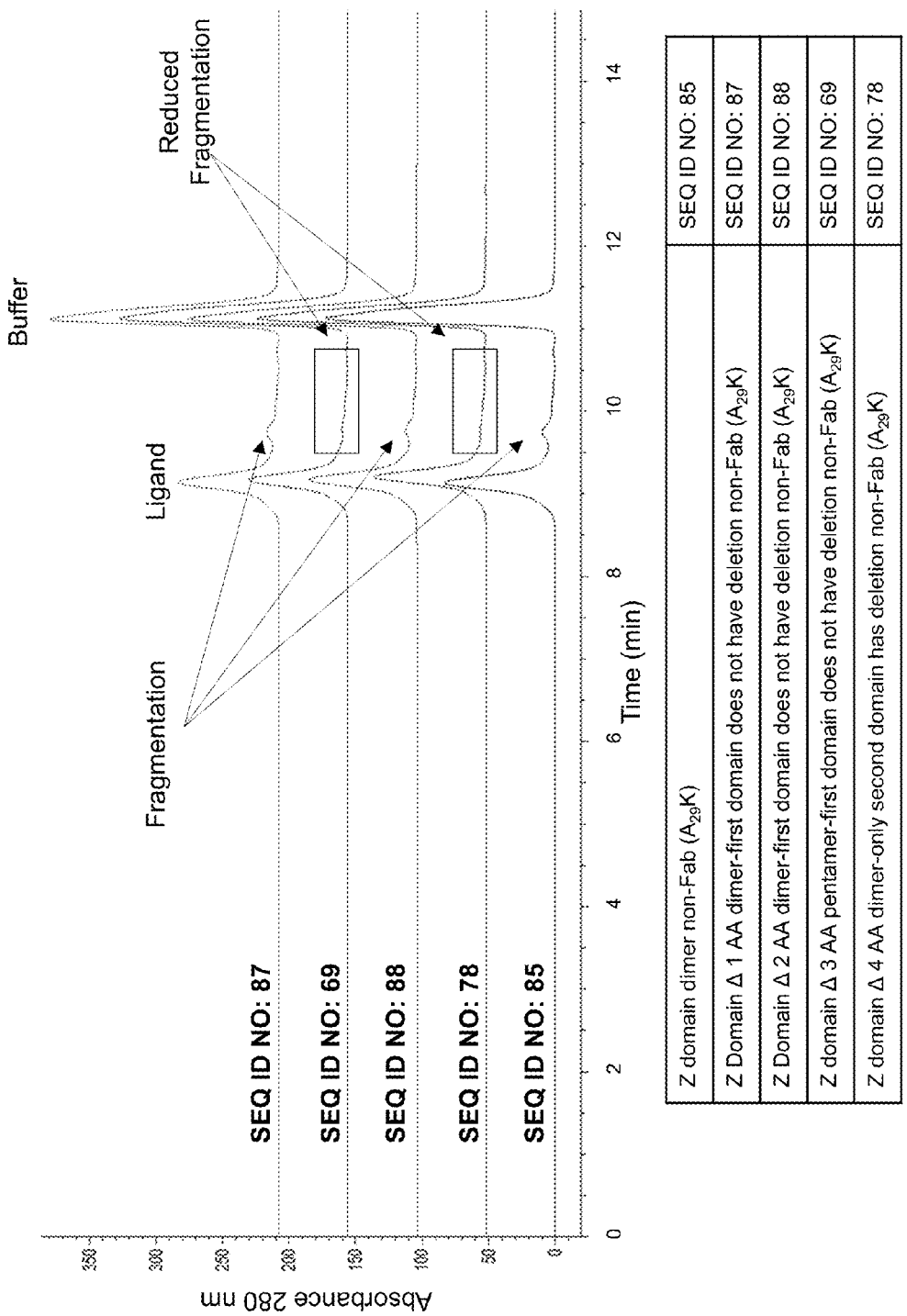
Figure 8. SEC comparison of ligands after extended caustic soak

US 9,376,474 B1

CHROMATOGRAPHY MATRICES INCLUDING NOVEL *STAPHYLOCOCCUS AUREUS* PROTEIN A BASED LIGANDS

RELATED APPLICATIONS

The present application is a Continuation Application of U.S. application Ser. No. 14/683,738, filed on Apr. 10, 2015, which is a Continuation Application of U.S. application Ser. No. 14/534,999, filed on Nov. 6, 2014, and which is issued as U.S. Pat. No. 9,018,305, on Apr. 28, 2015, which is a Continuation Application of U.S. application Ser. No. 14/298,332, filed on Jun. 6, 2014, and which issued as U.S. Pat. No. 8,895,706, on Nov. 25, 2014, which is a continuation of U.S. patent application Ser. No. 13/489,999, filed on Jun. 6, 2012, and which issued as U.S. Pat. No. 8,754,196 on Jun. 17, 2014, which claims the benefit of priority of U.S. Provisional Patent Application No. 61/494,701, filing date Jun. 8, 2011, each of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Dec. 3, 2015, is named MCA1353_4US_SL.txt and is 124,467 bytes in size.

FIELD OF THE INVENTION

The present invention relates to chromatography matrices including ligands based on one or more domains of immunoglobulin-binding proteins such as, *Staphylococcus aureus* Protein A (SpA) as well as methods of using the same.

BACKGROUND

Ligands used in affinity chromatography typically confer a high selectivity for the target molecule, thereby resulting in high yield, high purity and fast and economical purification of target molecules. *Staphylococcus aureus* Protein A-based reagents and chromatography matrices have found a widespread use in the field of affinity chromatography for capture and purification of antibodies and Fc-containing proteins as well as in analytical-scale antibody detection methods due to its ability to bind IgG, without significantly affecting the affinity of the immunoglobulin for antigen.

Accordingly, various reagents and media comprising Protein A-ligands have been developed and are commercially available, for example, ProSep®-vA High Capacity, ProSep® vA Ultra and ProSep® UltraPlus (MILLIPORE) and Protein A Sepharose™, MabSelect™, MabSelect Xtra™, MabSelect SuRe™ (GE HEALTHCARE), MabSelect SuRe™ LX and Poros MabCapture A™ (LIFE TECHNOLOGIES).

In order to maintain selectivity of the chromatography ligands including ligand bound solid supports such as SpA bound chromatography matrices, matrices have to be cleaned and are typically cleaned under acidic or alkaline conditions, e.g., with sodium hydroxide (NaOH). For example, a standard process which is used for cleaning and restoring the matrix is a cleaning-in-place (CIP) alkaline protocol, which typically involves treatment of the ligand bound matrix with NaOH concentration ranging from 0.05M to 1M, resulting in pH range 12.7 to 14.0. Typically, exposure of an affinity chromatography matrix to repeated CIP cycles results in significant loss of binding capacity of the matrix for a target molecule over time, requiring the use of a greater amount throughout the process, of often very expensive ligands which are bound to matrices. This is both uneconomical and undesirable as it results in the purification process becoming more expensive as well as lengthy.

SUMMARY OF THE INVENTION

Protein A based chromatography matrices have been previously described in the art which appear to show a reduced loss of binding capacity for a target molecule following treatment with alkaline conditions. See, e.g., U.S. Patent Publication No. 20100221844, which describes affinity chromatography matrices incorporating wild-type (wt) B or Z domains of SpA with multiple point attachment to the matrix, which show up to 95% of the initial binding capacity even after exposure to 0.5M NaOH for 5 hours or more. Also, U.S. Patent Publication No. 20100048876 describes a chromatography matrix incorporating wild type C domain of SpA as well as a C domain containing a deletion of amino acid residues 3 through 6, which appear to show up to 95% of the initial binding capacity after exposure to 0.5M for about 5 hours. These ligands are immobilized via a cysteine directed single-point attachment to the matrix. Further, chromatography matrices have been described which incorporate Protein A domains containing mutations at one or more asparagine residues of the protein, where the matrices appear to show a reduced loss in binding capacity relative to the wild type SpA, following exposure to alkaline conditions and appear to be immobilized via a single-point attachment to the matrix. See, e.g., U.S. Pat. No. 6,831,161.

Although, the aforementioned affinity chromatography matrices appear to show a reduced loss in binding capacity for a target molecule following exposure to caustic conditions, some of these matrices appear to show a large degree of fragmentation of ligand, e.g., as observed using SDS-PAGE and/or size exclusion chromatography (SEC), following exposure to caustic conditions. Such fragmentation is undesirable, as a large degree of fragmentation of ligand results in smaller fragments of ligands being present which are more difficult to remove and separate from the target molecule, thereby increasing the likelihood that such potentially immunogenic fragments will co-purify with the therapeutic target molecule. Furthermore, a large degree of fragmentation results in an increased loss in binding capacity of the matrix for a target molecule.

The present invention provides affinity chromatography ligands and matrices incorporating the same, where the ligands are based on one or more *Staphylococcus aureus* Protein A (SpA) domains having a deletion from the N-terminus, starting at position 1 or position 2 of the domain. These ligands and matrices show reduced fragmentation during purification use, as evidenced by SDS-PAGE and/or SEC techniques, relative to some of the previously described ligands, thereby making them more attractive and economical candidates for use in affinity chromatography.

In one aspect according to the present invention, affinity chromatography matrices are provided, which includes one or more B domains of SpA having a deletion, one or more C domains of SpA having a deletion or one or more Z domains of SpA having a deletion, where the one or more domains are attached to a solid support.

In one embodiment, an affinity chromatography matrix according to the present invention includes a ligand attached to a solid support, where the ligand comprises one or more B domains of *Staphylococcus aureus* Protein A (SpA), where at least one B domain comprises a deletion of at least 3 consecutive amino acids from the N- In another embodiment, an affinity chromatography matrix according to the present invention comprises a ligand attached to a solid support, where the ligand comprises one or more C domains of *Staphylococcus aureus* Protein A (SpA), where at least one C domain comprises a deletion of at least 3 consecutive amino acids from the N-terminus.

In yet another embodiment, an affinity chromatography matrix according to the present invention comprises a ligand attached to a solid support, where the ligand comprises one or more Z domains of *Staphylococcus aureus* Protein A (SpA), where at least one Z domain comprises a deletion of at least 3 consecutive amino acids from the N-terminus.

In still other embodiments, an affinity chromatography matrix according to the present invention comprises a ligand attached to a solid support, where the ligand comprises two or more B domains, two or more C domains or two or more Z domains, or any combination of B, C and Z domains, where at least one of B, C or Z domain comprises a deletion of at least 3 consecutive amino acids from the N-terminus.

In various embodiments according to the present invention, more than one site on each ligand is attached to a solid support (i.e., multipoint attachment).

In various embodiments according to the present invention, the ligand exhibits reduced fragmentation, as determined by SDS-PAGE or by size-exclusion chromatography (SEC), relative to its wt counterpart, following exposure of the ligand or the matrix containing the ligand to 0.5M NaOH for at least 5 hours.

In some embodiments according to the present invention, the ligand comprises a deletion of 3 amino acids from the N-terminus, a deletion of 4 amino acids from the N-terminus or a deletion of 5 amino acids from the N-terminus, where more than one site on the ligand is attached to a solid support, thereby to form an affinity chromatography matrix.

In a particular embodiment, a ligand has an amino acid sequence set forth in any of SEQ ID NOs:13-42, SEQ ID NOs:55-84 and SEQ ID NOs: 93-94.

In another embodiment, a ligand according to the present invention has the following structure: $[(X)_n, (Y)_m]_{n+m}$, where X represents a B domain, a Z domain or a C domain of SpA, n represents the number of domains ranging from zero through (m−1), Y represents a B domain or a Z domain or a C domain of SpA having at least 3 consecutive amino acids deleted from the N-terminus and m represents the number of Y domains ranging from one through eight, where more than one site on the ligand is attached to a solid support (e.g., a chromatography matrix).

In some embodiments according to the present invention, the ligand comprises two B domains or two Z domains or two C domains of SpA, or one B and one C domain, or one B and one Z domain, or one C and one Z domain, where at least one B domain or at least one Z domain or at least one C domain includes a deletion of three consecutive amino acids from the N-terminus or a deletion of four consecutive amino acids from the N-terminus or a deletion of five consecutive amino acids from the N-terminus. It is understood that the various domains may be arranged in any order.

In another embodiment, a ligand according to the present invention comprises three B domains or three Z domains or three C domains, or any combination of B, C or Z domains in any order, where at least one B domain or at least one Z domain or at least one C domain comprises a deletion of three consecutive amino acids from the N-terminus or a deletion of four consecutive amino acids from the N-terminus or a deletion of five consecutive amino acids from the N-terminus.

In yet another embodiment, a ligand according to the present invention comprises four B domains or four Z domains or four C domains, or any combination of B, Z or C domains in any order, where at least one B domain or at least one Z domain or at least one C domain comprises a deletion of three consecutive amino acids from the N-terminus or a deletion of four consecutive amino acids from the N-terminus or a deletion of five consecutive amino acids from the N-terminus.

In yet another embodiment, a ligand according to the present invention comprises five B domains or five Z domains or five C domains, or any combination of B, Z or C domains in any order, where at least one B domain or at least one Z domain or at least one C domain comprises a deletion of three consecutive amino acids from the N-terminus or a deletion of four consecutive amino acids from the N-terminus or a deletion of five consecutive amino acids from the N-terminus.

In yet another embodiment, a ligand according to the present invention comprises six B domains or six Z domains or six C domains, or any combination of B, Z or C domains in any order, where at least one B domain or at least one Z domain or at least one C domain comprises a deletion of three consecutive amino acids from the N-terminus or a deletion of four consecutive amino acids from the N-terminus or a deletion of five consecutive amino acids from the N-terminus.

In yet another embodiment, a ligand according to the present invention comprises seven B domains or seven Z domains or seven C domains, or any combination of B, Z or C domains in any order, where at least one B domain or at least one Z domain or at least one C domain comprises a deletion of three consecutive amino acids from the N-terminus or a deletion of four consecutive amino acids from the N-terminus or a deletion of five consecutive amino acids from the N-terminus.

In a further embodiment, a ligand according to the present invention comprises eight B domains or eight Z domains or eight C domains, or any combination of B, Z or C domains in any order, where at least one B domain or at least one Z domain or at least one C domain comprises a deletion of three consecutive amino acids from the N-terminus or a deletion of four consecutive amino acids from the N-terminus or a deletion of five consecutive amino acids from the N-terminus.

Additionally, provided herein are methods of using the affinity chromatography matrices. Accordingly, a method of affinity purifying one or more target molecules (e.g., immunoglobulins or Fc-containing proteins) from a sample is provided, where the method comprises the steps of: (a) providing a sample comprising one or more target molecules (e.g., immunoglobulins or Fc-containing proteins); (b) contacting the sample with a matrix according to the invention under conditions such that the one or more target molecules (e.g., immunoglobulins or Fc-containing proteins) bind to the matrix; and (c) recovering the one or more bound target molecules (e.g., immunoglobulins or Fc-containing proteins) by eluting under suitable conditions such as, for example, a suitable pH.

In some embodiments, an affinity chromatography matrix according to the present invention retains at least 95% of its initial binding capacity for a target molecule after 5 hours, or after 10 hours, or after 15 hours, or after 20 hours, or after 25 hours, or after 30 hours of incubation in 0.5 M NaOH.

In a particular embodiment, an affinity chromatography matrix according to the present invention retains at least 95% of its initial binding capacity after 5 hours incubation in 0.5M NaOH.

In yet another embodiment, an affinity chromatography matrix according to the present invention retains at least 95% of its initial binding capacity for a target molecule after 25 hours incubation in 0.1M NaOH; at least 85% of its initial binding capacity for a target molecule after 25 hours incubation in 0.3M NaOH; or at least 65% of its initial binding capacity for a target molecule after 25 hours incubation in 0.5M NaOH.

The immunoglobulins which are capable of being bound by the various ligands described herein include, e.g., IgG, IgA and IgM, or any fusion protein comprising an antibody and any fragment of antibody, which is capable of binding to SpA.

Also provided herein are nucleic acid molecules encoding the various ligands described herein, as well as host cells including such nucleic acid molecules. In some embodiments, a host cell is a prokaryotic cell. In other embodiments, a host cell is a eukaryotic cell.

In some embodiments, the present invention provides SpA-based affinity chromatography matrices which exhibit altered (increased or decreased) binding to a Fab portion of an immunoglobulin compared to the wt SpA ligands, while retaining the ability to bind the Fc portion of the immunoglobulin. In one embodiment, an SpA-based matrix according to the present invention exhibits a decreased binding to a Fab portion of an immunoglobulin compared to wt SpA. In a particular embodiment, a chromatography matrix incorporates a SpA ligand, which includes a lysine at position 29, instead of a glycine (in case of B and C domains of SpA) or instead of an alanine (in case of the Z domain of SpA).

BRIEF DESCRIPTION OF THE DRAWINGS

FIG. 1 depicts the amino-acid sequence alignments for the wild type (wt) IgG binding domains of SpA as well as the Z domain, represented by SEQ ID NOs: 1-6.

FIG. 2 depicts schematic diagrams of the plasmid pET11a containing the nucleic acid sequence encoding the dimeric Z domain ligand with a A29K mutation, the amino acid sequence shown in SEQ ID NO:85 (control), and plasmid pET11a containing the nucleic acid sequence encoding the dimeric Z domain ligand with a A29K mutation as well as the second domain including a deletion of 4 consecutive amino acids from the N-terminus, the amino acid sequence shown in SEQ ID NO:78. The ligand constructs further include a His-tag sequence at the 3' end.

FIG. 3 is a Coomassie stained SDS-PAGE gel for analyzing the fragmentation pattern of free and immobilized dimeric Z and C ligands with or without caustic soak in 0.5M NaOH for 25 hrs. The description of the various Lanes of the SDS-PAGE gel is as follows. Lane 1: molecular marker; Lane 2: dimeric Z domain ligand with no caustic exposure (A29K with no deletions, shown in SEQ ID NO:85, which is used as the control and includes a His-tag); Lane 3: the dimeric Z domain ligand control subjected to 0.5M NaOH soak for 25 hours; Lane 4: the dimeric Z domain ligand control immobilized onto an agarose chromatography resin, which is subjected to 0.5M NaOH soak for 25 hours; Lane 5: the dimeric Z domain ligand having a deletion of 4 consecutive amino acids from the N-terminus of the second domain (A29K with the second domain having a deletion, shown in SEQ ID NO:78 and a His-tag) with no caustic exposure; Lane 6: the dimeric Z domain ligand of SEQ ID NO:78 with a His-tag subjected to 0.5M NaOH soak for 25 hours; Lane 7: the dimeric Z domain ligand of SEQ ID NO:78 with a His-tag immobilized onto an agarose chromatography resin and subjected to 0.5M NaOH soak for 25 hours; Lane 8: dimeric C domain ligand with no deletions used as a control (amino acid sequence shown in SEQ ID NO:92 plus having a His-tag) with no caustic exposure; Lane 9: the dimeric C domain ligand control subjected to 0.5M NaOH soak for 25 hours; Lane 10: the dimeric C domain ligand immobilized onto an agarose chromatography resin and subjected to 0.5M NaOH soak for 25 hours; Lane 11: dimeric C domain ligand having a deletion from the N-terminus of the second domain (amino acid sequence shown in SEQ ID NO:35 plus having a His-tag); Lane 12: dimeric C domain ligand of SEQ ID NO:35 plus a His-tag subjected to 0.5M NaOH soak for 25 hours; and Lane 13: dimeric C ligand of SEQ ID NO:35 plus a His-tag immobilized onto an agarose chromatography resin and subjected to 0.5M NaOH soak for 25 hours.

FIG. 4 is a chromatogram of an SEC analysis of the dimeric Z and C ligands summarized in the description of FIG. 3 above. The x-axis denotes the rentention time in minutes with smaller molecules having longer retention time than that of a larger molecule. The y-axis represents UV absorption at 280 nm in mAU. The evidence of reduced fragmentation for the dimeric Z and C domain ligands having a N-terminus deletion in the second domain, following extended caustic soak (i.e., 0.5M NaOH soak for 25 hours), is shown by way of boxes on the chromatogram and the presence of smaller fragments for the dimeric Z and C domain controls is shown by way of arrows.

FIG. 5 is a Coomassie stained SDS-PAGE gel for analyzing the fragmentation pattern of both free and immobilized pentameric Z domain ligands with or without caustic soak in 0.5M NaOH for 25 hours. The description of the various lanes of the SDS-PAGE gel is as follows: Lane 1: molecular weight marker; Lane 2: pentameric Z domain ligand having the A29K mutation and a deletion of 4 consecutive amino acids from the N-terminus of all but the first domain, the amino acid sequence of which is set forth in SEQ ID NO:84, with no caustic exposure; Lane 3: pentameric Z domain ligand of SEQ ID NO:84 subjected to 0.5M NaOH soak for 25 hours; Lane 4: pentameric Z domain ligand of SEQ ID NO:84 immobilized onto an agarose chromatography resin and subjected to 0.5M NaOH soak for 25 hours; Lane 5: pentameric Z domain ligand of SEQ ID NO:91, used as a control, which is not subjected to caustic soak; Lane 6: pentameric Z domain ligand control subjected to 0.5M NaOH soak for 25 hours; and Lane 7: pentameric Z domain ligand control immobilized onto an agarose chromatography resin and subjected to 0.5M NaOH soak for 25 hours. Further, Lanes 8, 9 and 10 relate to the results seen with subjecting rSPA to a similar treatment, where Lane 8 represents rSPA which is not subjected to any caustic soak; Lane 9 represents rSPA subjected to 0.5M NaOH soak for 25 hours and immobilized rSPA subjected to 0.5M NaOH soak for 25 hours. The bands represent the fragmentation, as depicted by arrows.

FIG. 6 is a chromatogram of an SEC analysis of the pentameric Z domain ligands summarized in the description of FIG. 5 above. The x-axis denotes the rentention time in minutes with smaller molecules having longer retention time than that of a larger molecule. The y-axis represents UV absorption at 280 nm in mAU. The evidence for reduced fragmentation in case of the pentameric Z domain ligands having a N-terminal deletion in all but the first domain, following extended caustic soak, is shown by way of boxes on the chromatogram and the presence of smaller fragments seen with the pentameric Z domain control is shown by way of an arrow pointing to the fragments. Further, extensive amount of fragmentation seen for rSPA can be also observed using SEC.

FIG. 7 is a chromatogram of an SEC analysis of the immobilized pentameric Z domain ligands summarized in the description of FIG. 5 above. The x-axis denotes the rentention time in minutes with smaller molecules having longer retention time than that of a larger molecule. The y-axis represents UV absorption at 280 nm in mAU. The evidence for reduced fragmentation in case of the immobilized pentameric Z domain ligand having an N-terminal deletion in the second domain, following extended caustic soak, is shown by way of a box on the chromatogram and the presence of smaller fragments seen with the pentameric Z domain control is shown by way of an arrow pointing to the fragments. Further, extensive amount of fragmentation seen for immobilized rSPA can be also observed using SEC.

FIG. 8 is a chromatogram of an SEC analysis of the free dimeric Z domain ligands following extended caustic soak, where the ligands include a N-terminus deletion of the first one (SEQ ID NO:87), first two (SEQ ID NO:88), first three (SEQ ID NO:69) or first four (SEQ ID NO:78) of the second domain of the dimeric ligands. The x-axis denotes the rentention time in minutes with smaller molecules having longer retention time than that of a larger molecule. The y-axis represents UV absorption at 280 nm in mAU. The evidence for reduced fragmentation in case of the dimeric ligands having first three or first four amino acids deleted from the N-terminus of the second domain following extended caustic soak is depicted by boxes. The presence of fragmentation observed following extended caustic soak of the dimeric ligands having no amino acid deletions (SEQ ID NO:85) or the first amino acid deleted or the first two amino acids deleted from the N-terminus of the second domain, is shown by way of arrows pointing to the presence of fragments on the chromatogram.

DETAILED DESCRIPTION OF THE INVENTION

Figure 9:
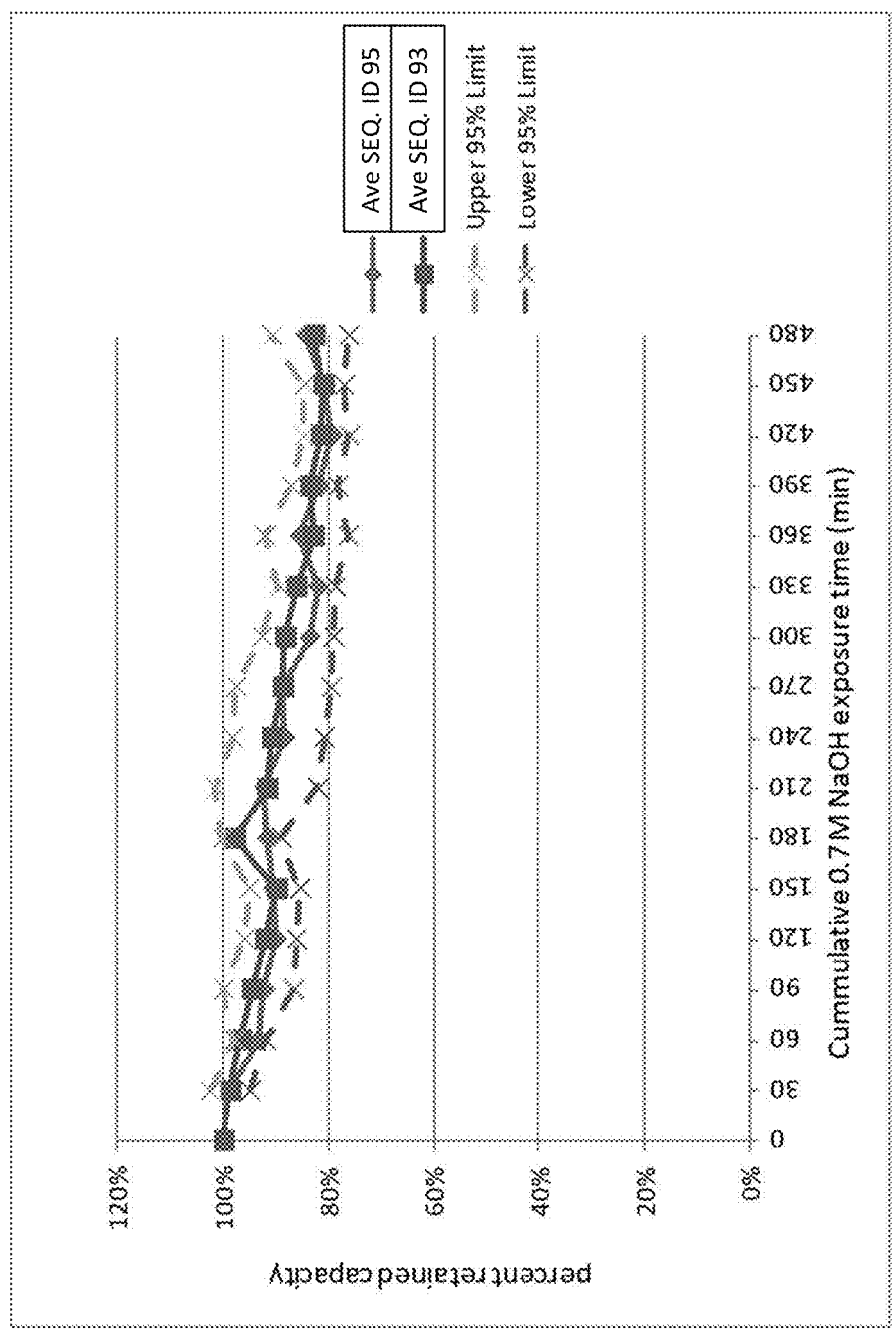
FIG. 9 compares the retained binding capacities of immobilized C domain pentameric ligands after repeated caustic exposure, where one pentameric ligand includes an N terminus deletion of 4 amino acids in each domain, the G29K mutation in each domain as well as an alanine as the very first amino acid in the pentamer (the amino acid sequence shown in SEQ ID NO:93); and the other pentameric ligand being its wt counterpart with the G29 K mutation (the amino acid sequence of which is shown in SEQ ID NO:95). The x-axis represents time of cumulative exposure of the chromatography matrices to 0.7M NaOH over 16 cycles of 30 mins each. The y-axis represents the percent retained binding capacity.

The present invention provides affinity chromatography matrices which incorporate ligands based on one or more domains of SpA, where the ligands, either alone or when immobilized onto a matrix, show reduced fragmentation during use in purification processes, relative to the corresponding wt domains of SpA.

Previously described exemplary SpA-based chromatography ligands include, for example, those described in U.S. Patent Publication No. 20100221844, which describes chromatography matrices which incorporate wild type B and Z domains of SpA, where more than one site on the ligand is attached to a chromatography matrix (i.e., multipoint attachment); those described in U.S. Patent Publication No. 20100048876, which discusses chromatography ligands based on the wt C domain of SpA, which are capable of binding the Fab portions of some antibodies and are coupled to an insoluble carrier at a single site using a terminal coupling group; and those described in U.S. Pat. No. 6,831,161, which discusses SpA-based alkaline based chromatography ligands where one or more asparagine amino acid residues have been modified.

As discussed above, while these ligands exhibit a reduced loss in binding capacity following exposure to alkaline conditions, some of these ligands show fragmentation during use in purification process, e.g., the ligands described in U.S. Publication No. 20100221844, which is highly undesirable. The ligands described herein, on the other hand, are far more attractive candidates for protein purification compared to the previously described ligands, in that they show reduced fragmentation following exposure to alkaline conditions during the regeneration and cleaning-in-place (CIP) protocols that are routinely used in protein purification processes.

In order that the present disclosure may be more readily understood, certain terms are first defined. Additional definitions are set forth throughout the detailed description.

I. Definitions

As used herein, the term "SpA," "Protein A" or "*Staphylococcus aureus* Protein A," refers to a 42 Kda multi-domain protein isolated from the bacterium *Staphylococcus aureus*. SpA is bound to the bacterial cell wall via its carboxy-terminal cell wall binding region, referred to as the X domain. At the amino-terminal region, it includes five immunoglobulin-binding domains, referred to as E, D, A, B, and C (Sjodhal, *Eur J Biochem*. September 78(2):471-90 (1977); Uhlen et al., *J Biol Chem*. February 259(3):1695-702 (1984). Each of these domains contains approximately 58 amino acid residues, and they share 65-90% amino acid sequence identity.

Each of the E, D, A, B and C domains of SpA possess distinct Ig-binding sites. One site is for Fc□□ (the constant region of IgG class of Ig) and the other is for the Fab portion of certain Ig molecules (the portion of the Ig that is responsible for antigen recognition). It has been reported that each of the domains contains a Fab binding site. The non-Ig binding portion of SpA is located at the C-terminus and is designated the X region or X-domain.

The Z domain of SpA is an engineered analogue of the B domain of SpA and includes a valine instead of an alanine at position 1 and an alanine instead of a glycine residue at position 29 (Nilsson, et al., *Protein engineering, Vol.* 1, *No.* 2, 107-113, 1987).

The cloning of the gene encoding SpA is described in U.S. Pat. No. 5,151,350, the entire contents of which are incorporated by reference herein in their entirety.

The present invention provides affinity chromatography matrices which incorporate SpA-based ligands, where the ligands (both free as well as immobilized ligands) exhibit reduced fragmentation, as observed by SDS-PAGE and SEC, following regeneration and CIP protocols that are routinely used during protein purification process.

In some aspects according to the present invention, an affinity ligand comprises one or more B domains or one or more Z domains or one or more C domains, or any combinations thereof, where at least one B domain or at least one Z domain or at least one C domain comprises a deletion of 3 consecutive amino acids from the N-terminus, or 4 consecutive amino acids from the N-terminus or 5 consecutive amino acids from the N-terminus, starting at position 1 or at position 2.

In some embodiments according to the present invention, more than one site of an affinity ligand is attached to a chromatography matrix (i.e., multipoint attachment). In a particular embodiment, the present invention provides an affinity chromatography matrix comprising one or more B domains of SpA attached to a chromatography matrix, where more than one site of the ligand is attached to the matrix and where at least one B domain has a deletion of 3 consecutive amino acids from the N-terminus or 4 consecutive amino acids from the N-terminus or 5 consecutive amino acids from the N-terminus, starting at position 1 or at position 2 of the wt B domain sequence.

In another embodiment, the present invention provides an affinity chromatography matrix comprising one or more Z domains of SpA attached to a chromatography matrix, where more than one site of the ligand is attached to the matrix and where at least one Z domain has a deletion of 3 consecutive amino acids from the N-terminus or 4 consecutive amino acids from the N-terminus or 5 consecutive amino acids from the N-terminus, starting at position 1 or position 2 of the wt Z domain sequence.

In yet another embodiment, the present invention provides an affinity chromatography matrix comprising one or more C domains of SpA, attached to a chromatography matrix, where more than one site of the ligand is attached to the matrix and where at least one C domain has a deletion of 3 consecutive amino acids from the N-terminus or 4 consecutive amino acids from the N-terminus or 5 consecutive amino acids from the N-terminus, starting at position 1 or at position 2 of the wt C domain sequence.

In a particular embodiment, the present invention provides an alkaline stable affinity chromatography ligand which includes five C domains of SpA, with each domain including a G29K mutation as well as 4 amino acids deleted from the N-terminus, starting at position 1, and the pentameric form including an extra alanine as the first amino acid to facilitate homogeneous post translational processing of the protein.

In some embodiments, SpA ligands described herein further include the glycine amino acid residue at position 29 replaced with a lysine amino acid residue (in case of B and C domains) or the alanine amino acid residue at position 29 replaced with a lysine amino acid residue (in case of Z domain).

The term "parental molecule" or "wild-type (wt) counterpart" or "wt protein" or "wt domain," as used herein, is intended to refer to a corresponding protein (SpA) or a domain of a protein (e.g., B, Z or C domains of SpA) in its substantially native form, which is generally used as a control herein. A wt counterpart control, as used herein, which corresponds to a SpA domain in its substantially native form may include one amino acid change from the corresponding SpA domain to alter Fab binding; however, is otherwise identical in sequence to the corresponding wt domain. The ligands according to the present invention exhibit reduced fragmentation (in case of both free and immobilized forms) relative to their wt counterparts (i.e., completely wt or including a mutation to alter Fab binding), as evidenced by the experiments discussed in the Examples herein. In various embodiments, the wt counterpart of a B domain or C domain based ligand according to the present invention is the wt B domain of SpA or wt C domain of SpA, the amino acid sequences of which are set forth in SEQ ID NO:3 and SEQ ID NO:4, respectively. In certain embodiments, a wt counterpart of a Z domain based ligand is the Z domain amino acid sequence set forth in SEQ ID NO:6. In certain embodiments, a wt counterpart of a B, C or Z domain, is substantially identical to the sequence of the B, C or Z domain mentioned above, but for a mutation at position 29 to alter the Fab-binding of the domain. Accordingly, in certain embodiments, a wt counterpart of a B domain based ligand includes the amino acid sequence set forth in SEQ ID NO:45 (G29K), a wt counterpart of a C domain based ligand includes the amino acid sequence set forth in SEQ ID NO:46 (G29K) and the wt counterpart of a Z domain based ligand includes the amino acid sequence set forth in SEQ ID NO:48 (A29K). Further, in case a ligand according to the present invention includes more than one domain, the corresponding wt counterpart will include the same number of domains; however, may include a mutation to alter Fab binding. Accordingly, in certain embodiments, a wt counterpart of a pentameric C domain ligand according to the present invention includes the amino acid sequence set forth in SEQ ID NO: 95 or in SEQ ID NO:96.

The term "sequence identity" means that two nucleotide or amino acid sequences, when optimally aligned, such as by the programs GAP or BESTFIT using default gap weights, share at least 70% sequence identity, or at least 80% sequence identity, or at least 85% sequence identity, or at least 90% sequence identity, or at least 95% sequence identity or more. For sequence comparison, typically one sequence acts as a reference sequence (e.g., parent sequence), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., *Current Protocols in Molecular Biology*). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

As used interchangeably herein, the terms "E domain," "E domain of SpA," and "E domain of *Staphylococcus aureus* Protein A," refer to the polypeptide whose amino acid sequence is set forth in SEQ ID NO:1 or that encoded by, e.g., the nucleotide sequence set forth in SEQ ID NO:7. The "E domain" is a 51 amino acid polypeptide that folds into a three-helix bundle structure. It is capable of binding Fc via residues on the surface of helices 1 and 2, or to Fab via residues on the surface of helices 2 and 3.

As used interchangeably herein, the terms "D domain," "D domain of SpA," and "D domain of *Staphylococcus aureus* Protein A," refer to the polypeptide whose amino acid sequence is set forth in SEQ ID NO:5 or that encoded by e.g., the nucleotide sequence set forth in SEQ ID NO:11. The "D domain" is a 61 amino acid polypeptide that folds into a three-helix bundle structure. It is capable of Fc binding via residues on the surface of helices 1 and 2, or to Fab via residues on the surface of helices 2 and 3.

As used interchangeably herein, the terms "A domain," "A domain of SpA," and "A domain of *Staphylococcus aureus* Protein A," refer to the polypeptide whose amino acid sequence is set forth in SEQ ID NO:2 or that encoded by, e.g., the nucleotide sequence set forth in SEQ ID NO:8. The "A domain" is a 58 amino acid polypeptide that folds into a three-helix bundle structure. It is capable of Fc binding via residues on the surface of helices 1 and 2, or to Fab via residues on the surface of helices 2 and 3.

As used interchangeably herein, the terms "B domain," "B domain of SpA," and "B domain of *Staphylococcus aureus* Protein A," refer to the polypeptide whose amino acid sequence is set forth in SEQ ID NO:3 or that encoded by, e.g., the nucleotide sequence set forth in SEQ ID NO:9. The "B domain" is a 58 amino acid polypeptide that folds into a three-helix bundle structure. It is capable of Fc binding via residues on the surface of helices 1 and 2, or to Fab via residues on the surface of helices 2 and 3.

In some embodiments, a B domain based ligand according to the present invention includes a deletion of three amino acids from the N-terminus, e.g., having the amino acid sequence set forth in SEQ ID NO:13. In other embodiments, a B domain based ligand according to the present invention includes a deletion of four amino acids from the N-terminus, e.g., having the amino acid sequence set forth in SEQ ID NO:28. In another embodiment, a B domain based ligand according to the present invention includes a deletion of five amino acids from the N-terminus (sequence not shown).

As used interchangeably herein, the terms "C domain," "C domain of SpA," and "C domain of *Staphylococcus aureus* Protein A," refer to the polypeptide whose amino acid sequence is set forth in SEQ ID NO:4 or that encoded by, e.g., the nucleotide sequence set forth in SEQ ID NO:10. The "C domain" is a 58 amino acid polypeptide that folds into a three-helix bundle structure. It is capable of Fc binding via residues on the surface of helices 1 and 2, or to Fab via residues on the surface of helices 2 and 3.

In some embodiments, a C domain based ligand according to the present invention includes a deletion of three amino acids from the N-terminus, e.g., having the amino acid sequence set forth in SEQ ID NO:14. In other embodiments, a C domain based ligand according to the present invention includes a deletion of four amino acids from the N-terminus, e.g., having the amino acid sequence set forth in SEQ ID NO:29. In another embodiment, a C domain based ligand according to the present invention includes a deletion of five amino acids from the N-terminus (sequence not shown).

As used interchangeably herein, the terms "Z domain," "Z domain of SpA" and "Z domain of Protein A," refer to the three helix, 58 amino acid polypeptide that is a variant of the B domain of protein A. The amino acid sequence of the Z domain is set forth in SEQ ID NO:6 and the nucleic acid sequence is set forth in SEQ ID NO:12. An exemplary Z domain is described in Nilsson et al., *Protein Engr* 1:107-113 (1987), the entire contents of which are incorporated by reference herein.

In some embodiments, a Z domain based ligand according to the present invention includes a deletion of three amino acids from the N-terminus, e.g., having the amino acid sequence set forth in SEQ ID NO:15. In other embodiments, a Z domain based ligand according to the present invention includes a deletion of four amino acids from the N-terminus, e.g., having the amino acid sequence set forth in SEQ ID NO:30. In another embodiment, a Z domain based ligand according to the present invention includes a deletion of five amino acids from the N-terminus (sequence not shown).

In some embodiments, more than one site of the ligands described herein is attached to a solid support (i.e., multipoint attachment) and where the ligands show reduced fragmentation (in case of both free and attached ligands) during use in purification processes, as evidenced by SDS-PAGE or SEC.

The term "reduced fragmentation," as used herein, refers to a decrease in the number and/or intensity of fragments of a ligand, as seen on an SDS-PAGE gel or by SEC, relative to a wt counterpart of the ligand, following exposure of the free ligand molecule or the ligand molecule immobilized onto a solid support, to alkaline conditions during the purification process. In some embodiments, the ligand is immobilized onto a solid support via multipoint attachment. Fragmentation is usually detected by the presence of lower molecular bands relative to the intact molecule on an SDS-PAGE gel or as distinct peaks having different retention times on an SEC chromatogram.

The SpA ligands according to the present invention exhibit reduced fragmentation, which can be detected as follows. For example, the free ligand can be exposed directly to 0.1M NaOH, 0.3M NaOH or 0.5M NaOH for 25 hrs, followed by a pH adjustment to 7.0 and can be subsequently analyzed by SDS-PAGE or SEC using standard protocols. Alternatively, a ligand immobilized onto a chromatography matrix can be exposed to 0.1M NaOH, 0.3M NaOH or 0.5M NaOH for 25 hrs. The caustic supernatant is subsequently separated from the matrix (e.g., a resin) and neutralized to pH 7. This supernatant can then be analyzed by SDS-PAGE or by SEC using standard protocols. In the case of SDS-PAGE, the relative optical intensity of the fragments can be observed visually and compared to a suitable control (e.g., a wt domain of SpA or an SpA domain containing a mutation at position 29, as described herein). In the case of SEC, the relative peak intensity can be observed and compared to a suitable control (e.g., a wt domain of SpA or an SpA domain containing a mutation at position 29, as described herein).

A typical purification process using an affinity chromatography matrix involves regeneration of the matrix after each cycle of use employing an acidic or an alkaline solution, the latter being preferable. In addition, typical processes also involve CIP steps, which employ use of an acidic or alkaline solution to sanitize the matrix, alkaline solutions being preferable. Accordingly, an affinity chromatography matrix is expected to be exposed to several cycles of regeneration and CIP steps in its lifetime, thereby resulting in a significant loss in binding capacity for a target molecule over time.

The chromatography matrices incorporating the ligands according to the present invention are alkaline stable in addition to exhibiting reduced fragmentation during use in purification processes, in that they show a reduced loss of binding capacity for a target molecule over time, following extended exposure to alkaline conditions during regeneration and CIP steps.

The term "alkaline-stable," "alkaline stability," "caustic stable" or "caustic stability," as used herein, generally refers to the ability of an affinity ligand according to the present invention, either alone or when immobilized onto a chromatography matrix, to withstand repeated regeneration and CIP cycles using alkaline wash without losing its initial binding capacity. In general, it is assumed that a matrix by itself, onto which a ligand according to the invention is immobilized, contributes to less than a 5% change in stability after having been soaked in 0.5M NaOH for up to 30 hours. For example, in some embodiments, affinity ligands according to the invention are able to withstand conventional alkaline cleaning for a prolonged period of time, which renders the ligands attractive candidates, especially for cost-effective large-scale purification of immunoglobulins and Fc-containing proteins, many of which are therapeutic molecules.

In some embodiments, alkaline stability refers to the ability of a ligand according to the present invention or a matrix incorporating a ligand according to the present invention, to retain at least 65%, or at least 70%, or at least 75%, or at least 80%, or at least 85%, or at least 90%, or at least 95% of its initial binding capacity after 5 hours, or after 10 hours, or after 15 hours, or after 20 hours, or after 25 hours, or after 30 hours of incubation in 0.05M NaOH, 0.1M NaOH, 0.3M NaOH or 0.5M NaOH. In another embodiment, alkaline stability refers to a decrease in the initial binding capacity of the ligand by less than 70%, or less than 60%, or less than 50%, or less than 40%, or less than 30% even after treatment with 0.05M NaOH, 0.1M NaOH, 0.3M NaOH or 0.5M NaOH for 5 hours or 7.5 hours or 10 hours or 15 hours or 20 hours or 25 hours or 30 hours. In a particular embodiment, a chromatography matrix incorporating a ligand according to the present invention retains up to 95% of its initial binding capacity after exposure to 0.5M NaOH for 5 hours. In another embodiment, a chromatography matrix incorporating a ligand according to the present invention retains up to 95% of its initial binding capacity after exposure to 0.1M NaOH for 25 hours. In yet another embodiment, a chromatography matrix incorporating a ligand according to the present invention retains up to 85% of its initial binding capacity after exposure to 0.3M NaOH for 25 hours. In a further embodiment, a chromatography matrix incorporating a ligand according to the present invention retains up to 65% of its initial binding capacity after exposure to 0.5M NaOH for 25 hours.

In some embodiments, SpA-based chromatography matrices according to the present invention exhibit an increased or improved alkaline stability as compared to matrices including wild type SpA domains. However, in other embodiments, SpA-based chromatography matrices according to the present invention are not more alkaline stable than the matrices including wild-type counterparts of the ligands. One such example is a ligand based on the pentameric C domain of SpA which is not more alkaline stable than its wild-type pentameric C domain counterpart. It is understood that in certain instances, both the wild-type and the variants of SpA domains may include a G29K mutation to reduce Fab binding; however, such mutation does not itself have an effect on alkaline stability (data not shown).

Alkaline stability can be readily measured by one of ordinary skill in the art using routine experimentation and/or as described herein.

The term "initial binding capacity," as used herein, refers to the amount of a target molecule (e.g., an immunoglobulin or an Fc-containing protein) that can be captured by a unit volume of an affinity chromatography matrix (i.e., a matrix including an affinity ligand) prior to exposure of the matrix to alkaline conditions.

In some embodiments according to the present invention, affinity chromatography matrices including the ligands described herein (i.e., containing one or more SpA B, Z or C domains including N-terminal deletions described herein) exhibit less than 5%, or less than 6%, or less than 7%, or less than 8%, or less than 9%, or less than 10%, or less than 12%, or less than 15%, or less than 17%, or less than 20%, or less than 25%, or less than 30% loss in the initial binding capacity of a target molecule relative to an affinity chromatography matrix containing a corresponding wt SpA domain counterpart, as described herein, following extended exposure to caustic conditions. In some embodiments, the affinity chromatography matrices according to the present invention retain at least 95%, or at least 90%, or at least 85%, or at least 80%, or at least 75%, or at least 70% of the initial binding capacity of a target molecule relative to an affinity chromatography matrix containing a corresponding wt SpA domain counterpart, following extended exposure to caustic conditions. However, in some other embodiments, the chromatography matrices according to the present invention exhibit similar binding capacity to matrices containing wt counterpart of the ligand following extended exposure to caustic conditions. One such exemplary chromatography matrix includes a ligand that includes 5 or more C domains of SpA, where each domain includes 4 amino acids deleted from the N-terminus where the ligand is not more alkaline stable than its wild-type C domain counterpart. Both the deletion form and the wild-type counterpart may contain a G29K mutation. Further, in various embodiments described herein, the SpA ligands may further include a single amino acid such as, an alanine, a valine or a glycine, at the N-terminus of only the first domain in a multimer, where the extra amino acid facilitates homogeneous post-translational processing.

The binding capacity of an affinity chromatography ligand for a target molecule can be readily measured using methods known in the art and those described herein, e.g., as described in U.S. Patent Publication No. 20100221844, incorporated by reference herein in its entirety.

The term "chromatography," as used herein, refers to a dynamic separation technique which separates a target molecule of interest (e.g., an immunoglobulin or an Fc-containing protein) from other molecules in the mixture and allows it to be isolated. Typically, in a chromatography method, a mobile phase (liquid or gas) transports a sample containing the target molecule of interest across or through a stationary phase (normally solid) medium. Differences in partition or affinity to the stationary phase separate the different molecules while mobile phase carries the different molecules out at different time.

The term "affinity chromatography," as used herein, refers to a mode of chromatography where a target molecule to be separated is isolated by its interaction with a molecule (e.g., an alkaline stable chromatography ligand) which specifically interacts with the target molecule. In one embodiment, affinity chromatography involves the addition of a sample containing a target molecule (e.g., an immunoglobulin or an Fc-containing protein) to a solid support which carries on it an SpA-based ligand, as described herein.

The term "Protein A affinity chromatography," as used herein, refers to the separation or isolation of substances using Protein A or SpA-based ligands, such as those described herein, where the SpA or Protein A ligand is immobilized, e.g., on a solid support. Examples of Protein A affinity chromatography media/resin known in the art include those having the Protein A immobilized onto a controlled pore glass backbone, e.g., PROSEP A™ and PROSEP vA™ media/resin (MILLIPORE); those having Protein A immobilized onto a polystyrene solid phase, e.g., the POROS 50A™ and Poros MabCapture A™ media/resin (APPLIED BIOSYSTEMS, INC.); and those having Protein A immobilized on an agarose solid support, e.g., rPROTEIN A SEPHAROSE FAST FLOW™ or MABSELECT™ media or resins (GE HEALTHCARE).

In addition to the aforementioned matrices, Protein A may also be immobilized onto a hydrophilic crosslinked polymer. See, e.g., U.S. Patent Publication No. 20080210615, incorporated by reference herein in its entirety, which describes exemplary hydrophilic crosslinked polymers. Without wishing to be bound by theory, it is contemplated that the ligands encompassed by the present invention may be immobilized onto hydrophilic crosslinked polymers, such as those described in U.S. Patent Publication No. 20080210615.

The term "affinity matrix" or "affinity chromatography matrix," as used interchangeably herein, refers to a chromatographic support onto which an affinity chromatography ligand (e.g., SpA or a domain thereof) is attached. The ligand is capable of binding to a molecule of interest through affinity interaction (e.g., an immunoglobulin or an Fc-containing protein) which is to be purified or removed from a mixture. Exemplary Protein A based affinity chromatography matrices for use in Protein A based affinity chromatography which are known in the art include Protein A immobilized onto a controlled pore glass backbone, e.g., the PROSEP A™ and PROSEP vA™ resins, High Capacity, Ultra and PROSEP Ultra Plus (MILLIPORE); Protein A immobilized on a polystyrene solid phase, e.g. the POROS 50A™ resin and POROS MabCapture A™ (APPLIED BIOSYSTEMS); or Protein A immobilized on an agarose solid phase, for instance the rPROTEIN A SEPHAROSE FAST FLOW™ or MABSELECT™ resin (GE HEALTHCARE).

The term "immunoglobulin," "Ig" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fc and/or Fv fragments.

The term "antigen-binding fragment" refers to a polypeptide portion of an immunoglobulin or antibody that binds an antigen or competes with intact antibody (i.e., with the intact antibody from which they were derived) for antigen binding (i.e., specific binding). Binding fragments can be produced by recombinant DNA techniques, or by enzymatic or chemical cleavage of intact immunoglobulins. Binding fragments include Fab, Fab', F(ab')2, Fv, single chains, and single-chain antibodies.

Also encompassed are fusion proteins including an antibody or fragment thereof as a part of the fusion protein.

The terms "polynucleotide" and "nucleic acid molecule," used interchangeably herein, refer to polymeric forms of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically or biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. A nucleic acid molecule can take many different forms, e.g., a gene or gene fragment, one or more exons, one or more introns, mRNA, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. As used herein, "DNA" or "nucleotide sequence" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. In a particular embodiment, a nucleic acid molecule comprises a nucleotide sequence encoding a variant of SpA, as described herein.

The term "Fc-binding," "binds to an Fc portion" or "binding to an Fc portion" refers to the ability of an affinity ligand described herein, to bind to the constant part (Fc) of an antibody. In some embodiments, a ligand according to the present invention binds an Fc portion of an antibody (e.g., human IgG1, IgG2 or IgG4) with an affinity of at least $10^{-7}$M, or at least $10^{-8}$ M, or at least $10^{-9}$M.

As used herein, the term "Fab binding" or "binding to a Fab portion" refers to the ability of an affinity ligand described herein, to bind to a Fab region of an antibody or an immunoglobulin molecule. The term "reduced binding to a Fab portion" refers to any decrease in binding to a Fab (or $F(ab)_2$) portion of an immunoglobulin molecule by a SpA-based ligand according to the present invention relative to a control (e.g., a wt SpA domain), where the ligand further includes a mutation in one or more amino acids. In some embodiments, a ligand according to the present invention and its wt counterpart (used as a control) includes the glycine residue at position 29 replaced with an amino acid other than alanine or tryptophan. In a particular embodiment, a ligand according to the present invention includes a lysine residue at position 29. In a particular embodiment, binding to a Fab portion of an immunoglobulin molecule by a ligand described herein is undetectable using conventional techniques in the art and those described herein. Binding to an immunoglobulin molecule can be detected using well known techniques including those described herein and including but not limited to, for example, affinity chromatography and surface plasmon resonance analysis. In some embodiments, an immunoglobulin binding protein encompassed by the present invention binds an immunoglobulin molecule with an affinity of at least $10^{-10}$M.

The term "N-terminus," as used herein, refers to amino-terminus of the amino acid sequence of a SpA domain, starting at position 1 or at position 2 of the amino acid sequence of each of the domains, as depicted in FIG. 1. However, it is understood that the first amino acid in a sequence may be preceded by a methionine amino acid residue or another amino acid to facilitate homogenous post translational processing of the protein such as, for example, an alanine, a glycine or a valine. The SpA ligands described herein include a deletion of at least 3, or at least 4, or at least 5 consecutive amino acids from the N-terminus (starting at position 1 or at position 2 of B, C or Z domain amino acid sequences shown in FIG. 1) of a SpA domain. In other words, such ligands include a deletion of consecutive amino acids 1 through 3, or consecutive amino acids 1 through 4, or consecutive amino acids 1 through 5 etc., of SpA domains B, Z or C or such ligands include a deletion of consecutive amino acids 2 through 4, or consecutive amino acids 2 through 5, or consecutive amino acids 2 through 6 etc., of SpA domains B, Z or C (amino acid sequences of wt B, C and Z domains are depicted in FIG. 1, which are modified to include deletions from the N-terminus). In a particular embodiment, a ligand according to the present invention includes 5 C domains, with each domain including a deletion of 4 consecutive amino acids from the N-terminus, starting at position 1.

The amino acid sequence of the B domain of SpA containing a deletion of 3 consecutive amino acids from the N-terminus is depicted in SEQ ID NO:13, and that containing a deletion of 4 consecutive amino acids from the N-terminus is depicted in SEQ ID NO: 28. Additionally, the amino acid sequence of the C domain of SpA containing a deletion of 3 consecutive amino acids from the N-terminus is depicted in SEQ ID NO: 14; and that containing a deletion of 4 consecutive amino acids from the N-terminus is depicted in SEQ ID NO: 29. Further the amino acid sequence of the Z domain containing a deletion of 3 consecutive amino acids from the N-terminus is depicted in SEQ ID NO:15; and that containing a deletion of 4 consecutive amino acids from the N-terminus is depicted in SEQ ID NO: 30.

In general, in case of multimeric forms of SpA-based ligands described herein, the amino acid sequences of the monomeric forms of the ligands are simply repeated, as desirable. However, it is to be noted that, in case of some multimeric forms of ligands according to the present invention, not all domains need to have a deletion from the N-terminus. For example, in some embodiments, ligands do not contain a deletion in the N-terminus of the first domain in the multimeric form of ligand; however, subsequent domains in the ligand contain a deletion of at least 3 consecutive amino acids from the N-terminus or at least 4 consecutive amino acids from the N-terminus or at least 5 consecutive amino acids from the N-terminus.

The SpA-based ligands according to the present invention harbor superior and unexpected properties, i.e., reduced fragmentation during use in purification processes, as evidenced by the Examples herein. Notably, the teachings in the prior art appear to teach away from the motivation to make and use such ligands. For example, U.S. Patent Publication No. 20100048876, discusses a ligand which includes a deletion in amino acid residues 3 through 6 of the C domain of SpA; however, based on the teachings of this publication (see, e.g., FIG. 2 of U.S. Patent Publication No. 20100048876), it appears that the deletion mutant described therein performs poorly with respect to retention of binding capacity relative to the wt C domain of SpA, over extended caustic exposure. Accordingly, based on the teachings of this reference, it would be less desirable to use a deletion mutant of a SpA C domain, when it loses more binding capacity over time, relative to its wild-type counterpart.

For the sake of convenience, the various sequences referenced through the application are summarized in Table I below.

TABLE I

| Brief Description of Sequence | SEQ ID NO: |
|---|---|
| wt E domain AA | 1 |
| wt A domain AA | 2 |
| wt B domain AA | 3 |
| wt C domain AA | 4 |
| wt D domain AA | 5 |
| Z domain AA | 6 |
| wt E domain NA | 7 |
| wt A domain NA | 8 |
| wt B domain NA | 9 |
| wt C domain NA | 10 |
| wt D domain NA | 11 |
| Z domain NA | 12 |
| B domain Δ 3 AA monomer | 13 |
| C domain Δ 3 AA monomer | 14 |
| Z domain Δ 3 AA monomer | 15 |
| B domain Δ 3 AA dimer-both domains having deletion | 16 |
| C domain Δ 3 AA dimer-both domains having deletion | 17 |
| Z domain Δ 3 AA dimer-both domains having deletion | 18 |
| B domain Δ 3 AA dimer-only second domain has deletion | 19 |
| C domain Δ 3 AA dimer-only second domain has deletion | 20 |
| Z domain Δ 3 AA dimer-only second domain has deletion | 21 |
| B domain Δ 3 AA pentamer-all domains have deletion | 22 |
| C domain Δ 3 AA pentamer-all domains have deletion | 23 |
| Z domain Δ 3 AA pentamer-all domains have deletion | 24 |
| B domain Δ 3 AA pentamer-first domain does not have deletion | 25 |
| C domain Δ 3 AA pentamer-first domain does not have deletion | 26 |
| Z domain Δ 3 AA pentamer-first domain does not have deletion | 27 |
| B domain Δ 4 AA monomer | 28 |
| C domain Δ 4 AA monomer | 29 |
| Z domain Δ 4 AA monomer | 30 |
| B domain Δ 4 AA dimer-both domains having deletion | 31 |
| C domain Δ 4 AA dimer-both domains having deletion | 32 |
| Z domain Δ 4 AA dimer-both domains having deletion | 33 |
| B domain Δ 4 AA dimer-only second domain has deletion | 34 |
| C domain Δ 4 AA dimer-only second domain has deletion | 35 |
| Z domain Δ 4 AA dimer-only second domain has deletion | 36 |
| B domain Δ 4 AA pentamer-all domains have deletion | 37 |
| C domain Δ 4 AA pentamer-all domains have deletion | 38 |
| Z domain Δ 4 AA pentamer-all domains have deletion | 39 |
| B domain Δ 4 AA pentamer-first domain does not have deletion | 40 |
| C domain Δ 4 AA pentamer-first domain does not have deletion | 41 |
| Z domain Δ 4 AA pentamer-first domain does not have deletion | 42 |
| wt E domain AA non-Fab (G29K) | 43 |
| wt A domain AA non-Fab (G29K) | 44 |
| wt B domain AA non-Fab (G29K) | 45 |
| wt C domain AA non-Fab (G29K) | 46 |
| wt D domain AA non-Fab (G29K) | 47 |
| Z domain AA non-Fab (A29K) | 48 |
| wt E domain NA non-Fab (G29K) | 49 |
| wt A domain NA non-Fab (G29K) | 50 |
| wt B domain NA non-Fab (G29K) | 51 |
| wt C domain NA non-Fab (G29K) | 52 |
| wt D domain NA non-Fab (G29K) | 53 |
| Z domain NA non-Fab (A29K) | 54 |
| B domain Δ 3 AA monomer non-Fab (G29K) | 55 |
| C domain Δ 3 AA monomer non-Fab (G29K) | 56 |
| Z domain Δ 3 AA monomer non-Fab (A29K) | 57 |
| B domain Δ 3 AA dimer-both domains having deletion non-Fab (G29K) | 58 |
| C domain Δ 3 AA dimer-both domains having deletion non-Fab (G29K) | 59 |

TABLE I-continued

| Brief Description of Sequence | SEQ ID NO: |
|---|---|
| Z domain Δ 3 AA dimer-both domains having deletion non-Fab (A29K) | 60 |
| B domain Δ 3 AA dimer-only second domain has deletion non-Fab (G29K) | 61 |
| C domain Δ 3 AA dimer-only second domain has deletion non-Fab (G29K) | 62 |
| Z domain Δ 3 AA dimer-only second domain has deletion non-Fab (A29K) | 63 |
| B domain Δ 3 AA pentamer-all domains have deletion non-Fab (G29K) | 64 |
| C domain Δ 3 AA pentamer-all domains have deletion non-Fab (G29K) | 65 |
| Z domain Δ 3 AA pentamer-all domains have deletion non-Fab (A29K) | 66 |
| B domain Δ 3 AA pentamer-first domain does not have deletion non-Fab (G29K) | 67 |
| C domain Δ 3 AA pentamer-first domain does not have deletion non-Fab (G29K) | 68 |
| Z domain Δ 3 AA pentamer-first domain does not have deletion non-Fab (A29K) | 69 |
| B domain Δ 4 AA monomer non-Fab (G29K) | 70 |
| C domain Δ 4 AA monomer non-Fab (G29K) | 71 |
| Z domain Δ 4 AA monomer non-Fab (A29K) | 72 |
| B domain Δ 4 AA dimer-both domains having deletion non-Fab (G29K) | 73 |
| C domain Δ 4 AA dimer-both domains having deletion non-Fab (G29K) | 74 |
| Z domain Δ 4 AA dimer-both domains having deletion non-Fab (A29K) | 75 |
| B domain Δ 4 AA dimer-only second domain has deletion non-Fab (G29K) | 76 |
| C domain Δ 4 AA dimer-only second domain has deletion non-Fab (G29K) | 77 |
| Z domain Δ 4 AA dimer-only second domain has deletion non-Fab (A29K) | 78 |
| B domain Δ 4 AA pentamer-all domains have deletion non-Fab (G29K) | 79 |
| C domain Δ 4 AA pentamer-all domains have deletion non-Fab (G29K) | 80 |
| Z domain Δ 4 AA pentamer-all domains have deletion non-Fab (A29K) | 81 |
| B domain Δ 4 AA pentamer-first domain does not have deletion non-Fab (G29K) | 82 |
| C domain Δ 4 AA pentamer-first domain does not have deletion non-Fab (G29K) | 83 |
| Z domain Δ 4 AA pentamer-first domain does not have deletion non-Fab (A29K) | 84 |
| Z domain dimer non-Fab (A29K) | 85 |
| His tag NA | 86 |
| Z Domain Δ 1 AA dimer-first domain does not have deletion non-Fab (A29K) | 87 |
| Z DomainΔ 2 AA dimer-first domain does not have deletion non-Fab (A29K) | 88 |
| A Domain Δ 4 AA dimer-first domain has a N-terminal deletion | 89 |
| D Domain Δ 4 AA dimer-first domain has a N-terminal deletion | 90 |
| Z domain pentamer non-Fab (A29K) | 91 |
| C domain dimer AA | 92 |
| C domain Δ 4 AA pentamer with the first domain having N-terminus alanine non-Fab (G29K) | 93 |
| C domain Δ 4 AA pentamer with the first domain with N-terminus alanine | 94 |
| C domain pentamer non-Fab (G29K) AA | 95 |
| C domain pentamer wild type AA | 96 |

AA—Amino Acid; NA—Nucleic Acid; Δ—having a deletion

II. Generation of SpA-Based Molecules for Use as Chromatography Ligands

The SpA-based affinity chromatography ligands encompassed by the present invention can be made using any suitable methods known in the art.

For example, as an initial step, standard genetic engineering techniques, e.g., those described in the laboratory manual entitled Molecular Cloning by Sambrook, Fritsch and Maniatis, may be used for the generation of nucleic acids which express the SpA ligand molecules described herein.

In some embodiments, a nucleic acid molecule encoding one or more domains of SpA having an N-terminus deletion can be cloned into a suitable vector for expression in an appropriate host cell. Suitable expression vectors are well-known in the art and typically include the necessary elements for the transcription and translation of the variant SpA coding sequence.

SpA molecules described herein may also be synthesized chemically from amino acid precursors for fragments using methods well known in the art, including solid phase peptide synthetic methods such as the Boc (tert-butyloxycarbonyl) or Fmoc (9-fluorenylmethyloxy carbonyl) approaches (see, e.g., U.S. Pat. Nos. 6,060,596; 4,879,378; 5,198,531; 5,240,680).

Expression of SpA molecules described herein can be accomplished in a variety of cells types such as, e.g., eukaryotic host cells such as yeast cells, insect cells and mammalian cells and prokaryotic host cells, e.g., bacteria such as E. coli.

In some embodiments, SpA molecules may be expressed on the surface of a bacteriophage such that each phage contains a DNA sequence that codes for an individual SpA molecule displayed on the phage surface. The affinity of the SpA molecule for an immunoglobulin can be readily assayed for using standard techniques in the art and those described herein, e.g., ELISA and Biacore™ 2000 standard set up (BIACORE AB, Uppsala Sweden). It is desirable that the binding affinity of a SpA molecule of the present invention to an immunoglobulin is at least comparable with that of the parent molecule, where the molecule exhibits reduced fragmentation during use, as described herein.

III. Supports Used for the Preparation of Chromatography Matrices

In some embodiments, SpA ligands encompassed by the present invention are immobilized onto a support, e.g., a solid support or a soluble support, to generate an affinity chromatography matrix suitable for the separation of biomolecules such as, e.g., immunoglobulins and Fc-containing proteins.

In some embodiments, a ligand according to the present invention is immobilized onto a solid support. Without wishing to be bound by theory, it is contemplated that any suitable solid support may be used for the attachment of a ligand according to the invention. For example, solid support matrices include, but are not limited to, controlled pore glass, silica, zirconium oxide, titanium oxide, agarose, polymethacrylate, polyacrylate, polyacrylamide, polyvinylether, polyvinyl alcohol and polystyrene and derivatives thereof (e.g., alloys thereof). A solid support may be a porous material or a non-porous material.

In some embodiments, a solid support is a porous material. A porous material used as a solid support may be comprised of a hydrophilic compound, a hydrophobic compound, an oleophobic compound, an oleophilic compound or any combination thereof. The porous material may be comprised of a polymer or a copolymer. Examples of suitable porous materials, include, but are not limited to polyether sulfone, polyamide, e.g., nylon, polysaccharides such as, for example, agarose and cellulose, polyacrylate, polymethacrylate, polyacrylamide, polymethacrylamide, polytetrafluoroethylene, polysulfone, polyester, polyvinylidene fluoride, polypropylene, polyethylene, polyvinyl alcohol, polyvinylether, polycarbonate, polymer of a fluorocarbon, e.g. poly(tetrafluoroethylene-co-perfluoro(alkyl vinyl ether)), glass, silica, zirconia, titania, ceramic, metal and alloys thereof.

The porous material may be comprised of an organic or inorganic molecule or a combination of organic and inorganic molecules and may be comprised of one or more functional groups, e.g., a hydroxyl group, an epoxy group, a thiol group, an amino group, a carbonyl group, or a carboxylic acid group, suitable for reacting, e.g., forming covalent bonds for further chemical modification, in order to covalently bind to a protein. In another embodiment, the porous material may not possess a functional group but can be coated with a layer of material that bears functional groups such as, a hydroxyl group, a thiol group, an amino acid group, a carbonyl group, or a carboxylic acid group.

In some embodiments, a conventional affinity separation matrix is used, e.g., of organic nature and based on polymers that expose a hydrophilic surface to the aqueous media used, i.e. expose hydroxy (—OH), carboxy (—COOH), carbonyl (—CHO, or RCO—R'), carboxamido (—CONH$_2$, possibly in N-substituted forms), amino (—NH$_2$, possibly in substituted form), oligo- or polyethylenoxy groups on their external and, if present, also on internal surfaces. In one embodiment, the polymers may, for instance, be based on polysaccharides, such as dextran, starch, cellulose, pullulan, agarose etc, which advantageously have been cross-linked, for instance with bisepoxides, epihalohydrins, allyl bromide, allyglycidyl ether, 1,2,3-trihalo substituted lower hydrocarbons, to provide a suitable porosity and rigidity. In another embodiment, the solid support comprises porous agarose beads. The various supports used in the present invention can be readily prepared according to standard methods known in the art, such as, for example, inverse suspension gelation described, e.g., in Hjerten, *Biochim Biophys Acta* 79(2), 393-398 (1964). Alternatively, the base matrices can be commercially available products, such as Sepharose™ FastFlow (GE HEALTHCARE, Uppsala, Sweden). In some embodiments, especially advantageous for large-scale separations, the support is adapted to increase its rigidity, and hence renders the matrix more suitable for high flow rates.

Alternatively, the solid support can be based on synthetic polymers, such as polyvinyl alcohol, polyvinylether, polyhydroxyalkyl acrylates, polyhydroxyalkyl methacrylates, polyacrylamides, polymethacrylamides etc. In case of hydrophobic polymers, such as matrices based on divinyl and monovinyl-substituted benzenes, the surface of the matrix is often hydrophilized to expose hydrophilic groups as defined above to a surrounding aqueous liquid. Such polymers can be easily produced according to standard methods, see e.g., Arshady, *Chimica e L'Industria* 70(9), 70-75 (1988). Alternatively, a commercially available product, such as Source™ (GE HEALTHCARE, Uppsala, Sweden) and Poros (APPLIED BIOSYSTEMS, Foster City, Calif.) may be used.

In yet other embodiments, the solid support comprises a support of inorganic nature, e.g. silica, zirconium oxide, titanium oxide and alloys thereof. The surface of inorganic matrices is often modified to include suitable reactive groups for further reaction to SpA and its variants. Examples include CM Zirconia (Ciphergen—BioSepra (CERGYPONTOISE, France) and CPG® (MILLIPORE).

In some embodiments, the solid support may, for instance, be based on zirconia, titania or silica in the form of controlled pore glass, which may be modified to either contain reactive groups and/or sustain caustic soaking, to be coupled to ligands.

Exemplary solid support formats include, but are not limited to, a bead (spherical or irregular), a hollow fiber, a solid fiber, a pad, a gel, a membrane, a cassette, a column, a chip, a slide, a plate or a monolith.

With respect to the format of a matrix, in one embodiment, it is in the form of a porous monolith, which may be made using an inorganic material such as, e.g., silica, or an organic material such as, e.g. polymethacrylate, polyacrylate, polyacrylamide, polymethacrylamide, polytetrafluoroethylene, polysulfone, polyester, polyvinylidene fluoride, polypropylene, polyethylene, polyvinyl alcohol, polyvinylether and polycarbonate. In case of a monolith, it may be formed via polymerization or by coating a substrate.

In an alternative embodiment, the matrix is in beaded or particle form that can be porous or non-porous. Particles may be spherical or non-spherical as well as magnetic or non-magnetic. Matrices in beaded or particle form can be used as a packed bed or in a suspended form. Suspended forms include those known as expanded beds and pure suspensions, in which the particles or beads are free to move. In case of monoliths, packed bed and expanded beds, the separation procedure commonly follows conventional chromatography with a concentration gradient. In case of pure suspension, batch-wise mode will be used. Also, solid support in forms such as a surface, a chip, a capillary, or a filter may be used.

The matrix could also be in the form of membrane in a cartridge. The membrane could be in flat sheet, spiral, or hollow fiber format.

In another embodiment, a ligand according to the present invention is attached to a soluble support, e.g., a soluble polymer or a water soluble polymer. Exemplary soluble supports include, but are not limited to, a bio-polymer such as, e.g., a protein or a nucleic acid. In some embodiments, biotin maybe used as a soluble polymer, e.g., as described in US Patent Publication No. 20080108053. For example, biotin may be bound to a ligand, e.g., a SpA-based ligand according to the present invention, which subsequent to being bound to the ligand, can be used for isolating a protein of interest, e.g., an antibody or fragment thereof, e.g., present in a crude mixture and the protein of interest can be isolated or separated via precipitation of the biotin-ligand-protein polymer complex in either a reversible or irreversible fashion. The polymer may also be a synthetic soluble polymer, such as, for example, including but not limited, to a polymer containing negatively charged groups (carboxylic or sulfonic), positively charged groups (quarternary amine, tertiary amine, secondary or primary groups), hydrophobic groups (phenyl or butyl groups), hydrophilic groups (hydroxyl, or amino groups) or a combination of the above. Exemplary synthetic soluble polymers can be found in International PCT Publication No. WO2008091740 and U.S. Publication No. US20080255027, the entire teachings of each of which are incorporated by reference herein. These polymers, upon specific physical changes in one or more conditions such as pH, conductivity or temperature, can be used to purify the protein of interest via precipitation in either a reversible or an irreversible fashion. Synthetic soluble polymers may be used alone or may be coupled with a ligand according to the present invention and used for capture/purification of a protein of interest such as, e.g., an antibody or a fragment thereof, via precipitation in either a reversible or an irreversible fashion.

In some embodiments, ligands are attached to a membrane in a multi-well plate format. In yet other embodiments, the ligands are incorporated into a capillary or a microfluidics device.

IV. Methods for Attaching a Ligand to a Support

Any suitable technique may be used for attaching a ligand described herein to a support, e.g., a solid support including those well-known in the art and described herein. For example, in some embodiments, the ligand may be attached to a support via conventional coupling techniques utilizing, e.g. amino and/or carboxy groups present in the ligand. For example, bisepoxides, epichlorohydrin, CNBr, N-hydroxysuccinimide (NHS) etc., are well-known coupling reagents. In some embodiments, a spacer is introduced between the support and the ligand, which improves the availability of the ligand and facilitates the chemical coupling of the ligand to the support.

In various embodiments encompassed by the present invention, more than one site on a ligand is attached to a solid support such (i.e., via multipoint attachment), thereby resulting in an affinity chromatography matrix which shows reduced fragmentation of the ligand upon extended caustic exposure (both in case of the free ligand as well as the attached ligand).

Attachment of a SpA-based chromatography ligand to a solid support can be achieved via many different ways known, most of which are well known in the art, as well as those described herein. See, e.g., Hermanson et al., *Immobilized Affinity Ligand Techniques*, Academic Press, pp. 51-136 (1992).

For example, protein ligands can be coupled to a solid support via active groups on either the surface of the solid support or the protein ligand, such as, for example, hydrolxyl, thiol, epoxide, amino, carbonyl, epoxide, or carboxylic acid group. Attachment can be achieved using known chemistries including, but not limited to, use of cyanogen bromide (CNBr), N-hydroxyl succinimide ester, epoxy (bisoxirane) activation, and reductive amination.

For example, thiol-directed protein coupling has been described in the literature. See, e.g., Ljungquist, et al. *Eur. J. Biochem.* Vol 186, pp. 558-561 (1989). This technique has been previously applied for coupling SpA to a solid support. Since wild type SpA does not contain thiol groups, the attachment is achieved by recombinantly inserting a thiol containing cysteine at the C-terminus of SpA. See, e.g., U.S. Pat. No. 6,399,750. Several commercial products such as MabSelect™, MabSelect™ Xtra and MabSelect™ SuRe, MabSelect™ SuRe LX are produced via this mechanism. It has been reported that this terminal cysteine only reacts with the epoxide group on the solid surface, thereby resulting in single point attachment of the SpA to the solid support. See, e.g., *Process Scale Bioseparations for the Biopharmaceutical Industry*, CRC Press, 2006, page 473.

In some embodiments according to the present invention, more than one site on the SpA-based chromatography ligands is attached to a solid support via non-discriminate, multipoint attachment. In general, SpA contains abundant free amino groups from numerous lysines in each domain. The attachment of a SpA domain to a solid support via multipoint attachment, e.g., a chromatography resin with epoxide or aldehyde group, can be achieved by reacting the amino group of lysine on SpA, via epoxide ring-opening or reductive amination, respectively. In certain embodiments, multipoint attachment can be achieved by the reaction of one or more naturally occurring amino acids on SpA having free hydroxyl groups, such as, for example, serine and tyrosine, with a support containing an epoxide group via a ring-opening reaction. Alternatively, multipoint attachment can be achieved, for example, by the reaction of naturally occurring amino acids on SpA having free carboxylic acid groups, such as, for example, aspartic acid and glutamic acid, with a support containing amino groups via, for example, N,N'-carbonyldiimidazole. Multipoint attachment of the ligand to support can also be achieved by a combination of all the above mechanisms.

SpA-based chromatography ligands may also be attached to a solid support via an associative mechanism. For example, an associative group may interact with a ligand of interest non-covalently via ionic, hydrophobic or a combination of interactions, thereby to attach ligand of interest onto the solid surface. This facilitates the high efficiency coupling of ligand to the solid matrix, for example, as described in U.S. Pat. Nos. 7,833,723 and 7,846,682, incorporated by reference herein, thereby resulting in ligand density higher than that without the associative groups. Associative groups suitable for use in the invention include charged species such as ionic species, and uncharged species such as hydrophobic species. The associative group may modify the solid support, e.g. by covalently binding directly with the solid support. Suitable examples of ionic species may include quaternary amines, tertiary amines, secondary amines, primary amines, a sulfonic group, carboxylic acid, or any combination thereof. Suitable examples of hydrophobic species may include a phenyl group, a butyl group, a propyl group, or any combination thereof. It is also contemplated that mixed mode species may be used. The associative group may also interact with the protein ligand. Thus the interaction between the associative group and the protein ligand may be comprised of a mixture of interactions, e.g. ionic and hydrophobic species.

The associative group may be covalently coupled to the solid support by reacting a functional group on the solid support with a functional group on the associative group. Suitable functional groups include, but are not limited to, amines, hydroxyl, sulfhydryl, carboxyl, imine, aldehyde, ketone, alkene, alkyne, azo, nitrile, epoxide, cyanogens and activated carboxylic acid groups. As an example, agarose beads contain hydroxyl groups which may be reacted with the epoxide functionality of a positively charged associative group, such as glycidyl trimethylammonium chloride. A skilled artisan will appreciate that a plurality of associative groups may be coupled to the solid support provided that at least one bifunctional associative group is used. Thus associative groups may be coupled in tandem to the solid support or they may be individually coupled directly to the solid support.

In some embodiments, the present invention provides associative groups and/or protein ligands which may be coupled to a solid support via an intervening linker. The linker may comprise at least one functional group coupled to a linking moiety. The linking moiety may comprise any molecule capable of being coupled to a functional group. For example, the linking moiety may include any of an alkyl, an alkenyl, or an alkynyl group. The linking moiety may comprise a carbon chain ranging from 1 to 30 carbon atoms. In some embodiments the linker may be comprised of more than 30 carbon atoms. The linking moiety may comprise at least one heteroatom such as nitrogen, oxygen and sulfur. The linking moiety may be comprised of a branched chain, an unbranched chain or a cyclic chain. The linking moiety may be substituted with two or more functional groups.

Choosing the appropriate buffer conditions for coupling a protein ligand to a solid support is well within the capability of the skilled artisan. Suitable buffers include, e.g., sodium acetate, sodium phosphate, potassium phosphate, sodium carbonate, sodium bicarbonate, potassium carbonate, potassium bicarbonate, sodium chloride, potassium chloride, sodium sulphate, etc, or any combination of the above, with the concentration ranging from 10 mM to 5M. In some embodiments, the concentration of salt ranges from 0.1M to 1.5M.

Additional suitable buffers include any non-amine containing buffer such as carbonate, bicarbonate, sulfate, phosphate and acetate buffers, or a combination of the above. When associative chemistry is used, salt concentration of the buffer will depend on the associative group used. For example, the salt concentration may be in the range of 5 nM-100 mM. Where a charged species is used, the salt concentration may be at least 5 nM but less than 0.1M, at least 5 nM but less than 0.01M, at least 5 nM but less than 0.001M. In certain embodiments, the salt concentration may be 0.01M. Where a hydrophobic species is used a high salt concentration is usually desirable. Thus the salt concentration may be greater than 0.001M, greater than 0.01M, or greater than 0.1M.

In some embodiments, when associative chemistry is used, the reaction is performed at a temperature ranging from 0° C. to 99° C. In certain embodiments the reaction method is practiced at a temperature less than 60° C., less than 40° C., less than 20° C., or less than 10° C. In some embodiments the method of the invention is practiced at a temperature of about 4° C. In other embodiments the method of the invention is practiced at a temperature of 20° C.

V. Assaying for Reduced Fragmentation of the Ligands

The present invention provides affinity chromatography matrices which incorporate SpA ligands based on one or more B, Z or C domains, where one or more domains include a deletion of 3 or 4 or 5 consecutive amino acids from the N-terminus, starting at position 1 or at position 2. In some embodiments, more than one site on an SpA-based ligand is attached to a chromatography matrix.

The present invention is based on an unexpected and surprising discovery that the ligands described herein, both in free form as well as when immobilized onto a solid support (e.g., a chromatography matrix), exhibit reduced fragmentation following exposure to extended caustic conditions during use in purification processes. As discussed above, such fragmentation is undesirable as it leads to potentially immunogenic fragments of SpA domains ending up with the potentially therapeutic target protein. Further the fragmentation makes the purification process more costly due to the need to use more ligand during the process.

Fragmentation of affinity ligands can be readily detected using methods known in the art and those described herein. Such methods include, but are not limited to, SDS-PAGE and SEC.

Sodium dodecyl sulfate (SDS)-polyacrylamide gel electrophoresis (PAGE) is commonly used for molecular weight analysis of proteins. SDS is a detergent that dissociates and unfolds proteins. The SDS binds to the polypeptides to form complexes with fairly constant charge to mass ratios. The electrophoretic migration rate through a gel is therefore determined only by the size of the complexes. Molecular weights are determined by simultaneously running marker proteins of known molecular weight. The gel is typically stained and the presence of biomolecules of different molecular weights can be visualized.

Size-exclusion chromatography (SEC) is a method in which molecules in solution are separated by their size. It is usually applied to large or macromolecular complexes such as proteins and industrial polymers. Detection of different molecular species is typically performed by UV-Vis or by light scattering. In the case of UV-Vis, a wavelength specific for detection of certain species is chosen. The orders in which certain molecular species elute, as observed on the chromatogram, as well as the intensity of corresponding peaks, provides information on the species type as well as relative quantity.

As demonstrated by the examples included herein, the SpA ligands according to the present invention exhibit reduced fragmentation relative to their wt counterparts, following exposure to caustic conditions. In an exemplary experiment to show reduced fragmentation, a SpA ligand having an N-terminus deletion, as described herein, and its wt counterpart, are both exposed to 0.5M NaOH for 25 hrs. The solution is then neutralized with an acid to pH 7. The neutralized solutions are injected into SEC or loaded on to an SDS-PAGE gel for analysis and comparison.

In another exemplary experiment to show reduced fragmentation, an affinity chromatography matrix including a ligand having an N-terminus deletion attached to a solid support (immobilized via multipoint attachment), as described herein, as well as an affinity chromatography matrix including its wt counterpart attached to a solid support (immobilized via multipoint attachment), are both exposed to 0.5M NaOH for 25 hrs. The caustic solution and the matrix (e.g., in the form of a resin) are separated and immediately neutralized with an acid to pH 7. The neutralized solutions are injected into SEC or loaded on to an SDS-PAGE gel for analysis and comparison.

VI. Assaying for Alkaline Stability of the Ligands

In addition to exhibiting reduced fragmentation during use in purification processes, the ligands described herein are also alkaline stable. Subsequent to the generation of the chromatography matrices incorporating the SpA-based ligands described herein, the alkaline stability of the matrices containing the ligands can be assayed using standard techniques in the art and those described herein.

For example, the alkaline stability of a ligand immobilized onto a matrix can be assayed using routine treatment with NaOH at a concentration of about 0.5M, e.g., as described herein as well as in U.S. Patent Publication No. 20100221844, the entire content of which is incorporated by reference herein in its entirety.

In some embodiments, alkaline stable SpA molecules as well as matrices incorporating the same exhibit an "increased" or "improved" alkaline stability, meaning that the molecules and matrices incorporating the same are stable under alkaline conditions for an extended period of time relative to their wt counterparts. Previously, it has been reported that chromatography matrices incorporating SpA ligands based on the wt B, C or Z domain of SpA or having a mutation of one or more asparagine residues provides an improved alkaline stability under conditions where the pH is above about 10, such as up to about 13 or 14. However, some of these ligands appear to show fragmentation during use, especially following repeated cycles of CIP, as observed by the presence of fragments on an SDS-PAGE gel or by SEC.

In some embodiments, ligands according to the present invention as well as matrices incorporating the same are no more alkaline stable than their wt counterparts; nonetheless, they exhibit reduced fragmentation. One such ligand described herein is a pentameric form of the C domain ligand including an N-terminus deletion in each of the domains and including a G29K mutation in each of the domains. Such a ligand may further include an alanine as the very first amino acid in the pentamer to facilitate homogenous post-translational processing.

The present invention is based on the surprising and unexpected discovery of novel SpA ligands (in both free form as well as well when immobilized into a chromatography matrix) which exhibit reduced fragmentation during use in purification processes relative to some of the previously described ligands, in addition to retaining at least 95% of the initial binding capacity following extended exposure to caustic conditions (e.g., 0.1M NaOH for 25 hours or more). In some embodiments, more than one site on the ligands is attached onto a solid support and these ligands are based on B, C, or Z domains of SpA, where the ligands have a deletion of 3, 4 or 5 consecutive amino acids from the N-terminus, starting at position 1 or at position 2.

In some embodiments, after 100 cycles, each cycle including a 15 min treatment with 0.5M NaOH, the percentage of retained binding capacity of the SpA ligands described herein (e.g., those comprising one or more B, C or Z domains, and any combinations thereof, where at least one of B, C or Z domain includes a deletion of at least 3 consecutive amino acids from the N-terminus), is at least 1.25 times more, 1.5 times more, 2.0 times more, 2.5 times more, or 3 times more than that of the wt counterpart.

In one embodiment, the alkaline stability of the immobilized ligand, as assayed by the retention of IgG binding capacity over time, is measured as follows. The binding capacity, referred to as Qd 50%, is measured by obtaining the volume of IgG loaded to a concentration based on absorbance at $UV_{280\ nm}$ of 50% of the initial IgG concentration. The initial Qd 50% of the chromatography matrix (e.g., resin packed in a column) is measured first. The chromatography matrix (e.g., resin as described above) is then exposed to about 10 cycles of 15 min exposure of 0.5M NaOH at 0.8 mL/min. Qd 50% is measured again. This process is repeated until the chromatography matrix is exposed to a total of about 100 cycles of 0.5M NaOH. Qd 50% is measured one last time and the results from the affinity chromatography matrix including ligands (e.g., chromatography resin immobilized with ligands) as described herein are compared with the respective type wt domains of SpA.

In another assay, caustic or alkaline stability of the matrix is measured by static soaking of the matrix. By soaking a measured amount of an affinity chromatography matrix (e.g., in resin format) in 0.1M NaOH, 0.3M NaOH or 0.5M NaOH for 25 hrs with gentle rotation and measuring IgG binding capacity before and after the NaOH soaking, the alkaline stability by way of retention of binding capacity of the matrix for IgG, can be determined.

VII. Methods of Purifying a Target Molecule Using a Chromatography Matrix of the Invention In some embodiments, the present invention provides a method of purifying a target molecule from a mixture using the affinity chromatography matrices described herein. The target molecule may be any molecule which is recognized by an affinity ligand provided herein, where the ligand is coupled to a solid support (i.e., a chromatography matrix). Examples of target molecules include immunoglobulins and Fc-containing proteins. The immunoglobulins may be polyclonal antibodies or a monoclonal antibody or a functional fragment thereof. Functional fragments include any fragment of an immunoglobulin comprising a variable region that still binds specifically to its antigen while at the same time retaining its ability to specifically bind to a protein ligand coupled to a solid support.

In some embodiments, a method of isolating a target molecule of interest using an affinity chromatography matrix described herein includes the steps of: (a) contacting a solid support including an immobilized SpA-based chromatography ligand having an amino acid sequence selected from the group consisting of SEQ ID NOs: 13-42, SEQ ID NOs: 55-84 and SEQ ID NOs: 93-95, with a mixture comprising a target molecule under conditions such that the target molecule specifically binds to the ligand; and (b) altering the conditions such that the target molecule is no longer bound to the ligand, thereby isolating the target molecule.

In some embodiments, the altering step includes altering the pH, such the target molecule is no longer bound to the ligand. In a particular embodiment, the pH is altered in a manner such that it is more acidic than the pH conditions in step (a). For example, in one embodiment, step (a) may be performed at a neutral pH, or a pH ranging from about 6 to about 8 and step (b) may be performed at an acidic pH, e.g., a pH ranging from about 1 to about 5.

In another embodiment, step (b) comprises altering the salt concentration of the buffer in use, such that the target molecule is no longer bound to the ligand. For example, in one embodiment, a high salt concentration, e.g., >0.1M, may be used in step (a) and a lower salt concentration, e.g., <0.1M may be used in step (b). Conversely, in some embodiments, a low salt concentration, e.g., <0.1M may be used in step (a) and a high salt concentration may be used in step (b). In still other embodiments, both the pH and the salt concentration of the buffer may be altered between step (a) and step (b).

One skilled in the art can readily determine the conditions suitable for binding a target molecule to a ligand, and thereby alter the conditions to disrupt the binding of the molecule to the ligand.

In general, it is contemplated that the ligands described herein can be used in any purification process or a purification process train where native SpA and recombinant SpA are typically used. In other words, it is generally desirable to replace the native SpA (e.g., isolated from *S. aureus*) and recombinant SpA (e.g., recombinantly expressed wt SpA) in the current processes in the art with the ligands described herein, in order to reduce overall cost as well as mitigate the risk of potentially immunogenic SpA fragments co-purifying with a potential therapeutic molecule.

In some embodiments, the present invention relates to a method of purification of antibodies by affinity chromatography, where the method includes the following steps: contacting a process feed with an affinity chromatography matrix according to the invention in order to bind one or more antibodies in the feed; an optional wash step; adding a suitable elution buffer for releasing the bound antibodies from the matrix; and recovering the one or more antibodies from the eluate. The affinity chromatography matrices described herein may also be used for isolating antibodies from culture liquids, supernatants as well as fermentation broths. In case of fermentation broths, the use of affinity chromatography matrices enables the separation of antibodies from host cell proteins (HCPs), DNA, viruses, endotoxins, nutrients, one or more components of a cell culture medium, e.g., antifoam agents and antibiotics, and product-related impurities, such as misfolded species and aggregates.

In a specific embodiment, the feed is subjected to mechanical filtration before it is contacted with the affinity chromatography matrix described herein, and consequently the mobile phase is a clarified cell culture broth. Suitable conditions for adsorption are well known to those of skill in the art.

In another embodiment, the present invention relates to a multi-step process for the purification of antibodies, which process comprises a capture step using an affinity chromatography matrix described herein followed by one or more subsequent steps for intermediate purification and/or polishing of the antibodies. In a particular embodiment, the capture step is followed by hydrophobic interaction and/or ion exchange chromatography and/or weak partition chromatography in bind- and elute or flow through mode. In an alternative step, the capture step is followed by multimodal anion or cation exchange chromatography and/or weak partition chromatography in bind-and-elute or flow through mode.

In another embodiment, any leached SpA-based ligand from the affinity chromatography matrix can be removed by the subsequent purification steps to acceptable levels e.g., to levels deemed acceptable for native Protein A ligand.

In general, it is contemplated that the ligands described herein may be used in any process which typically employs Protein A ligands.

This invention is further illustrated by the following examples which should not be construed as limiting. The contents of all references, patents and published patent applications cited throughout this application, as well as the Figures, are incorporated herein by reference.

EXAMPLES

Example 1

Generation of SpA Ligands with One or More Domains Having an N-Terminus Deletion of 4 Consecutive Amino Acids Synthetic genes encoding the following proteins were obtained from DNA 2.0 (Menlo Park, Calif.). A SpA dimeric protein containing two Z domains, each domain containing the mutation at position 29 (A29K) to reduce or eliminate Fab binding (amino acid sequence shown in SEQ ID NO: 85); and a SpA dimeric protein containing two Z domains, each domain containing the A29K mutation and the second Z domain containing a deletion to delete 4 consecutive amino acids from the N-terminus (amino acid sequence shown in SEQ ID NO:78).

The 5' end of each synthetic gene includes a codon for an initiating methionine and the 3' end includes six histidine codons (SEQ ID NO:86) for subsequent purification using NiNTA column. The 5' and 3' ends of each gene contain NdeI and BamHI restriction sites, respectively. These synthetic genes as well as the expression vector that is used, i.e., pET11a (EMD), are digested with NdeI and BamHI (NEW ENGLAND BIOLABS, Ipswich, Mass.), the DNA fragments are separated on a 0.7% agarose TAE gel and the appropriate DNA fragments are excised and purified using the gel extraction kit from QIAGEN (Valencia, Calif.). The purified inserts are ligated into the backbone of a pET11a or any other suitable expression vector using T4 DNA ligase (NEW ENGLAND BIOLABS, Ipswich, Mass.).

The ligation reaction is transformed into DH5α competent E. coli (INVITROGEN, Carlsbad, Calif.), as per manufacturer's instructions, and plated on Technova LB plates containing 100 µg/mL ampicillin and grown overnight at 37° C. In order to obtain purified DNA, individual colonies are picked for overnight culture in LB containing 100 µg/mL ampicillin. DNA is purified using spin mini-prep kits from QIAGEN (Valencia, Calif.). The identity of recombinant plasmids is confirmed by restriction digest analysis using NdeI and BamHI (NEW ENGLAND BIOLABS, Ipswich, Mass.). Plasmid maps for the plasmids including both inserted genes for the Z domain dimeric constructs are shown in FIG. 2.

Additionally, constructs expressing a pentameric form of SpA ligand containing 5 Z domains, each domain containing the A29K mutation (amino acid sequence set forth in SEQ ID NO:91); as well as a pentameric form of SpA ligand containing 5 Z domains, with each domain containing the A29K mutation as well as all but the first domains containing a deletion of 4 consecutive amino acids from the N-terminus (amino acid sequence set forth in SEQ ID NO:84), are generated.

Further, dimeric SpA ligand constructs containing C domains are also generated. A dimeric construct expressing a C domain ligand is generated, the amino acid sequence of which is set forth in SEQ ID NO:92; as well as a dimeric construct expressing a 2 C domain ligand is generated, where only the second C domain includes a deletion of 4 consecutive amino acids from the N-terminus, the amino acid sequence of which is set forth in SEQ ID NO:35. These C domain dimeric ligands do not have a mutation at position 29.

Example 2

Expression and Purification of SpA-Based Ligands

As discussed above, any suitable bacterial expression system can be used for expressing the various SpA ligands described herein. For example, the protein may be expressed in an *Escherchia coli* strain such as strain BL21(DE3) (PROMEGA, Madison Wis.) using a pET vector such as pET11a (EMD).

A single colony is selected from a plate and grown overnight at 37° C. in LB media containing 100 µg/mL ampicillin. The overnight culture is diluted 100-fold into fresh LB media containing 100 µg/mL ampicillin and grown to a cell density such that the optical density at 600 nm is ~0.8. Following the addition of 1 mM isopropyl-beta-D-thiogalactopyranoside, cells are grown for an additional two hours. Expression is confirmed by SDS-PAGE analysis and Western blotting.

Cells are harvested by centrifugation (4000 rpm, 4° C., 5 minutes) and resuspended in 3 mL of phosphate buffered saline containing 20 mM imidazole. Cells are lysed by sonication, and cell debris is pelleted by centrifugation (4000 rpm, 4° C., 30 minutes). SpA ligands are purified using NiNTA resin (QIAGEN), applying 25-30 mL cell lysate per 3-mL column. Columns are washed with 30 mL phosphate buffered saline containing 20 mM imidazole twice, and SpA is eluted in 3 mL fractions of phosphate buffered saline containing 200 mM imidazole. SpA is dialyzed overnight into 18 mega-Ohm Milli-Q® water (MILLIPORE, Billerica, Mass.) followed by 10 mM NaHCO$_3$. Protein concentration is confirmed using the UV spectrometer based on theoretical extinction coefficient (Pace et. al., Protein Science 4:2411 (1995)).

Example 3

Attachment of SpA-Based Ligands to a Solid Support

Subsequent to the generation and expression of various ligands, as described in Examples 1 and 2, they were immobilized via multipoint attachment to a solid support.

In an exemplary experiment, agarose resin (Sepharose 4B) (GE HEALTHCARE) is crosslinked using epichlorohydrin according to a previously described method (Porath and Fornstedt, *J. Chromatography,* 51:479 (1979)). The agarose resin is subsequently reacted with positively charged associative groups, e.g., cations, according to the following method: to 10 mL of resin, 5 mL of 75% wt glycidyl trimethylammonium chloride (GTMAC), 5 mL Milli-Q® water (MILLIPORE, Billerica, Mass.) and 0.258 g 50 wt sodium hydroxide is added. The reaction vial is rotated in a Techne HB-1D hybridizer (BIBBY SCIENTIFIC, Burlington, N.J.) overnight at room temperature. The resin is then filtered and washed with three 10-mL volumes of Milli-Q® water (MILLIPORE, Billerica, Mass.).

The resin (10 mL, filtered cake) is added to a jar containing 3 mL of 4.6M NaOH. The mixture is slurried and then 4 mL of butanediol diglycidylether (BUDGE) is added. This mixture is rotated at 35° C. for about 2 hours. The resin is then washed with 5×10 mL of Milli-Q® water (MILLIPORE, Billerica, Mass.) and equilibrated with 2×10 mL of 10 mM NaHCO$_3$.

Immediately following the BUDGE activation step above, to 5 mL of the filtered bead cake, 10 mL solution of 10 mM NaHCO$_3$ containing a 2.5 and 2.3 mg/mL concentration of dimeric Z domain ligand containing A29K mutation (SEQ ID:85) or the dimeric Z domain ligand containing N-terminus deletion in the second Z domain (SEQ ID:78), is added. The mixture is capped in a glass vial and the vial is rotated at 37° C. for about 2 hours. After two hours, the resin is washed with 3 times with 10 mL of Milli-Q® water. The filtered bead cake (10 mL) is added to a jar containing a 10 mL solution comprised of 1 mL of thioglycerol and 9 mL of a buffer solution with 0.2M NaHCO$_3$ and 0.5M NaCl. The mixture is slurried and rotated overnight at room temperature. The resin is then washed with 3 times with 10 mL of the following buffers: 0.1M Tris buffer with 0.15M NaCl (pH 8) and 50 mM acetic acid (pH 4.5). This is followed by rinsing the resin with 10 mL of Milli-Q® water and 10 mL of 20% ethanol water solution (v/v). The final resin is stored in 20% alcohol water solution (v/v) before further use. The method of coupling the dimeric C domain ligands to a solid support is similar to what is described herein for the dimeric Z domain ligands.

Method of coupling of 5 domain ligands described above (SEQ ID NOs: 91 and 84) to agarose base resin is similar to the process above, except that 15 mg/mL of ligand is used during the coupling step. The Z domain pentameric ligands do not contain a His-6 tag.

Example 4

SDS-PAGE Analysis of Supernatants Collected after Caustic Soak of Free or Immobilized Ligands SDS-PAGE analysis can be used for detecting fragmentation of free and immobilized ligands described herein, following extended caustic exposure. An SDS-PAGE protocol is described below.

SpA in Milli-Q® water, neutralized caustic soaked ligand solution, and neutralized resin soak solutions (each contains ~0.5 mg/mL of protein) are diluted at 1:1 ratio with Laemmli buffer (BIORAD, Hercules, Calif.). Samples are incubated at 70° C. for 5 minutes to ensure proteins were fully denatured. 10 µL of each sample is loaded to AnyKD gel (BIORAD, Hercules, Calif.) or 15% Tris-HCl Ready gel (BIORAD, Hercules, Calif.). Gel electrophoresis is conducted in 1× Tris-Glycine-SDS running buffer (THERMOFISHER, Waltham, Mass.) at 200 volts for 30 minutes. SDS-Gel is then stained in Gelcode Blue stain reagent (THERMOFISHER, Waltham, Mass.) for 1 hour and destained in Milli-Q® water overnight.

Example 5

SEC Analysis of Supernatants Collected after Caustic Soak of Free or Immobilized Ligands In addition to SDS-PAGE analysis described above, SEC (size exclusion chromatography) can also be used for fragmentation analysis of the free and immobilized ligands following extended caustic soak. An SEC experiment is described below.

SEC is conducted on an Agilent 1100 HPLC system (AGILENT, Santa Clara, Calif.). SpA control in Milli-Q® water, neutralized caustic soaked ligand solution (~0.5 mg/mL), and neutralized resin soak solutions are centrifuged at 13500 RPM for 10 minutes prior to SEC-HPLC analysis. Samples are injected in 20 µL onto the SEC column (SEPAX Zenix 7.8 mm×300 mm, SEPAX TECHNOLOGIES, INC. Newark, Del.). Sodium phosphate buffer (200 mM, pH 7.0) is used as mobile phase with flow rate of 1 mL/min. ChemStation software from Agilent is used for SEC data acquisition and analysis at both 230 nm and 280 nm.

Example 6

Caustic Soak of Ligands

Following the expression of the ligands, as described in Example 2, the ligands are exposed to alkaline conditions.

To 1 mL of each of the ligands described above (at a concentration of 1 mg/mL), 1 mL of 1M NaOH is added to a final concentration of 0.5M NaOH and 0.5 mg/mL ligand. The sample is gently rotated for 25 hrs. This solution is then neutralized to pH~7 using 32 µL of glacial acetic acid.

The fragmentation analysis of the Z domain and C domain dimeric ligands using SDS-PAGE following with and without caustic soak, is shown in FIG. 3. As observed in FIG. 3, the dimeric Z domain ligand (A29K with no deletions, shown in SEQ ID NO:85, which is used as the control) shows significant fragmentation following caustic soak in 0.5M NaOH for 25 hours, as demonstrated by the presence of a smear as well as presence of smaller fragments at around 7 KDa (see Lane 3). In contrast, the dimeric Z domain ligand having the A29K mutation as well as a deletion of 4 consecutive amino acids in the second domain (amino acid sequence of SEQ ID NO:78) appears to be largely intact following caustic soak in 0.5M NaOH for 25 hours (see Lane 6).

Similarly, the dimeric C domain ligand having no deletions (the amino acid sequence set forth in SEQ ID NO:92, used as a control) shows the presence of a smear as well as smaller fragments around 7 KDa on an SDS-PAGE following caustic soak in 0.5M NaOH for 25 hours (see Lane 9) relative to the dimeric C domain construct which includes a deletion of 4 consecutive amino acid deletion from the N-terminus of the second domain, the amino acid sequence of which is set forth in SEQ ID NO:35 (see Lane 12).

Each of the dimeric Z and C domain ligands additionally includes a His-6 tag. The ligands that are not exposed to caustic soak are shown in Lane 2 (dimeric Z domain control), Lane 5 (dimeric Z domain ligand having a N-terminus deletion), Lane 8 (dimeric C domain control) and Lane 9 (dimeric C domain ligand having a N-terminus deletion).

Reduced fragmentation of the dimeric Z and C domain ligands having an N-terminus deletion, following extended caustic soak, is further evidenced by SEC. The results of a representative SEC experiment are shown in FIG. 4 in the form of an SEC chromatogram. As seen in FIG. 4, the controls for the Z domain ligand (having the amino acid sequence set forth in SEQ ID NO:85) as well as the C domain ligand (having the amino acid sequence set forth in SEQ ID NO:92) show significant fragmentation, identified by arrows on the chromatogram in FIG. 4. In contrast, the dimeric Z and C domain ligands having the N-terminus deletions in the second domain (Z domain ligand amino acid sequence is set forth in SEQ ID NO:78 and the C domain ligand amino acid sequence is set forth in SEQ ID NO:35), show reduced fragmentation, as identified by boxes on the chromatogram in FIG. 4.

Additionally, the pentameric forms of Z domain ligands described above (i.e., pentameric Z domain ligand having the amino acid sequence of SEQ ID NO:91 which represents the control, and pentameric Z domain ligand having the amino acid sequence of SEQ ID NO:84, which represents the pentameric ligand having a 4 consecutive amino acid N-terminus deletion in all but the first domain) are also analyzed for fragmentation by SDS-PAGE, following caustic soak in 0.5M NaOH for 25 hours.

As evidenced by the SDS-PAGE gel data seen in FIG. 5, the pentameric form of the Z domain ligand having a 4 consecutive amino acid deletion from the N-terminus in all but the first domain (the amino acid sequence of which is set forth in SEQ ID NO:84), shows far less fragmentation following ligand soak in 0.5M NaOH for 25 hours (see Lane 3), relative to the pentameric Z domain ligand control, the amino acid sequence of which is set forth in SEQ ID NO:91 (see Lane 6). As discussed above, both forms of pentameric ligands have the A29K mutation. The ligands that are not soaked appear to be intact (Lanes 2, and 5).

Lanes 8-10 depict the fragmentation observed with a recombinant SpA ligand (rSPA), which is routinely used in purification processes. The rSPA ligand appears to show an even far greater degree of fragmentation following caustic soak in 0.5M NaOH for 25 hours relative to the Z domain control, as observed by a near disappearance of the protein on the SDS-PAGE (see Lane 9). The rSPA ligand not exposed to caustic conditions is in Lane 8.

This result appears to suggest that the Z domain based ligands having the N-terminus deletion, as described herein, are far superior candidates than the routinely used SpA ligands such as, e.g., rSPA.

A reduction in fragmentation following caustic soak in 0.5M NaOH for 25 hours observed with the pentameric Z domain ligand having the N-terminal deletion is further confirmed using SEC, the results of one such representative experiment are shown in FIG. 6.

As demonstrated by the chromatogram in FIG. 6, the pentameric form of the Z domain control (SEQ ID NO:91) with no amino acid deletion shows well resolved peaks at lower molecular weight, indicating the presence of smaller fragments. In contrast, the pentameric form of the Z domain having the N-terminus deletion (SEQ ID NO: 84) shows significantly fewer distinct peaks at lower intensity, indicating a far less degree of fragmentation, relative to the control.

The routinely used SPA ligand, rSPA, shows the most fragmentation or breakdown with no intact molecule left at all. Notably, the SEC chromatogram is consistent with the results of the SDS-PAGE analysis in FIG. 5, further evidencing that the rSPA ligand has degraded so much that no significant fragments can be observed on an SEC chromatogram following extended exposure to caustic conditions (i.e., soaking in 0.5M NaOH for 25 hours).

Example 7

Caustic Soak of Ligands Immobilized on Resin

The various ligands described in the foregoing examples are evaluated for fragmentation following caustic exposure subsequent to their attachment to a solid support (e.g., an agarose chromatography resin).

For each resin of interest, 1 mL resin in 5 mL disposable chromatography column (EVERGREEN SCIENTIFIC, Los Angeles, Calif.) is measured using Milli-Q® water. The resin is conditioned in a column with 2 CV (2 mL) of 0.5M NaOH quickly, re-slurried and vacuumed. After repeating the NaOH condition one more time, the vacuumed wet cake of resin is transferred to 4 mL test tubes (THERMOFISHER, Waltham, Mass.). 2 mL of 0.5M NaOH is added to the column (bottom is capped) and immediately transferred into the test tube with the corresponding resin. Place capped test tubes onto a rotator and rotate the test tubes for 25 hrs. At the end of the caustic soak, content in the test tubes is poured into a disposable column and the filtrate is collected. Filtrate in 1.5 mL is neutralized with 50 µL of glacial acidic acid and is ready for further analysis by SEC and SDS-PAGE.

The SDS-PAGE analysis of the immobilized dimeric Z and C domain ligands following extended caustic soak (e.g., 0.5M NaOH soak for 25 hours) is shown in FIG. 3. In general, it is expected that if a ligand is caustic stable following its immobilization onto a chromatography matrix (e.g., an agarose resin), that it will not show any significant fragmentation.

As observed by the SDS-PAGE gel of FIG. 3, both the dimeric Z and C domain ligands immobilized controls (amino acid sequences set forth in SEQ ID NO:85 and 92, respectively and represented by Lanes 4 and 10 of the SDS-PAGE gel, respectively) as well as the dimeric Z and C domain immobilized ligands containing an N-terminus deletion in the second domain (amino acid sequences set forth in SEQ ID NO:78 and 35, respectively and represented by Lanes 7 and 13, respectively), do not appear to show any detectable fragmentation following 0.5M NaOH soak for 25 hours, implying that they are both caustic stable.

The SDS-PAGE analysis of the immobilized pentameric Z domain ligands following extended caustic soak (e.g., 0.5M NaOH soak for 25 hours) is shown in FIG. 5. As observed by the SDS-PAGE gel in FIG. 5, the pentameric Z domain ligand containing an N-terminus deletion in all but the first domain (amino acid sequence set forth in SEQ ID NO:84, and represented by Lane 4 of the SDS-PAGE gel), shows far less fragmentation as compared to its type wt pentameric Z domain control (SEQ ID NO:91 and Lane 7). This result suggests that the immobilized pentameric Z domain ligand having the N-terminus deletions is more caustic stable compared to the immobilized pentameric Z domain which does not have such deletions.

Further, the fragmentation of a routinely used ligand (i.e., rSPA) is also investigated by SDS-PAGE following its immobilization on an agarose chromatography resin and subjecting the resin with the ligand to an extended soak in 0.5M NaOH for 25 hours. As seen in Lane 10 of the SDS-PAGE gel of FIG. 5, the immobilized rSPA shows significant fragmentation following 0.5M NaOH soak for 25 hours, implying that it is not very caustic stable, relative to the pentameric Z domain ligands (Lanes 4 and 7).

Based on the SDS-PAGE gel results on FIG. 5, it can be concluded that the immobilized pentameric Z domain ligand with the N-terminus deletions has the least fragmentation following extended caustic exposure, and therefore, is most caustic stable, as compared to the immobilized pentameric Z domain control ligand and the immobilized rSPA.

Further confirmation of the SDS-PAGE results with the immobilized pentameric Z domain ligands and the rSPA ligand is obtained by SEC analysis. The results of a representative experiment are depicted in the chromatogram shown in FIG. 7. As seen in FIG. 7, the immobilized Z domain ligand of SEQ ID NO:84 shows reduced fragmentation following extended caustic soak, as shown by a box, relative to its wt counterpart of SEQ ID NO:91, which shows resolved lower molecular weight peaks on the chromatogram. Further, as expected, the immobilized rSPA shows extensive fragmentation following extended caustic soak as observed by broad and unresolved peaks on the chromatogram.

Example 8

Measurement of Static Binding Capacity of Chromatography Matrices to an Immunoglobulin Before and after Exposure to 0.5M NaOH for 25 Hours

The affinity chromatography matrices (i.e., resins having the immobilized resins thereon via multipoint attachment) described above are further tested for their static binding capacity before and after exposure to 0.5M NaOH for 25 hours.

In one experiment, each of the chromatography matrices (in 1 mL volume) immobilized with the dimeric or pentameric Z or C domain ligands described above, either with exposure to 0.1, 0.3 or 0.5M NaOH or without exposure to NaOH, is made into 10% slurry in Milli-Q® water (MILLIPORE, Billerica, Mass.). 1 mL of each slurry is added to 15 mL of polyclonal IgG (SERACARE, 1 mg/mL)) in 10 mM phosphate saline buffer and rotated for 4 hours at room temperature. The reduction of UV at 280 nm is used to calculate capacity before and after caustic binding capacity. The percentage of retained IgG binding capacity is calculated by dividing the IgG binding capacity after caustic exposure by that without caustic exposure. Table II summarizes the results of one such experiment. As summarized in Table II, the dimeric Z domain ligand of SEQ ID NO:78 appears to exhibit a higher retained binding capacity relative to its wt counterpart (i.e., the dimeric Z domain ligand of SEQ ID NO:85), following extended caustic soak in 0.5M NaOH for 25 hours.

Similarly, as also summarized in Table II below, the dimeric C domain ligand of SEQ ID NO:35 appears to exhibit a higher retained binding capacity than its wt counterpart of SEQ ID NO:92, following extended caustic soak in 0.5M NaOH for 25 hours.

TABLE II

| Sequence of Ligand immobilized on matrix | Retained IgG static binding capacity of matrix (%) |
|---|---|
| SEQ ID NO: 85 | 64 |
| SEQ ID NO: 78 | 70 |
| SEQ ID NO: 92 | 65 |
| SEQ ID NO: 35 | 70 |

In a further experiment, the IgG binding capacity of a pentameric Z domain ligand is evaluated following extended caustic soak in 0.1M NaOH, 0.3M NaOH or 0.5M NaOH for 25 hours. The results of one such experiment are summarized in Table III below.

Table III shows the percentage of retained IgG binding capacity of a matrix having immobilized thereon a pentameric form of Z domain ligand which contains an A29K mutation and all but the first domain include a deletion of four consecutive amino acids from the N-terminus (amino acid sequence shown in SEQ ID NO: 84), after soaking the matrix in 0.1M NaOH, 0.3 M NaOH or 0.5M NaOH. As summarized below, the matrix with the pentameric Z domain N-terminus deletion ligand shows up to 95% of the initial binding capacity after 0.1M NaOH soak for 25 hours; up to 85% of the initial binding capacity after 0.3M NaOH soak for 25 hours and up to 65% of the initial binding capacity after 0.5M NaOH soak for 25 hours.

| NaOH concentration (M) | Retained IgG static binding capacity of matrix immobilized with SEQ ID 84 (%) |
|---|---|
| 0.1 | 95 |
| 0.3 | 85 |
| 0.5 | 65 |

Example 9

SpA Capture of IgG Before and after Exposure to 0.5M NaOH

In this experiment, purification of a polyclonal immunoglobulin in null CHO-S feed using a matrix immobilized with a pentamer of Z domain ligand with all but the first domain having a 4 consecutive amino acid deletion is examined along with that having a recombinantly synthesized SpA (rSPA) in order to demonstrate that the ligands according to the present invention work just as well as the recombinant SpA in removing impurities.

Resin samples immobilized with rSPA (REPLIGEN, Waltham, Mass.), and the Z domain pentameric ligand (amino acid sequence shown in SEQ ID NO:84), are each packed into a chromatography column with 1 cm diameter and 5 cm packed bed height. After equilibration with phosphate saline buffer (10 mM sodium phosphate), the packed resins are subjected to exposure of null CHO feed with polyclonal hIgG (SERACARE, 5 mg/mL) at a flow rate of 50 cm/hr. After loading at 90% of 5% breakthrough, the resin is washed with PBS buffer and 50 mM NaOAc, pH 5.5. The bound IgG is subsequently eluted with 50 mM NaOAc, pH 3. Fractions are collected and analyzed for impurity analysis. The packed resin is then exposed to 0.5M NaOH for 15 minutes (flow rate 100 cm/hr) before contacting again with polyclonal hIgG in null CHO feed. Resins are then washed with PBS buffer and 50 mM NaOAc, pH 5.5 and IgG is eluted for further assay.

This caustic exposure and feed run cycle is repeated to collect enough IgG for the subsequent cation exchange step. Leached protein A is quantified using n-Protein A ELISA (REPLIGEN, Waltham, Mass.) according to instructions from the manufacturer. Host cell protein is detected using the 3G CHO HCP ELISA kit (CYGNUS TECHNOLOGIES, Southport, N.C.), as per the manufacturer's instructions. DNA is detected using Quant-iT™ PicoGreen dsDNA Reagent (LIFE TECHNOLOGIES, Foster City, Calif.). The results of one such representative experiment are shown in Table IV.

Example 10

Clearance of Leached SpA Ligands and Further Removal of DNA and Host Cell Protein Using Cation Exchange and Anion Exchange Chromatography

The clearance of the leached ligands as well as further removal of host cell proteins (HCP) and DNA from the elution pool of chromatography affinity matrices incorporating either the SpA ligands according to the present invention or those containing recombinant SpA, rSPA (REPLIGEN, Waltham, Mass.), is examined as follows.

Combination of elution pools from several repetitions of the experiment described in Example 8 provides the feed for further clearance of leached ligands and other impurities using cation exchange chromatography.

Fractogel SO$_3^-$ (MILLIPORE, Billerica, Mass.) is packed into a column with bed dimension of 1.0 cm (i.d.)×7 cm (bed height). The column is equilibrated with 50 mM NaOAc pH 4.5, 4 mS/cm and loaded with the pooled IgG from Protein A elution at 140 cm/hr. After column wash with EQ buffer, IgG is eluted with 0.5N NaCl in 50 mM NaOAc over 20 column volume (linear gradient). The elution pools are collected in 10 mL fractions and analyzed for leached ligands, DNA, and host cell protein.

The fractions from Fractogel SO$_3^-$ column are further pooled and adjusted to pH 7.6 at 12 mS/cm. This feed is loaded onto a pre-equilibrated (Tris, 25 mM, pH 7.6, ~1 mS/cm) ChromaSorb device (0.08 mL, MILLIPORE, Billerica, Mass.) at flow rate of 1 mL/min. Fractions are collected for every 187 column volume and further analyzed for leached ligand and host cell protein, as described in Example 8.

As summarized in Table IV below, both the leached rSPA ligand as well as the pentameric form of Z domain with all but the first domain having a N-terminus deletion of four consecutive amino acids (amino acid sequence set forth in SEQ ID:84), can be cleared to less than 1 PPM after cation exchange and anion exchange chromatography. In addition, the removal of host cell proteins and DNA meets industry standard and is more or less equivalent in both cases, as also summarized in Table below.

TABLE IV

| Ligand on resin | | rSPA | SEQ ID: 84 |
|---|---|---|---|
| Leached Protein A (PPM) | Protein A pool | 7.1 | 3.8 |
| | Cation exchange pool | 1.1 | 1.1 |
| | Anion exchange pool(@ 1g/mL loading) | 0.6 | 1.0 |
| Host cell proteins (PPM) | Feed | 25568 | 25568 |
| | Protein A pool | 232 | 133 |
| | Cation exchange pool | 49 | 60 |
| | Anion exchange pool (@ 1g/mL loading) | 3 | 7 |
| DNA (PPM) | Feed | 6.8 | 6.8 |
| | Protein A pool | 0.05 | 0.04 |
| | Cation exchange pool | 0.03 | 0.03 |
| | Anion exchange pool(@ 1g/mL loading) | Below detection limit | Below detection limit |

Example 11

Effect of the Number of N-Terminus Amino Acid Deletions on Fragmentation of Ligand Following Extended Caustic Soak In another experiment, 1, 2, 3 or 4 amino acid residues were deleted from the N-terminus of the second domain of a dimeric Z domain ligand, starting at position 1, and the effect of the 1, 2, 3 or 4 amino acid deletions on the fragmentation of the ligand following extended caustic soak was determined, as compared to the control dimeric Z domain ligand (A29K)

The results of one such experiment are depicted in the chromatogram shown in FIG. 8. As demonstrated in FIG. 8, the effect on fragmentation of the number of amino acid residues that were deleted from the N-terminus of the second domain of the dimeric Z domain ligand can be observed following extended caustic soak of each of the ligands in 0.5M NaOH for 25 hours followed by SEC analysis, as described in Example 5.

After soaking the ligands in 0.5M NaOH for 25 hours, each of the control ligand (SEQ ID NO:85), the ligand with only the first amino acid deleted from the N-terminus of the second domain (SEQ ID NO:87), and the ligand with the first two amino acids deleted from the N-terminus of the second domain (SEQ ID NO:88) shows fragments at lower molecular weight, as depicted by the arrows, evidencing fragmentation. Whereas, the ligand with the first three amino acids deleted from the N-terminus of the second domain (SEQ ID NO:69) and the ligand with the first four amino acids deleted from the N-terminus of the second domain (SEQ ID NO:78) showed significantly reduced fragmentation at lower molecular weight as depicted by boxes in the chromatogram, evidencing a reduced fragmentation.

These results suggest that the affinity ligands based on one or more domains of Protein A and having at least 3 amino acids deleted from the N-terminus of one or more domains exhibit reduced fragmentation following extended caustic exposure and accordingly, are superior candidates for use as affinity chromatography ligands.

Example 12

Retained Binding Capacity Comparison of N-Terminus Deletion and Wild Type C Domain Pentamers, Both Having a Non-Fab Mutation (G29K)

In this experiment, the retained binding capacity of two C domain pentameric ligands immobilized onto a polyvinyl alcohol based chromatography matrix is examined, one ligand having an N-terminus deletion (starting at position 1) of 4 amino acids in each of the 5 domains, an alanine as the very first amino acid of the pentameric sequence in order to facilitate homogeneous post-translational processing as well as the G29K mutation (the amino acid sequence of which is shown in SEQ ID NO:93) and the other ligand corresponding to its wt counterpart with the G29K mutation (the amino acid sequence of which is shown in SEQ ID NO:95).

The ligands are immobilized onto polyvinyl alcohol based affinity chromatography resins via multipoint attachment (see, e.g., Hermanson et al., *Immobilized Affinity Ligand Techniques, Academic Press*, pp. 51-136 (1992)), and tested for retained dynamic binding capacity upon repeated NaOH exposure.

In one experiment, the chromatography matrices are packed into columns (0.66 cm i.d.×1.0 cm bed height) and are subjected to a standard chromatographic run with equilibration followed by application of 30 mg polyclonal human IgG (hIgG) at 60 cm/hr. After extensive washing-out of unbound proteins with equilibration buffer (10 mM phosphate buffer saline), bound IgG is eluted with elution buffer (0.1M citric acid, pH 3) at 60 cm/hr. This is followed by Cleaning-In-Place (CIP) with 0.7M NaOH for 30 mins. The column is re-equilibrated and the run is repeated for 16 more times (a cumulative exposure to 0.7M NaOH for 8 hrs). Retained binding capacity is measured by determining total amount of eluted IgG (elution volume multiplied by IgG concentration measured at UV$_{280}$) over time. Relative retained capacity is plotted against the first run with 0 min exposure to NaOH and is shown in FIG. 9. This experiment is repeated 3 times with similar results. As demonstrated in FIG. 9, both C domain pentameric ligands, with and without the deletion, show similar retained binding capacity following extended exposure to NaOH over time. Further, in another experiment, retained binding capacity of the C domain pentameric ligand without the alanine and having the G29K mutation (amino acid sequence of which is shown in SEQ ID NO:80) is compared to its wt counterpart with the G29K mutation (amino acid sequence of which is shown in SEQ ID NO:95), with a similar result (data not shown).

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

---

What is claimed is:

1. An affinity chromatography ligand comprising two or more B domains or two or more C domains or two or more Z domains of *Staphylococcus aureus* Protein A (SPA), wherein each domain has a deletion of 3 or 4 consecutive amino acids from the N-terminus, starting at position 1 or position 2 corresponding to its wild type counterpart, wherein the ligand is immobilized onto a solid support and wherein the ligand exhibits reduced fragmentation following exposure of the ligand to 0.5 M NaOH for at least 5 hours, as evidenced by SDS-PAGE and/or SEC techniques, relative to its wildtype counterpart.

2. The affinity chromatography ligand of claim 1, wherein the ligand is immobilized onto a solid support via multipoint attachment.

3. The affinity chromatography ligand of claim 1, wherein the immobilized ligand retains at least 95% of its initial binding capacity for a target molecule after 5 hours, or after 10 hours, or after 15 hours, or after 20 hours, or after 25 hours, or after 30 hours of incubation in 0.5 M NaOH.

4. The affinity chromatography ligand of claim 1, wherein the ligand further comprises replacement of a glycine amino acid residue at position 29 with a lysine amino acid residue in case of B domain and C domain, or replacement of an alanine residue at position 29 with a glycine residue, in case of Z domain.

5. The affinity chromatography ligand of claim 2, wherein the solid support is selected from the group consisting of controlled pore glass, silica, zirconium oxide, titanium oxide, agarose, polymethacrylate, polyacrylate, polyacrylamide, polyvinylether, polyvinyl alcohol and polystyrene and derivatives thereof.

6. The affinity chromatography ligand of claim 1, wherein the solid support is selected from a bead, a hollow fiber, a solid fiber, a pad, a gel, a membrane, a cassette, a column, a chip, a slide, a plate or a monolith.

7. The affinity chromatography ligand of claim 1, wherein the solid support is a bead comprising polyvinylether.

8. A method of purifying a target molecule from a sample, the method comprising the steps of:
   (a) providing a sample comprising an immunoglobulin;
   (b) contacting the sample with a chromatography ligand of claim 1 under conditions such that the target molecule binds to the ligand;
   (c) altering conditions such that the target molecule is no longer bound to the ligand,
   thereby to purify the target molecule from the sample.

9. The method of claim 8, wherein the target molecule is an immunoglobulin.

10. The method of claim 9, wherein the immunoglobulin is a monoclonal antibody.

11. The method of claim 8, wherein the altering step includes altering the pH, such the target molecule is no longer bound to the ligand.

12. The method of claim 8, wherein, the pH is altered in step (c) such that it is more acidic than the pH in step (a).

13. The method of claim 8, further comprising one or more subsequent purification or polishing steps.

14. The method of claim 13, wherein the one or more subsequent purification or polishing steps are selected from one or more of hydrophobic interaction chromatography, ion exchange chromatography and weak partition chromatography.

15. The method of claim 14, wherein the one or more subsequent purification or polishing steps are carried out in a flow-through mode.

* * * * *

SEQUENCE LISTING

```
<160> NUMBER OF SEQ ID NOS: 97

<210> SEQ ID NO 1
<211> LENGTH: 51
<212> TYPE: PRT
<213> ORGANISM: Staphylococcus aureus

<400> SEQUENCE: 1

Ala Gln Gln Asn Ala Phe Tyr Gln Val Leu Asn Met Pro Asn Leu Asn
1               5                   10                  15

Ala Asp Gln Arg Asn Gly Phe Ile Gln Ser Leu Lys Asp Asp Pro Ser
            20                  25                  30

Gln Ser Ala Asn Val Leu Gly Glu Ala Gln Lys Leu Asn Asp Ser Gln
        35                  40                  45

Ala Pro Lys
    50

<210> SEQ ID NO 2
<211> LENGTH: 58
<212> TYPE: PRT
<213> ORGANISM: Staphylococcus aureus

<400> SEQUENCE: 2

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro Lys
    50                  55

<210> SEQ ID NO 3
<211> LENGTH: 58
<212> TYPE: PRT
<213> ORGANISM: Staphylococcus aureus

<400> SEQUENCE: 3

Ala Asp Asn Lys Phe Asn Lys Glu Gln Gln Asn Ala Phe Tyr Glu Ile
1               5                   10                  15
```

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 4
<211> LENGTH: 58
<212> TYPE: PRT
<213> ORGANISM: Staphylococcus aureus

<400> SEQUENCE: 4

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 5
<211> LENGTH: 61
<212> TYPE: PRT
<213> ORGANISM: Staphylococcus aureus

<400> SEQUENCE: 5

Ala Asp Ala Gln Gln Asn Lys Phe Asn Lys Asp Gln Gln Ser Ala Phe
1               5                   10                  15

Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 6
<211> LENGTH: 58
<212> TYPE: PRT
<213> ORGANISM: Staphylococcus aureus

<400> SEQUENCE: 6

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 7
<211> LENGTH: 159
<212> TYPE: DNA
<213> ORGANISM: Staphylococcus aureus

<400> SEQUENCE: 7
gcgcaacaaa acgctttcta tcaggtactg aacatgccta acctgaacgc cgatcagcgt    60

```
aacggcttca tccaaagcct gaaggacgac ccgagccagt ccgcaaacgt tctgggtgaa    120
gctcaaaaac tgaacgacag ccaggcaccg aaagctgac                           159
```

<210> SEQ ID NO 8
<211> LENGTH: 174
<212> TYPE: DNA
<213> ORGANISM: Staphylococcus aureus

<400> SEQUENCE: 8

```
gccgacaaca acttcaacaa agagcagcaa aacgctttct acgaaatcct gaatatgcca    60
aatctgaacg aagagcagcg taacggtttc atccaatctc tgaaagacga tccgtcccag    120
tccgcgaatc tgctggcgga ggctaaaaag ctgaacgaat cccaggctcc gaaa          174
```

<210> SEQ ID NO 9
<211> LENGTH: 174
<212> TYPE: DNA
<213> ORGANISM: Staphylococcus aureus

<400> SEQUENCE: 9

```
gcagacaata agttcaataa agagcagcag aacgcatttt acgagatcct gcatctgccg    60
aacctgaacg aagaacaacg caacggtttc attcagagcc tgaaagacga cccatctcag    120
tccgctaacc tgctggcgga agcaaagaag ctgaacgatg cacaggcgcc gaaa          174
```

<210> SEQ ID NO 10
<211> LENGTH: 174
<212> TYPE: DNA
<213> ORGANISM: Staphylococcus aureus

<400> SEQUENCE: 10

```
gcggataaca aattcaacaa ggagcaacag aacgcattct atgaaattct gcacctgccg    60
aatctgacgg aggagcaacg taacggcttt atccagtccc tgaaggatga tccgtctgtg    120
tctaaagaga tcctggcgga ggcaaaaaaa ctgaatgatg cacaagctcc gaaa          174
```

<210> SEQ ID NO 11
<211> LENGTH: 177
<212> TYPE: DNA
<213> ORGANISM: Staphylococcus aureus

<400> SEQUENCE: 11

```
gcccaacaga acaaatttaa caaagaccag cagtccgcgt tctacgagat tctgaacatg    60
cctaacctga tgaagaaca gcgcaacggt tttattcagt ctctgaagga cgatccttct    120
caatccacca acgtactggg cgaagcgaag aaactgaacg aatctcaggc tccgaag      177
```

<210> SEQ ID NO 12
<211> LENGTH: 174
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
gtagacaaca aattcaataa agaacagcag aacgctttct atgaaatcct gcacctgccg    60
aacctgaacg aagaacagcg taacgcgttt atccagtccc tgaaagacga cccgagccag    120
agcgcaaatc tgctggcgga agcgaaaaag ctgaacgatg cccaggcgcc gaaa          174
```

```
<210> SEQ ID NO 13
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Lys Phe Asn Lys Glu Gln Gln Asn Ala Phe Tyr Glu Ile Leu His Leu
1               5                   10                  15

Pro Asn Leu Asn Glu Glu Gln Arg Asn Gly Phe Ile Gln Ser Leu Lys
            20                  25                  30

Asp Asp Pro Ser Gln Ser Ala Asn Leu Leu Ala Glu Ala Lys Lys Leu
        35                  40                  45

Asn Asp Ala Gln Ala Pro Lys
    50                  55

<210> SEQ ID NO 14
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Lys Phe Asn Lys Glu Gln Gln Asn Ala Phe Tyr Glu Ile Leu His Leu
1               5                   10                  15

Pro Asn Leu Thr Glu Glu Gln Arg Asn Gly Phe Ile Gln Ser Leu Lys
            20                  25                  30

Asp Asp Pro Ser Val Ser Lys Glu Ile Leu Ala Glu Ala Lys Lys Leu
        35                  40                  45

Asn Asp Ala Gln Ala Pro Lys
    50                  55

<210> SEQ ID NO 15
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Lys Phe Asn Lys Glu Gln Gln Asn Ala Phe Tyr Glu Ile Leu His Leu
1               5                   10                  15

Pro Asn Leu Asn Glu Glu Gln Arg Asn Ala Phe Ile Gln Ser Leu Lys
            20                  25                  30

Asp Asp Pro Ser Gln Ser Ala Asn Leu Leu Ala Glu Ala Lys Lys Leu
        35                  40                  45

Asn Asp Ala Gln Ala Pro Lys
    50                  55

<210> SEQ ID NO 16
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16
```

```
Lys Phe Asn Lys Glu Gln Gln Asn Ala Phe Tyr Glu Ile Leu His Leu
1               5                   10                  15

Pro Asn Leu Asn Glu Glu Gln Arg Asn Gly Phe Ile Gln Ser Leu Lys
            20                  25                  30

Asp Asp Pro Ser Gln Ser Ala Asn Leu Leu Ala Glu Ala Lys Lys Leu
        35                  40                  45

Asn Asp Ala Gln Ala Pro Lys Lys Phe Asn Lys Glu Gln Gln Asn Ala
    50                  55                  60

Phe Tyr Glu Ile Leu His Leu Pro Asn Leu Asn Glu Glu Gln Arg Asn
65                  70                  75                  80

Gly Phe Ile Gln Ser Leu Lys Asp Asp Pro Ser Gln Ser Ala Asn Leu
                85                  90                  95

Leu Ala Glu Ala Lys Lys Leu Asn Asp Ala Gln Ala Pro Lys
            100                 105                 110
```

<210> SEQ ID NO 17
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Lys Phe Asn Lys Glu Gln Gln Asn Ala Phe Tyr Glu Ile Leu His Leu
1               5                   10                  15

Pro Asn Leu Thr Glu Glu Gln Arg Asn Gly Phe Ile Gln Ser Leu Lys
            20                  25                  30

Asp Asp Pro Ser Val Ser Lys Glu Ile Leu Ala Glu Ala Lys Lys Leu
        35                  40                  45

Asn Asp Ala Gln Ala Pro Lys Lys Phe Asn Lys Glu Gln Gln Asn Ala
    50                  55                  60

Phe Tyr Glu Ile Leu His Leu Pro Asn Leu Thr Glu Glu Gln Arg Asn
65                  70                  75                  80

Gly Phe Ile Gln Ser Leu Lys Asp Asp Pro Ser Val Ser Lys Glu Ile
                85                  90                  95

Leu Ala Glu Ala Lys Lys Leu Asn Asp Ala Gln Ala Pro Lys
            100                 105                 110
```

<210> SEQ ID NO 18
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Lys Phe Asn Lys Glu Gln Gln Asn Ala Phe Tyr Glu Ile Leu His Leu
1               5                   10                  15

Pro Asn Leu Asn Glu Glu Gln Arg Asn Ala Phe Ile Gln Ser Leu Lys
            20                  25                  30

Asp Asp Pro Ser Gln Ser Ala Asn Leu Leu Ala Glu Ala Lys Lys Leu
        35                  40                  45

Asn Asp Ala Gln Ala Pro Lys Lys Phe Asn Lys Glu Gln Gln Asn Ala
    50                  55                  60

Phe Tyr Glu Ile Leu His Leu Pro Asn Leu Asn Glu Glu Gln Arg Asn
65                  70                  75                  80
```

Ala Phe Ile Gln Ser Leu Lys Asp Asp Pro Ser Gln Ser Ala Asn Leu
                85                  90                  95

Leu Ala Glu Ala Lys Lys Leu Asn Asp Ala Gln Ala Pro Lys
                100                 105                 110

<210> SEQ ID NO 19
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys Lys Phe Asn Lys Glu Gln
        50                  55                  60

Gln Asn Ala Phe Tyr Glu Ile Leu His Leu Pro Asn Leu Asn Glu Glu
65                  70                  75                  80

Gln Arg Asn Gly Phe Ile Gln Ser Leu Lys Asp Asp Pro Ser Gln Ser
                85                  90                  95

Ala Asn Leu Leu Ala Glu Ala Lys Lys Leu Asn Asp Ala Gln Ala Pro
                100                 105                 110

Lys

<210> SEQ ID NO 20
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
                20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys Lys Phe Asn Lys Glu Gln
        50                  55                  60

Gln Asn Ala Phe Tyr Glu Ile Leu His Leu Pro Asn Leu Thr Glu Glu
65                  70                  75                  80

Gln Arg Asn Gly Phe Ile Gln Ser Leu Lys Asp Asp Pro Ser Val Ser
                85                  90                  95

Lys Glu Ile Leu Ala Glu Ala Lys Lys Leu Asn Asp Ala Gln Ala Pro
                100                 105                 110

Lys

<210> SEQ ID NO 21
<211> LENGTH: 113
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 21

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Lys Phe Asn Lys Glu Gln
50                  55                  60

Gln Asn Ala Phe Tyr Glu Ile Leu His Leu Pro Asn Leu Asn Glu Glu
65                  70                  75                  80

Gln Arg Asn Ala Phe Ile Gln Ser Leu Lys Asp Asp Pro Ser Gln Ser
                85                  90                  95

Ala Asn Leu Leu Ala Glu Ala Lys Lys Leu Asn Asp Ala Gln Ala Pro
            100                 105                 110

Lys

<210> SEQ ID NO 22
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Lys Phe Asn Lys Glu Gln Gln Asn Ala Phe Tyr Glu Ile Leu His Leu
1               5                   10                  15

Pro Asn Leu Asn Glu Glu Gln Arg Asn Gly Phe Ile Gln Ser Leu Lys
            20                  25                  30

Asp Asp Pro Ser Gln Ser Ala Asn Leu Leu Ala Glu Ala Lys Lys Leu
        35                  40                  45

Asn Asp Ala Gln Ala Pro Lys Lys Phe Asn Lys Glu Gln Gln Asn Ala
    50                  55                  60

Phe Tyr Glu Ile Leu His Leu Pro Asn Leu Asn Glu Glu Gln Arg Asn
65                  70                  75                  80

Gly Phe Ile Gln Ser Leu Lys Asp Asp Pro Ser Gln Ser Ala Asn Leu
                85                  90                  95

Leu Ala Glu Ala Lys Lys Leu Asn Asp Ala Gln Ala Pro Lys Lys Phe
            100                 105                 110

Asn Lys Glu Gln Gln Asn Ala Phe Tyr Glu Ile Leu His Leu Pro Asn
        115                 120                 125

Leu Asn Glu Glu Gln Arg Asn Gly Phe Ile Gln Ser Leu Lys Asp Asp
    130                 135                 140

Pro Ser Gln Ser Ala Asn Leu Leu Ala Glu Ala Lys Lys Leu Asn Asp
145                 150                 155                 160

Ala Gln Ala Pro Lys Lys Phe Asn Lys Glu Gln Gln Asn Ala Phe Tyr
                165                 170                 175

Glu Ile Leu His Leu Pro Asn Leu Asn Glu Glu Gln Arg Asn Gly Phe
            180                 185                 190

Ile Gln Ser Leu Lys Asp Asp Pro Ser Gln Ser Ala Asn Leu Leu Ala
        195                 200                 205
```

```
Glu Ala Lys Lys Leu Asn Asp Ala Gln Ala Pro Lys Phe Asn Lys
210                 215                 220

Gln Gln Asn Ala Phe Tyr Glu Ile Leu His Leu Pro Asn Leu Asn
225                 230                 235                 240

Glu Glu Gln Arg Asn Gly Phe Ile Gln Ser Leu Lys Asp Asp Pro Ser
                245                 250                 255

Gln Ser Ala Asn Leu Leu Ala Glu Ala Lys Lys Leu Asn Asp Ala Gln
                260                 265                 270

Ala Pro Lys
        275

<210> SEQ ID NO 23
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Lys Phe Asn Lys Glu Gln Gln Asn Ala Phe Tyr Glu Ile Leu His Leu
1               5                   10                  15

Pro Asn Leu Thr Glu Glu Gln Arg Asn Gly Phe Ile Gln Ser Leu Lys
                20                  25                  30

Asp Asp Pro Ser Val Ser Lys Glu Ile Leu Ala Glu Ala Lys Lys Leu
            35                  40                  45

Asn Asp Ala Gln Ala Pro Lys Lys Phe Asn Lys Glu Gln Gln Asn Ala
        50                  55                  60

Phe Tyr Glu Ile Leu His Leu Pro Asn Leu Thr Glu Glu Gln Arg Asn
65                  70                  75                  80

Gly Phe Ile Gln Ser Leu Lys Asp Asp Pro Ser Val Ser Lys Glu Ile
                85                  90                  95

Leu Ala Glu Ala Lys Lys Leu Asn Asp Ala Gln Ala Pro Lys Lys Phe
            100                 105                 110

Asn Lys Glu Gln Gln Asn Ala Phe Tyr Glu Ile Leu His Leu Pro Asn
        115                 120                 125

Leu Thr Glu Glu Gln Arg Asn Gly Phe Ile Gln Ser Leu Lys Asp Asp
    130                 135                 140

Pro Ser Val Ser Lys Glu Ile Leu Ala Glu Ala Lys Lys Leu Asn Asp
145                 150                 155                 160

Ala Gln Ala Pro Lys Lys Phe Asn Lys Glu Gln Gln Asn Ala Phe Tyr
                165                 170                 175

Glu Ile Leu His Leu Pro Asn Leu Thr Glu Glu Gln Arg Asn Gly Phe
            180                 185                 190

Ile Gln Ser Leu Lys Asp Asp Pro Ser Val Ser Lys Glu Ile Leu Ala
        195                 200                 205

Glu Ala Lys Lys Leu Asn Asp Ala Gln Ala Pro Lys Lys Phe Asn Lys
    210                 215                 220

Glu Gln Gln Asn Ala Phe Tyr Glu Ile Leu His Leu Pro Asn Leu Thr
225                 230                 235                 240

Glu Glu Gln Arg Asn Gly Phe Ile Gln Ser Leu Lys Asp Asp Pro Ser
                245                 250                 255

Val Ser Lys Glu Ile Leu Ala Glu Ala Lys Lys Leu Asn Asp Ala Gln
            260                 265                 270

Ala Pro Lys
        275
```

<210> SEQ ID NO 24
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Lys Phe Asn Lys Glu Gln Gln Asn Ala Phe Tyr Glu Ile Leu His Leu
1               5                   10                  15

Pro Asn Leu Asn Glu Glu Gln Arg Asn Ala Phe Ile Gln Ser Leu Lys
            20                  25                  30

Asp Asp Pro Ser Gln Ser Ala Asn Leu Leu Ala Glu Ala Lys Lys Leu
        35                  40                  45

Asn Asp Ala Gln Ala Pro Lys Lys Phe Asn Lys Glu Gln Gln Asn Ala
    50                  55                  60

Phe Tyr Glu Ile Leu His Leu Pro Asn Leu Asn Glu Glu Gln Arg Asn
65                  70                  75                  80

Ala Phe Ile Gln Ser Leu Lys Asp Asp Pro Ser Gln Ser Ala Asn Leu
                85                  90                  95

Leu Ala Glu Ala Lys Lys Leu Asn Asp Ala Gln Ala Pro Lys Lys Phe
            100                 105                 110

Asn Lys Glu Gln Gln Asn Ala Phe Tyr Glu Ile Leu His Leu Pro Asn
        115                 120                 125

Leu Asn Glu Glu Gln Arg Asn Ala Phe Ile Gln Ser Leu Lys Asp Asp
    130                 135                 140

Pro Ser Gln Ser Ala Asn Leu Leu Ala Glu Ala Lys Lys Leu Asn Asp
145                 150                 155                 160

Ala Gln Ala Pro Lys Lys Phe Asn Lys Glu Gln Gln Asn Ala Phe Tyr
                165                 170                 175

Glu Ile Leu His Leu Pro Asn Leu Asn Glu Glu Gln Arg Asn Ala Phe
            180                 185                 190

Ile Gln Ser Leu Lys Asp Asp Pro Ser Gln Ser Ala Asn Leu Leu Ala
        195                 200                 205

Glu Ala Lys Lys Leu Asn Asp Ala Gln Ala Pro Lys Lys Phe Asn Lys
    210                 215                 220

Glu Gln Gln Asn Ala Phe Tyr Glu Ile Leu His Leu Pro Asn Leu Asn
225                 230                 235                 240

Glu Glu Gln Arg Asn Ala Phe Ile Gln Ser Leu Lys Asp Asp Pro Ser
                245                 250                 255

Gln Ser Ala Asn Leu Leu Ala Glu Ala Lys Lys Leu Asn Asp Ala Gln
            260                 265                 270

Ala Pro Lys
            275
```

<210> SEQ ID NO 25
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Ala Asp Asn Lys Phe Asn Lys Glu Gln Gln Asn Ala Phe Tyr Glu Ile
1               5                   10                  15
```

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys Lys Phe Asn Lys Glu Gln
 50                  55                  60

Gln Asn Ala Phe Tyr Glu Ile Leu His Leu Pro Asn Leu Asn Glu Glu
 65                  70                  75                  80

Gln Arg Asn Gly Phe Ile Gln Ser Leu Lys Asp Asp Pro Ser Gln Ser
                    85                  90                  95

Ala Asn Leu Leu Ala Glu Ala Lys Lys Leu Asn Asp Ala Gln Ala Pro
            100                 105                 110

Lys Lys Phe Asn Lys Glu Gln Gln Asn Ala Phe Tyr Glu Ile Leu His
            115                 120                 125

Leu Pro Asn Leu Asn Glu Glu Gln Arg Asn Gly Phe Ile Gln Ser Leu
130                 135                 140

Lys Asp Asp Pro Ser Gln Ser Ala Asn Leu Leu Ala Glu Ala Lys Lys
145                 150                 155                 160

Leu Asn Asp Ala Gln Ala Pro Lys Lys Phe Asn Lys Glu Gln Gln Asn
                165                 170                 175

Ala Phe Tyr Glu Ile Leu His Leu Pro Asn Leu Asn Glu Glu Gln Arg
            180                 185                 190

Asn Gly Phe Ile Gln Ser Leu Lys Asp Asp Pro Ser Gln Ser Ala Asn
            195                 200                 205

Leu Leu Ala Glu Ala Lys Lys Leu Asn Asp Ala Gln Ala Pro Lys Lys
            210                 215                 220

Phe Asn Lys Glu Gln Gln Asn Ala Phe Tyr Glu Ile Leu His Leu Pro
225                 230                 235                 240

Asn Leu Asn Glu Glu Gln Arg Asn Gly Phe Ile Gln Ser Leu Lys Asp
                245                 250                 255

Asp Pro Ser Gln Ser Ala Asn Leu Leu Ala Glu Ala Lys Lys Leu Asn
            260                 265                 270

Asp Ala Gln Ala Pro Lys
            275

<210> SEQ ID NO 26
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys Lys Phe Asn Lys Glu Gln
 50                  55                  60

Gln Asn Ala Phe Tyr Glu Ile Leu His Leu Pro Asn Leu Thr Glu Glu
 65                  70                  75                  80

Gln Arg Asn Gly Phe Ile Gln Ser Leu Lys Asp Asp Pro Ser Val Ser

```
                        85                  90                  95
Lys Glu Ile Leu Ala Glu Ala Lys Lys Leu Asn Asp Ala Gln Ala Pro
                100                 105                 110

Lys Lys Phe Asn Lys Glu Gln Gln Asn Ala Phe Tyr Glu Ile Leu His
        115                 120                 125

Leu Pro Asn Leu Thr Glu Glu Gln Arg Asn Gly Phe Ile Gln Ser Leu
    130                 135                 140

Lys Asp Asp Pro Ser Val Ser Lys Glu Ile Leu Ala Glu Ala Lys Lys
145                 150                 155                 160

Leu Asn Asp Ala Gln Ala Pro Lys Lys Phe Asn Lys Glu Gln Gln Asn
                165                 170                 175

Ala Phe Tyr Glu Ile Leu His Leu Pro Asn Leu Thr Glu Glu Gln Arg
            180                 185                 190

Asn Gly Phe Ile Gln Ser Leu Lys Asp Asp Pro Ser Val Ser Lys Glu
        195                 200                 205

Ile Leu Ala Glu Ala Lys Lys Leu Asn Asp Ala Gln Ala Pro Lys Lys
    210                 215                 220

Phe Asn Lys Glu Gln Gln Asn Ala Phe Tyr Glu Ile Leu His Leu Pro
225                 230                 235                 240

Asn Leu Thr Glu Glu Gln Arg Asn Gly Phe Ile Gln Ser Leu Lys Asp
                245                 250                 255

Asp Pro Ser Val Ser Lys Glu Ile Leu Ala Glu Ala Lys Lys Leu Asn
            260                 265                 270

Asp Ala Gln Ala Pro Lys
        275

<210> SEQ ID NO 27
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Lys Phe Asn Lys Glu Gln
    50                  55                  60

Gln Asn Ala Phe Tyr Glu Ile Leu His Leu Pro Asn Leu Asn Glu Glu
65                  70                  75                  80

Gln Arg Asn Ala Phe Ile Gln Ser Leu Lys Asp Asp Pro Ser Gln Ser
                85                  90                  95

Ala Asn Leu Leu Ala Glu Ala Lys Lys Leu Asn Asp Ala Gln Ala Pro
            100                 105                 110

Lys Lys Phe Asn Lys Glu Gln Gln Asn Ala Phe Tyr Glu Ile Leu His
        115                 120                 125

Leu Pro Asn Leu Asn Glu Glu Gln Arg Asn Ala Phe Ile Gln Ser Leu
    130                 135                 140

Lys Asp Asp Pro Ser Gln Ser Ala Asn Leu Leu Ala Glu Ala Lys Lys
145                 150                 155                 160
```

```
Leu Asn Asp Ala Gln Ala Pro Lys Lys Phe Asn Lys Glu Gln Gln Asn
                165                 170                 175

Ala Phe Tyr Glu Ile Leu His Leu Pro Asn Leu Asn Glu Glu Gln Arg
            180                 185                 190

Asn Ala Phe Ile Gln Ser Leu Lys Asp Asp Pro Ser Gln Ser Ala Asn
        195                 200                 205

Leu Leu Ala Glu Ala Lys Lys Leu Asn Asp Ala Gln Ala Pro Lys Lys
    210                 215                 220

Phe Asn Lys Glu Gln Gln Asn Ala Phe Tyr Glu Ile Leu His Leu Pro
225                 230                 235                 240

Asn Leu Asn Glu Glu Gln Arg Asn Ala Phe Ile Gln Ser Leu Lys Asp
                245                 250                 255

Asp Pro Ser Gln Ser Ala Asn Leu Leu Ala Glu Ala Lys Lys Leu Asn
            260                 265                 270

Asp Ala Gln Ala Pro Lys
        275

<210> SEQ ID NO 28
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Phe Asn Lys Glu Gln Gln Asn Ala Phe Tyr Glu Ile Leu His Leu Pro
1               5                   10                  15

Asn Leu Asn Glu Glu Gln Arg Asn Gly Phe Ile Gln Ser Leu Lys Asp
            20                  25                  30

Asp Pro Ser Gln Ser Ala Asn Leu Leu Ala Glu Ala Lys Lys Leu Asn
        35                  40                  45

Asp Ala Gln Ala Pro Lys
    50

<210> SEQ ID NO 29
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Phe Asn Lys Glu Gln Gln Asn Ala Phe Tyr Glu Ile Leu His Leu Pro
1               5                   10                  15

Asn Leu Thr Glu Glu Gln Arg Asn Gly Phe Ile Gln Ser Leu Lys Asp
            20                  25                  30

Asp Pro Ser Val Ser Lys Glu Ile Leu Ala Glu Ala Lys Lys Leu Asn
        35                  40                  45

Asp Ala Gln Ala Pro Lys
    50

<210> SEQ ID NO 30
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 30

Phe Asn Lys Glu Gln Gln Asn Ala Phe Tyr Glu Ile Leu His Leu Pro
1               5                   10                  15

Asn Leu Asn Glu Glu Gln Arg Asn Ala Phe Ile Gln Ser Leu Lys Asp
            20                  25                  30

Asp Pro Ser Gln Ser Ala Asn Leu Leu Ala Glu Ala Lys Lys Leu Asn
        35                  40                  45

Asp Ala Gln Ala Pro Lys
        50

<210> SEQ ID NO 31
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Phe Asn Lys Glu Gln Gln Asn Ala Phe Tyr Glu Ile Leu His Leu Pro
1               5                   10                  15

Asn Leu Asn Glu Glu Gln Arg Asn Gly Phe Ile Gln Ser Leu Lys Asp
            20                  25                  30

Asp Pro Ser Gln Ser Ala Asn Leu Leu Ala Glu Ala Lys Lys Leu Asn
        35                  40                  45

Asp Ala Gln Ala Pro Lys Phe Asn Lys Glu Gln Gln Asn Ala Phe Tyr
    50                  55                  60

Glu Ile Leu His Leu Pro Asn Leu Asn Glu Glu Gln Arg Asn Gly Phe
65                  70                  75                  80

Ile Gln Ser Leu Lys Asp Asp Pro Ser Gln Ser Ala Asn Leu Leu Ala
                85                  90                  95

Glu Ala Lys Lys Leu Asn Asp Ala Gln Ala Pro Lys
            100                 105

<210> SEQ ID NO 32
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Phe Asn Lys Glu Gln Gln Asn Ala Phe Tyr Glu Ile Leu His Leu Pro
1               5                   10                  15

Asn Leu Thr Glu Glu Gln Arg Asn Gly Phe Ile Gln Ser Leu Lys Asp
            20                  25                  30

Asp Pro Ser Val Ser Lys Glu Ile Leu Ala Glu Ala Lys Lys Leu Asn
        35                  40                  45

Asp Ala Gln Ala Pro Lys Phe Asn Lys Glu Gln Gln Asn Ala Phe Tyr
    50                  55                  60

Glu Ile Leu His Leu Pro Asn Leu Thr Glu Gln Gln Arg Asn Gly Phe
65                  70                  75                  80

Ile Gln Ser Leu Lys Asp Asp Pro Ser Val Ser Lys Glu Ile Leu Ala
                85                  90                  95

Glu Ala Lys Lys Leu Asn Asp Ala Gln Ala Pro Lys
            100                 105
```

<210> SEQ ID NO 33
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Phe Asn Lys Glu Gln Gln Asn Ala Phe Tyr Glu Ile Leu His Leu Pro
1               5                   10                  15

Asn Leu Asn Glu Glu Gln Arg Asn Ala Phe Ile Gln Ser Leu Lys Asp
            20                  25                  30

Asp Pro Ser Gln Ser Ala Asn Leu Leu Ala Glu Ala Lys Lys Leu Asn
        35                  40                  45

Asp Ala Gln Ala Pro Lys Phe Asn Lys Glu Gln Gln Asn Ala Phe Tyr
    50                  55                  60

Glu Ile Leu His Leu Pro Asn Leu Asn Glu Glu Gln Arg Asn Ala Phe
65                  70                  75                  80

Ile Gln Ser Leu Lys Asp Asp Pro Ser Gln Ser Ala Asn Leu Leu Ala
                85                  90                  95

Glu Ala Lys Lys Leu Asn Asp Ala Gln Ala Pro Lys
            100                 105
```

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Phe Asn Lys Glu Gln Gln
    50                  55                  60

Asn Ala Phe Tyr Glu Ile Leu His Leu Pro Asn Leu Asn Glu Glu Gln
65                  70                  75                  80

Arg Asn Gly Phe Ile Gln Ser Leu Lys Asp Asp Pro Ser Gln Ser Ala
                85                  90                  95

Asn Leu Leu Ala Glu Ala Lys Lys Leu Asn Asp Ala Gln Ala Pro Lys
            100                 105                 110
```

<210> SEQ ID NO 35
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30
```

Ser Leu Lys Asp Asp Pro Ser Val Ser Lys Glu Ile Leu Ala Glu Ala
            35                  40                  45

Lys Lys Leu Asn Asp Ala Gln Ala Pro Lys Phe Asn Lys Glu Gln Gln
 50                  55                  60

Asn Ala Phe Tyr Glu Ile Leu His Leu Pro Asn Leu Thr Glu Gln
65                  70                  75                  80

Arg Asn Gly Phe Ile Gln Ser Leu Lys Asp Asp Pro Ser Val Ser Lys
                    85                  90                  95

Glu Ile Leu Ala Glu Ala Lys Lys Leu Asn Asp Ala Gln Ala Pro Lys
            100                 105                 110

<210> SEQ ID NO 36
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys Phe Asn Lys Glu Gln Gln
 50                  55                  60

Asn Ala Phe Tyr Glu Ile Leu His Leu Pro Asn Leu Asn Glu Glu Gln
65                  70                  75                  80

Arg Asn Ala Phe Ile Gln Ser Leu Lys Asp Asp Pro Ser Gln Ser Ala
                    85                  90                  95

Asn Leu Leu Ala Glu Ala Lys Lys Leu Asn Asp Ala Gln Ala Pro Lys
            100                 105                 110

<210> SEQ ID NO 37
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Phe Asn Lys Glu Gln Gln Asn Ala Phe Tyr Glu Ile Leu His Leu Pro
1               5                   10                  15

Asn Leu Asn Glu Glu Gln Arg Asn Gly Phe Ile Gln Ser Leu Lys Asp
                20                  25                  30

Asp Pro Ser Gln Ser Ala Asn Leu Leu Ala Glu Ala Lys Lys Leu Asn
            35                  40                  45

Asp Ala Gln Ala Pro Lys Phe Asn Lys Glu Gln Gln Asn Ala Phe Tyr
 50                  55                  60

Glu Ile Leu His Leu Pro Asn Leu Asn Glu Glu Gln Arg Asn Gly Phe
65                  70                  75                  80

Ile Gln Ser Leu Lys Asp Asp Pro Ser Gln Ser Ala Asn Leu Leu Ala
                    85                  90                  95

Glu Ala Lys Lys Leu Asn Asp Ala Gln Ala Pro Lys Phe Asn Lys Glu
            100                 105                 110

```
Gln Gln Asn Ala Phe Tyr Glu Ile Leu His Leu Pro Asn Leu Asn Glu
            115                 120                 125

Glu Gln Arg Asn Gly Phe Ile Gln Ser Leu Lys Asp Asp Pro Ser Gln
        130                 135                 140

Ser Ala Asn Leu Leu Ala Glu Ala Lys Lys Leu Asn Asp Ala Gln Ala
145                 150                 155                 160

Pro Lys Phe Asn Lys Glu Gln Gln Asn Ala Phe Tyr Glu Ile Leu His
                165                 170                 175

Leu Pro Asn Leu Asn Glu Glu Gln Arg Asn Gly Phe Ile Gln Ser Leu
            180                 185                 190

Lys Asp Asp Pro Ser Gln Ser Ala Asn Leu Leu Ala Glu Ala Lys Lys
        195                 200                 205

Leu Asn Asp Ala Gln Ala Pro Lys Phe Asn Lys Glu Gln Gln Asn Ala
        210                 215                 220

Phe Tyr Glu Ile Leu His Leu Pro Asn Leu Asn Glu Glu Gln Arg Asn
225                 230                 235                 240

Gly Phe Ile Gln Ser Leu Lys Asp Asp Pro Ser Gln Ser Ala Asn Leu
                245                 250                 255

Leu Ala Glu Ala Lys Lys Leu Asn Asp Ala Gln Ala Pro Lys
            260                 265                 270

<210> SEQ ID NO 38
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Phe Asn Lys Glu Gln Gln Asn Ala Phe Tyr Glu Ile Leu His Leu Pro
1               5                   10                  15

Asn Leu Thr Glu Glu Gln Arg Asn Gly Phe Ile Gln Ser Leu Lys Asp
            20                  25                  30

Asp Pro Ser Val Ser Lys Glu Ile Leu Ala Glu Ala Lys Lys Leu Asn
        35                  40                  45

Asp Ala Gln Ala Pro Lys Phe Asn Lys Glu Gln Gln Asn Ala Phe Tyr
    50                  55                  60

Glu Ile Leu His Leu Pro Asn Leu Thr Glu Glu Gln Arg Asn Gly Phe
65                  70                  75                  80

Ile Gln Ser Leu Lys Asp Asp Pro Ser Val Ser Lys Glu Ile Leu Ala
                85                  90                  95

Glu Ala Lys Lys Leu Asn Asp Ala Gln Ala Pro Lys Phe Asn Lys Glu
            100                 105                 110

Gln Gln Asn Ala Phe Tyr Glu Ile Leu His Leu Pro Asn Leu Thr Glu
        115                 120                 125

Glu Gln Arg Asn Gly Phe Ile Gln Ser Leu Lys Asp Asp Pro Ser Val
    130                 135                 140

Ser Lys Glu Ile Leu Ala Glu Ala Lys Lys Leu Asn Asp Ala Gln Ala
145                 150                 155                 160

Pro Lys Phe Asn Lys Glu Gln Gln Asn Ala Phe Tyr Glu Ile Leu His
                165                 170                 175

Leu Pro Asn Leu Thr Glu Glu Gln Arg Asn Gly Phe Ile Gln Ser Leu
            180                 185                 190

Lys Asp Asp Pro Ser Val Ser Lys Glu Ile Leu Ala Glu Ala Lys Lys
```

```
                    195                 200                 205
Leu Asn Asp Ala Gln Ala Pro Lys Phe Asn Lys Glu Gln Gln Asn Ala
            210                 215                 220

Phe Tyr Glu Ile Leu His Leu Pro Asn Leu Thr Glu Glu Gln Arg Asn
225                 230                 235                 240

Gly Phe Ile Gln Ser Leu Lys Asp Asp Pro Ser Val Ser Lys Glu Ile
                245                 250                 255

Leu Ala Glu Ala Lys Lys Leu Asn Asp Ala Gln Ala Pro Lys
            260                 265                 270

<210> SEQ ID NO 39
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Phe Asn Lys Glu Gln Gln Asn Ala Phe Tyr Glu Ile Leu His Leu Pro
1               5                   10                  15

Asn Leu Asn Glu Glu Gln Arg Asn Ala Phe Ile Gln Ser Leu Lys Asp
            20                  25                  30

Asp Pro Ser Gln Ser Ala Asn Leu Leu Ala Glu Ala Lys Lys Leu Asn
        35                  40                  45

Asp Ala Gln Ala Pro Lys Phe Asn Lys Glu Gln Gln Asn Ala Phe Tyr
    50                  55                  60

Glu Ile Leu His Leu Pro Asn Leu Asn Glu Glu Gln Arg Asn Ala Phe
65                  70                  75                  80

Ile Gln Ser Leu Lys Asp Asp Pro Ser Gln Ser Ala Asn Leu Leu Ala
                85                  90                  95

Glu Ala Lys Lys Leu Asn Asp Ala Gln Ala Pro Lys Phe Asn Lys Glu
            100                 105                 110

Gln Gln Asn Ala Phe Tyr Glu Ile Leu His Leu Pro Asn Leu Asn Glu
        115                 120                 125

Glu Gln Arg Asn Ala Phe Ile Gln Ser Leu Lys Asp Asp Pro Ser Gln
    130                 135                 140

Ser Ala Asn Leu Leu Ala Glu Ala Lys Lys Leu Asn Asp Ala Gln Ala
145                 150                 155                 160

Pro Lys Phe Asn Lys Glu Gln Gln Asn Ala Phe Tyr Glu Ile Leu His
                165                 170                 175

Leu Pro Asn Leu Asn Glu Glu Gln Arg Asn Ala Phe Ile Gln Ser Leu
            180                 185                 190

Lys Asp Asp Pro Ser Gln Ser Ala Asn Leu Leu Ala Glu Ala Lys Lys
        195                 200                 205

Leu Asn Asp Ala Gln Ala Pro Lys Phe Asn Lys Glu Gln Gln Asn Ala
    210                 215                 220

Phe Tyr Glu Ile Leu His Leu Pro Asn Leu Asn Glu Glu Gln Arg Asn
225                 230                 235                 240

Ala Phe Ile Gln Ser Leu Lys Asp Asp Pro Ser Gln Ser Ala Asn Leu
                245                 250                 255

Leu Ala Glu Ala Lys Lys Leu Asn Asp Ala Gln Ala Pro Lys
            260                 265                 270

<210> SEQ ID NO 40
<211> LENGTH: 274
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Phe Asn Lys Glu Gln Gln
50                  55                  60

Asn Ala Phe Tyr Glu Ile Leu His Leu Pro Asn Leu Asn Glu Glu Gln
65                  70                  75                  80

Arg Asn Gly Phe Ile Gln Ser Leu Lys Asp Asp Pro Ser Gln Ser Ala
                85                  90                  95

Asn Leu Leu Ala Glu Ala Lys Lys Leu Asn Asp Ala Gln Ala Pro Lys
            100                 105                 110

Phe Asn Lys Glu Gln Gln Asn Ala Phe Tyr Glu Ile Leu His Leu Pro
        115                 120                 125

Asn Leu Asn Glu Glu Gln Arg Asn Gly Phe Ile Gln Ser Leu Lys Asp
    130                 135                 140

Asp Pro Ser Gln Ser Ala Asn Leu Leu Ala Glu Ala Lys Lys Leu Asn
145                 150                 155                 160

Asp Ala Gln Ala Pro Lys Phe Asn Lys Glu Gln Gln Asn Ala Phe Tyr
                165                 170                 175

Glu Ile Leu His Leu Pro Asn Leu Asn Glu Glu Gln Arg Asn Gly Phe
            180                 185                 190

Ile Gln Ser Leu Lys Asp Asp Pro Ser Gln Ser Ala Asn Leu Leu Ala
        195                 200                 205

Glu Ala Lys Lys Leu Asn Asp Ala Gln Ala Pro Lys Phe Asn Lys Glu
    210                 215                 220

Gln Gln Asn Ala Phe Tyr Glu Ile Leu His Leu Pro Asn Leu Asn Glu
225                 230                 235                 240

Glu Gln Arg Asn Gly Phe Ile Gln Ser Leu Lys Asp Asp Pro Ser Gln
                245                 250                 255

Ser Ala Asn Leu Leu Ala Glu Ala Lys Lys Leu Asn Asp Ala Gln Ala
            260                 265                 270

Pro Lys

<210> SEQ ID NO 41
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala

```
                35                  40                  45
Lys Lys Leu Asn Asp Ala Gln Ala Pro Lys Phe Asn Lys Glu Gln Gln
 50                  55                  60
Asn Ala Phe Tyr Glu Ile Leu His Leu Pro Asn Leu Thr Glu Glu Gln
65                  70                  75                  80
Arg Asn Gly Phe Ile Gln Ser Leu Lys Asp Asp Pro Ser Val Ser Lys
                85                  90                  95
Glu Ile Leu Ala Glu Ala Lys Lys Leu Asn Asp Ala Gln Ala Pro Lys
            100                 105                 110
Phe Asn Lys Glu Gln Gln Asn Ala Phe Tyr Glu Ile Leu His Leu Pro
        115                 120                 125
Asn Leu Thr Glu Glu Gln Arg Asn Gly Phe Ile Gln Ser Leu Lys Asp
    130                 135                 140
Asp Pro Ser Val Ser Lys Glu Ile Leu Ala Glu Ala Lys Lys Leu Asn
145                 150                 155                 160
Asp Ala Gln Ala Pro Lys Phe Asn Lys Glu Gln Gln Asn Ala Phe Tyr
                165                 170                 175
Glu Ile Leu His Leu Pro Asn Leu Thr Glu Glu Gln Arg Asn Gly Phe
            180                 185                 190
Ile Gln Ser Leu Lys Asp Asp Pro Ser Val Ser Lys Glu Ile Leu Ala
        195                 200                 205
Glu Ala Lys Lys Leu Asn Asp Ala Gln Ala Pro Lys Phe Asn Lys Glu
    210                 215                 220
Gln Gln Asn Ala Phe Tyr Glu Ile Leu His Leu Pro Asn Leu Thr Glu
225                 230                 235                 240
Glu Gln Arg Asn Gly Phe Ile Gln Ser Leu Lys Asp Asp Pro Ser Val
                245                 250                 255
Ser Lys Glu Ile Leu Ala Glu Ala Lys Lys Leu Asn Asp Ala Gln Ala
            260                 265                 270
Pro Lys

<210> SEQ ID NO 42
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Val Asp Asn Lys Phe Asn Lys Glu Gln Gln Asn Ala Phe Tyr Glu Ile
1               5                  10                  15
Leu His Leu Pro Asn Leu Asn Glu Glu Gln Arg Asn Ala Phe Ile Gln
            20                  25                  30
Ser Leu Lys Asp Asp Pro Ser Gln Ser Ala Asn Leu Leu Ala Glu Ala
        35                  40                  45
Lys Lys Leu Asn Asp Ala Gln Ala Pro Lys Phe Asn Lys Glu Gln Gln
    50                  55                  60
Asn Ala Phe Tyr Glu Ile Leu His Leu Pro Asn Leu Asn Glu Glu Gln
65                  70                  75                  80
Arg Asn Ala Phe Ile Gln Ser Leu Lys Asp Asp Pro Ser Gln Ser Ala
                85                  90                  95
Asn Leu Leu Ala Glu Ala Lys Lys Leu Asn Asp Ala Gln Ala Pro Lys
            100                 105                 110
Phe Asn Lys Glu Gln Gln Asn Ala Phe Tyr Glu Ile Leu His Leu Pro
```

```
                115                 120                 125
Asn Leu Asn Glu Glu Gln Arg Asn Ala Phe Ile Gln Ser Leu Lys Asp
        130                 135                 140

Asp Pro Ser Gln Ser Ala Asn Leu Leu Ala Glu Ala Lys Lys Leu Asn
145                 150                 155                 160

Asp Ala Gln Ala Pro Lys Phe Asn Lys Glu Gln Asn Ala Phe Tyr
                165                 170                 175

Glu Ile Leu His Leu Pro Asn Leu Asn Glu Gln Arg Asn Ala Phe
                180                 185                 190

Ile Gln Ser Leu Lys Asp Asp Pro Ser Gln Ser Ala Asn Leu Leu Ala
                195                 200                 205

Glu Ala Lys Lys Leu Asn Asp Ala Gln Ala Pro Lys Phe Asn Lys Glu
        210                 215                 220

Gln Gln Asn Ala Phe Tyr Glu Ile Leu His Leu Pro Asn Leu Asn Glu
225                 230                 235                 240

Glu Gln Arg Asn Ala Phe Ile Gln Ser Leu Lys Asp Asp Pro Ser Gln
                245                 250                 255

Ser Ala Asn Leu Leu Ala Glu Ala Lys Lys Leu Asn Asp Ala Gln Ala
                260                 265                 270

Pro Lys

<210> SEQ ID NO 43
<211> LENGTH: 51
<212> TYPE: PRT
<213> ORGANISM: Staphylococcus aureus

<400> SEQUENCE: 43

Ala Gln Gln Asn Ala Phe Tyr Gln Val Leu Asn Met Pro Asn Leu Asn
1               5                   10                  15

Ala Asp Gln Arg Asn Lys Phe Ile Gln Ser Leu Lys Asp Asp Pro Ser
                20                  25                  30

Gln Ser Ala Asn Val Leu Gly Glu Ala Gln Lys Leu Asn Asp Ser Gln
                35                  40                  45

Ala Pro Lys
    50

<210> SEQ ID NO 44
<211> LENGTH: 58
<212> TYPE: PRT
<213> ORGANISM: Staphylococcus aureus

<400> SEQUENCE: 44

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Lys Phe Ile Gln
                20                  25                  30

Ser Leu Lys Asp Asp Pro Ser Gln Ser Ala Asn Leu Leu Ala Glu Ala
                35                  40                  45

Lys Lys Leu Asn Glu Ser Gln Ala Pro Lys
    50                  55

<210> SEQ ID NO 45
<211> LENGTH: 58
<212> TYPE: PRT
<213> ORGANISM: Staphylococcus aureus

<400> SEQUENCE: 45
```

```
Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Lys Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 46
<211> LENGTH: 58
<212> TYPE: PRT
<213> ORGANISM: Staphylococcus aureus

<400> SEQUENCE: 46

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Lys Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55
```

<210> SEQ ID NO 47
<211> LENGTH: 61
<212> TYPE: PRT
<213> ORGANISM: Staphylococcus aureus

<400> SEQUENCE: 47

```
Ala Asp Ala Gln Gln Asn Lys Phe Asn Lys Asp Gln Gln Ser Ala Phe
1               5                   10                  15

Tyr Glu Ile Leu Asn Met Pro Asn Leu Asn Glu Glu Gln Arg Asn Lys
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60
```

<210> SEQ ID NO 48
<211> LENGTH: 58
<212> TYPE: PRT
<213> ORGANISM: Staphylococcus aureus

<400> SEQUENCE: 48

```
Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Lys Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 49
<211> LENGTH: 159
<212> TYPE: DNA
<213> ORGANISM: Staphylococcus aureus

<400> SEQUENCE: 49

```
gcgcaacaaa acgctttcta tcaggtactg aacatgccta acctgaacgc cgatcagcgt    60
aacaaattca tccaaagcct gaaggacgac ccgagccagt ccgcaaacgt tctgggtgaa   120
gctcaaaaac tgaacgacag ccaggcaccg aaagctgac                          159
```

<210> SEQ ID NO 50
<211> LENGTH: 174
<212> TYPE: DNA
<213> ORGANISM: Staphylococcus aureus

<400> SEQUENCE: 50

```
gccgacaaca acttcaacaa agagcagcaa acgctttct acgaaatcct gaatatgcca    60
aatctgaacg aagagcagcg taacaaattc atccaatctc tgaaagacga tccgtcccag   120
tccgcgaatc tgctggcgga ggctaaaaag ctgaacgaat cccaggctcc gaaa         174
```

<210> SEQ ID NO 51
<211> LENGTH: 174
<212> TYPE: DNA
<213> ORGANISM: Staphylococcus aureus

<400> SEQUENCE: 51

```
gcagacaata agttcaataa agagcagcag aacgcatttt acgagatcct gcatctgccg    60
aacctgaacg aagaacaacg caacaaattc attcagagcc tgaaagacga cccatctcag   120
tccgctaacc tgctggcgga agcaaagaag ctgaacgatg cacaggcgcc gaaa         174
```

<210> SEQ ID NO 52
<211> LENGTH: 174
<212> TYPE: DNA
<213> ORGANISM: Staphylococcus aureus

<400> SEQUENCE: 52

```
gcggataaca aattcaacaa ggagcaacag aacgcattct atgaaattct gcacctgccg    60
aatctgacgg aggagcaacg taacaaattt atccagtccc tgaaggatga tccgtctgtg   120
tctaaagaga tcctggcgga ggcaaaaaaa ctgaatgatg cacaagctcc gaaa         174
```

<210> SEQ ID NO 53
<211> LENGTH: 177
<212> TYPE: DNA
<213> ORGANISM: Staphylococcus aureus

<400> SEQUENCE: 53

```
gcccaacaga acaaatttaa caaagaccag cagtccgcgt tctacgagat tctgaacatg    60
cctaacctga tgaagaacag cgcaacaaa tttattcagt ctctgaagga cgatccttct   120
caatccacca acgtactggg cgaagcgaag aaactgaacg aatctcaggc tccgaag     177
```

<210> SEQ ID NO 54
<211> LENGTH: 174
<212> TYPE: DNA
<213> ORGANISM: Staphylococcus aureus

<400> SEQUENCE: 54

```
gtagacaaca aattcaataa agaacagcag aacgctttct atgaaatcct gcacctgccg    60
aacctgaacg aagaacagcg taacaaattt atccagtccc tgaaagacga cccgagccag   120
agcgcaaatc tgctggcgga agcgaaaaag ctgaacgatg cccaggcgcc gaaa         174
```

<210> SEQ ID NO 55

```
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Lys Phe Asn Lys Glu Gln Gln Asn Ala Phe Tyr Glu Ile Leu His Leu
1               5                   10                  15

Pro Asn Leu Asn Glu Glu Gln Arg Asn Lys Phe Ile Gln Ser Leu Lys
            20                  25                  30

Asp Asp Pro Ser Gln Ser Ala Asn Leu Leu Ala Glu Ala Lys Lys Leu
        35                  40                  45

Asn Asp Ala Gln Ala Pro Lys
    50                  55

<210> SEQ ID NO 56
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Lys Phe Asn Lys Glu Gln Gln Asn Ala Phe Tyr Glu Ile Leu His Leu
1               5                   10                  15

Pro Asn Leu Thr Glu Glu Gln Arg Asn Lys Phe Ile Gln Ser Leu Lys
            20                  25                  30

Asp Asp Pro Ser Val Ser Lys Glu Ile Leu Ala Glu Ala Lys Lys Leu
        35                  40                  45

Asn Asp Ala Gln Ala Pro Lys
    50                  55

<210> SEQ ID NO 57
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Lys Phe Asn Lys Glu Gln Gln Asn Ala Phe Tyr Glu Ile Leu His Leu
1               5                   10                  15

Pro Asn Leu Asn Glu Glu Gln Arg Asn Lys Phe Ile Gln Ser Leu Lys
            20                  25                  30

Asp Asp Pro Ser Gln Ser Ala Asn Leu Leu Ala Glu Ala Lys Lys Leu
        35                  40                  45

Asn Asp Ala Gln Ala Pro Lys
    50                  55

<210> SEQ ID NO 58
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Lys Phe Asn Lys Glu Gln Gln Asn Ala Phe Tyr Glu Ile Leu His Leu
```

```
1               5                   10                  15
Pro Asn Leu Asn Glu Glu Gln Arg Asn Lys Phe Ile Gln Ser Leu Lys
            20                  25                  30

Asp Asp Pro Ser Gln Ser Ala Asn Leu Leu Ala Glu Ala Lys Lys Leu
        35                  40                  45

Asn Asp Ala Gln Ala Pro Lys Lys Phe Asn Lys Glu Gln Gln Asn Ala
    50                  55                  60

Phe Tyr Glu Ile Leu His Leu Pro Asn Leu Asn Glu Glu Gln Arg Asn
65                  70                  75                  80

Lys Phe Ile Gln Ser Leu Lys Asp Asp Pro Ser Gln Ser Ala Asn Leu
                85                  90                  95

Leu Ala Glu Ala Lys Lys Leu Asn Asp Ala Gln Ala Pro Lys
            100                 105                 110

<210> SEQ ID NO 59
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Lys Phe Asn Lys Glu Gln Gln Asn Ala Phe Tyr Glu Ile Leu His Leu
1               5                   10                  15

Pro Asn Leu Thr Glu Glu Gln Arg Asn Lys Phe Ile Gln Ser Leu Lys
            20                  25                  30

Asp Asp Pro Ser Val Ser Lys Glu Ile Leu Ala Glu Ala Lys Lys Leu
        35                  40                  45

Asn Asp Ala Gln Ala Pro Lys Lys Phe Asn Lys Glu Gln Gln Asn Ala
    50                  55                  60

Phe Tyr Glu Ile Leu His Leu Pro Asn Leu Thr Glu Glu Gln Arg Asn
65                  70                  75                  80

Lys Phe Ile Gln Ser Leu Lys Asp Asp Pro Ser Val Ser Lys Glu Ile
                85                  90                  95

Leu Ala Glu Ala Lys Lys Leu Asn Asp Ala Gln Ala Pro Lys
            100                 105                 110

<210> SEQ ID NO 60
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Lys Phe Asn Lys Glu Gln Gln Asn Ala Phe Tyr Glu Ile Leu His Leu
1               5                   10                  15

Pro Asn Leu Asn Glu Glu Gln Arg Asn Lys Phe Ile Gln Ser Leu Lys
            20                  25                  30

Asp Asp Pro Ser Gln Ser Ala Asn Leu Leu Ala Glu Ala Lys Lys Leu
        35                  40                  45

Asn Asp Ala Gln Ala Pro Lys Lys Phe Asn Lys Glu Gln Gln Asn Ala
    50                  55                  60

Phe Tyr Glu Ile Leu His Leu Pro Asn Leu Asn Glu Glu Gln Arg Asn
65                  70                  75                  80

Lys Phe Ile Gln Ser Leu Lys Asp Asp Pro Ser Gln Ser Ala Asn Leu
```

```
                    85                  90                  95

Leu Ala Glu Ala Lys Lys Leu Asn Asp Ala Gln Ala Pro Lys
                100                 105                 110

<210> SEQ ID NO 61
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Lys Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys Phe Asn Lys Glu Gln
    50                  55                  60

Gln Asn Ala Phe Tyr Glu Ile Leu His Leu Pro Asn Leu Asn Glu Glu
65                  70                  75                  80

Gln Arg Asn Lys Phe Ile Gln Ser Leu Lys Asp Asp Pro Ser Gln Ser
                85                  90                  95

Ala Asn Leu Leu Ala Glu Ala Lys Lys Leu Asn Asp Ala Gln Ala Pro
                100                 105                 110

Lys

<210> SEQ ID NO 62
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Lys Phe Ile Gln
                20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys Phe Asn Lys Glu Gln
    50                  55                  60

Gln Asn Ala Phe Tyr Glu Ile Leu His Leu Pro Asn Leu Thr Glu Glu
65                  70                  75                  80

Gln Arg Asn Lys Phe Ile Gln Ser Leu Lys Asp Asp Pro Ser Val Ser
                85                  90                  95

Lys Glu Ile Leu Ala Glu Ala Lys Lys Leu Asn Asp Ala Gln Ala Pro
                100                 105                 110

Lys

<210> SEQ ID NO 63
<211> LENGTH: 113
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 63

```
Val Asp Asn Lys Phe Asn Lys Glu Gln Gln Asn Ala Phe Tyr Glu Ile
1               5                   10                  15
Leu His Leu Pro Asn Leu Asn Glu Glu Gln Arg Asn Lys Phe Ile Gln
            20                  25                  30
Ser Leu Lys Asp Asp Pro Ser Gln Ser Ala Asn Leu Leu Ala Glu Ala
        35                  40                  45
Lys Lys Leu Asn Asp Ala Gln Ala Pro Lys Lys Phe Asn Lys Glu Gln
    50                  55                  60
Gln Asn Ala Phe Tyr Glu Ile Leu His Leu Pro Asn Leu Asn Glu Glu
65                  70                  75                  80
Gln Arg Asn Lys Phe Ile Gln Ser Leu Lys Asp Asp Pro Ser Gln Ser
                85                  90                  95
Ala Asn Leu Leu Ala Glu Ala Lys Lys Leu Asn Asp Ala Gln Ala Pro
            100                 105                 110
Lys
```

<210> SEQ ID NO 64
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Lys Phe Asn Lys Glu Gln Gln Asn Ala Phe Tyr Glu Ile Leu His Leu
1               5                   10                  15
Pro Asn Leu Asn Glu Glu Gln Arg Asn Lys Phe Ile Gln Ser Leu Lys
            20                  25                  30
Asp Asp Pro Ser Gln Ser Ala Asn Leu Leu Ala Glu Ala Lys Lys Leu
        35                  40                  45
Asn Asp Ala Gln Ala Pro Lys Lys Phe Asn Lys Glu Gln Gln Asn Ala
    50                  55                  60
Phe Tyr Glu Ile Leu His Leu Pro Asn Leu Asn Glu Glu Gln Arg Asn
65                  70                  75                  80
Lys Phe Ile Gln Ser Leu Lys Asp Asp Pro Ser Gln Ser Ala Asn Leu
                85                  90                  95
Leu Ala Glu Ala Lys Lys Leu Asn Asp Ala Gln Ala Pro Lys Lys Phe
            100                 105                 110
Asn Lys Glu Gln Gln Asn Ala Phe Tyr Glu Ile Leu His Leu Pro Asn
        115                 120                 125
Leu Asn Glu Glu Gln Arg Asn Lys Phe Ile Gln Ser Leu Lys Asp Asp
    130                 135                 140
Pro Ser Gln Ser Ala Asn Leu Leu Ala Glu Ala Lys Lys Leu Asn Asp
145                 150                 155                 160
Ala Gln Ala Pro Lys Lys Phe Asn Lys Glu Gln Gln Asn Ala Phe Tyr
                165                 170                 175
Glu Ile Leu His Leu Pro Asn Leu Glu Glu Gln Arg Asn Lys Phe
            180                 185                 190
Ile Gln Ser Leu Lys Asp Asp Pro Ser Gln Ser Ala Asn Leu Leu Ala
        195                 200                 205
Glu Ala Lys Lys Leu Asn Asp Ala Gln Ala Pro Lys Lys Phe Asn Lys
```

```
            210                 215                 220
Glu Gln Gln Asn Ala Phe Tyr Glu Ile Leu His Leu Pro Asn Leu Asn
225                 230                 235                 240

Glu Glu Gln Arg Asn Lys Phe Ile Gln Ser Leu Lys Asp Asp Pro Ser
            245                 250                 255

Gln Ser Ala Asn Leu Leu Ala Glu Ala Lys Lys Leu Asn Asp Ala Gln
                260                 265                 270

Ala Pro Lys
        275

<210> SEQ ID NO 65
<211> LENGTH: 275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Lys Phe Asn Lys Glu Gln Gln Asn Ala Phe Tyr Glu Ile Leu His Leu
1               5                   10                  15

Pro Asn Leu Thr Glu Glu Gln Arg Asn Lys Phe Ile Gln Ser Leu Lys
            20                  25                  30

Asp Asp Pro Ser Val Ser Lys Glu Ile Leu Ala Glu Ala Lys Lys Leu
        35                  40                  45

Asn Asp Ala Gln Ala Pro Lys Lys Phe Asn Lys Glu Gln Gln Asn Ala
    50                  55                  60

Phe Tyr Glu Ile Leu His Leu Pro Asn Leu Thr Glu Glu Gln Arg Asn
65                  70                  75                  80

Lys Phe Ile Gln Ser Leu Lys Asp Asp Pro Ser Val Ser Lys Glu Ile
                85                  90                  95

Leu Ala Glu Ala Lys Lys Leu Asn Asp Ala Gln Ala Pro Lys Lys Phe
            100                 105                 110

Asn Lys Glu Gln Gln Asn Ala Phe Tyr Glu Ile Leu His Leu Pro Asn
        115                 120                 125

Leu Thr Glu Glu Gln Arg Asn Lys Phe Ile Gln Ser Leu Lys Asp Asp
    130                 135                 140

Pro Ser Val Ser Lys Glu Ile Leu Ala Glu Ala Lys Lys Leu Asn Asp
145                 150                 155                 160

Ala Gln Ala Pro Lys Lys Phe Asn Lys Glu Gln Gln Asn Ala Phe Tyr
                165                 170                 175

Glu Ile Leu His Leu Pro Asn Leu Thr Glu Glu Gln Arg Asn Lys Phe
            180                 185                 190

Ile Gln Ser Leu Lys Asp Asp Pro Ser Val Ser Lys Glu Ile Leu Ala
        195                 200                 205

Glu Ala Lys Lys Leu Asn Asp Ala Gln Ala Pro Lys Lys Phe Asn Lys
    210                 215                 220

Glu Gln Gln Asn Ala Phe Tyr Glu Ile Leu His Leu Pro Asn Leu Thr
225                 230                 235                 240

Glu Glu Gln Arg Asn Lys Phe Ile Gln Ser Leu Lys Asp Asp Pro Ser
                245                 250                 255

Val Ser Lys Glu Ile Leu Ala Glu Ala Lys Lys Leu Asn Asp Ala Gln
            260                 265                 270

Ala Pro Lys
        275
```

<210> SEQ ID NO 66
<211> LENGTH: 275
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Lys Phe Asn Lys Glu Gln Gln Asn Ala Phe Tyr Glu Ile Leu His Leu
 1               5                  10                  15

Pro Asn Leu Asn Glu Glu Gln Arg Asn Lys Phe Ile Gln Ser Leu Lys
            20                  25                  30

Asp Asp Pro Ser Gln Ser Ala Asn Leu Leu Ala Glu Ala Lys Lys Leu
        35                  40                  45

Asn Asp Ala Gln Ala Pro Lys Lys Phe Asn Lys Glu Gln Gln Asn Ala
    50                  55                  60

Phe Tyr Glu Ile Leu His Leu Pro Asn Leu Asn Glu Glu Gln Arg Asn
65                  70                  75                  80

Lys Phe Ile Gln Ser Leu Lys Asp Asp Pro Ser Gln Ser Ala Asn Leu
                85                  90                  95

Leu Ala Glu Ala Lys Lys Leu Asn Asp Ala Gln Ala Pro Lys Lys Phe
            100                 105                 110

Asn Lys Glu Gln Gln Asn Ala Phe Tyr Glu Ile Leu His Leu Pro Asn
        115                 120                 125

Leu Asn Glu Glu Gln Arg Asn Lys Phe Ile Gln Ser Leu Lys Asp Asp
    130                 135                 140

Pro Ser Gln Ser Ala Asn Leu Leu Ala Glu Ala Lys Lys Leu Asn Asp
145                 150                 155                 160

Ala Gln Ala Pro Lys Lys Phe Asn Lys Glu Gln Gln Asn Ala Phe Tyr
                165                 170                 175

Glu Ile Leu His Leu Pro Asn Leu Asn Glu Glu Gln Arg Asn Lys Phe
            180                 185                 190

Ile Gln Ser Leu Lys Asp Asp Pro Ser Gln Ser Ala Asn Leu Leu Ala
        195                 200                 205

Glu Ala Lys Lys Leu Asn Asp Ala Gln Ala Pro Lys Lys Phe Asn Lys
    210                 215                 220

Glu Gln Gln Asn Ala Phe Tyr Glu Ile Leu His Leu Pro Asn Leu Asn
225                 230                 235                 240

Glu Glu Gln Arg Asn Lys Phe Ile Gln Ser Leu Lys Asp Asp Pro Ser
                245                 250                 255

Gln Ser Ala Asn Leu Leu Ala Glu Ala Lys Lys Leu Asn Asp Ala Gln
            260                 265                 270

Ala Pro Lys
        275
```

<210> SEQ ID NO 67
<211> LENGTH: 278
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

```
Ala Asp Asn Lys Phe Asn Lys Glu Gln Gln Asn Ala Phe Tyr Glu Ile
 1               5                  10                  15
```

```
Leu His Leu Pro Asn Leu Asn Glu Glu Gln Arg Asn Lys Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys Lys Phe Asn Lys Glu Gln
 50                  55                  60

Gln Asn Ala Phe Tyr Glu Ile Leu His Leu Pro Asn Leu Asn Glu Glu
 65                  70                  75                  80

Gln Arg Asn Lys Phe Ile Gln Ser Leu Lys Asp Asp Pro Ser Gln Ser
                 85                  90                  95

Ala Asn Leu Leu Ala Glu Ala Lys Lys Leu Asn Asp Ala Gln Ala Pro
            100                 105                 110

Lys Lys Phe Asn Lys Glu Gln Gln Asn Ala Phe Tyr Glu Ile Leu His
            115                 120                 125

Leu Pro Asn Leu Asn Glu Glu Gln Arg Asn Lys Phe Ile Gln Ser Leu
            130                 135                 140

Lys Asp Asp Pro Ser Gln Ser Ala Asn Leu Leu Ala Glu Ala Lys Lys
145                 150                 155                 160

Leu Asn Asp Ala Gln Ala Pro Lys Lys Phe Asn Lys Glu Gln Gln Asn
                165                 170                 175

Ala Phe Tyr Glu Ile Leu His Leu Pro Asn Leu Asn Glu Glu Gln Arg
            180                 185                 190

Asn Lys Phe Ile Gln Ser Leu Lys Asp Asp Pro Ser Gln Ser Ala Asn
            195                 200                 205

Leu Leu Ala Glu Ala Lys Lys Leu Asn Asp Ala Gln Ala Pro Lys Lys
            210                 215                 220

Phe Asn Lys Glu Gln Gln Asn Ala Phe Tyr Glu Ile Leu His Leu Pro
225                 230                 235                 240

Asn Leu Asn Glu Glu Gln Arg Asn Lys Phe Ile Gln Ser Leu Lys Asp
                245                 250                 255

Asp Pro Ser Gln Ser Ala Asn Leu Leu Ala Glu Ala Lys Lys Leu Asn
            260                 265                 270

Asp Ala Gln Ala Pro Lys
            275

<210> SEQ ID NO 68
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Lys Phe Ile Gln
                20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys Lys Phe Asn Lys Glu Gln
 50                  55                  60

Gln Asn Ala Phe Tyr Glu Ile Leu His Leu Pro Asn Leu Thr Glu Glu
 65                  70                  75                  80

Gln Arg Asn Lys Phe Ile Gln Ser Leu Lys Asp Asp Pro Ser Val Ser
                 85                  90                  95
```

```
Lys Glu Ile Leu Ala Glu Ala Lys Lys Leu Asn Asp Ala Gln Ala Pro
            100                 105                 110
Lys Lys Phe Asn Lys Glu Gln Gln Asn Ala Phe Tyr Glu Ile Leu His
        115                 120                 125
Leu Pro Asn Leu Thr Glu Glu Gln Arg Asn Lys Phe Ile Gln Ser Leu
    130                 135                 140
Lys Asp Asp Pro Ser Val Ser Lys Glu Ile Leu Ala Glu Ala Lys Lys
145                 150                 155                 160
Leu Asn Asp Ala Gln Ala Pro Lys Lys Phe Asn Lys Glu Gln Gln Asn
                165                 170                 175
Ala Phe Tyr Glu Ile Leu His Leu Pro Asn Leu Thr Glu Glu Gln Arg
            180                 185                 190
Asn Lys Phe Ile Gln Ser Leu Lys Asp Asp Pro Ser Val Ser Lys Glu
        195                 200                 205
Ile Leu Ala Glu Ala Lys Lys Leu Asn Asp Ala Gln Ala Pro Lys Lys
    210                 215                 220
Phe Asn Lys Glu Gln Gln Asn Ala Phe Tyr Glu Ile Leu His Leu Pro
225                 230                 235                 240
Asn Leu Thr Glu Glu Gln Arg Asn Lys Phe Ile Gln Ser Leu Lys Asp
                245                 250                 255
Asp Pro Ser Val Ser Lys Glu Ile Leu Ala Glu Ala Lys Lys Leu Asn
            260                 265                 270
Asp Ala Gln Ala Pro Lys
            275

<210> SEQ ID NO 69
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Val Asp Asn Lys Phe Asn Lys Glu Gln Gln Asn Ala Phe Tyr Glu Ile
1               5                   10                  15
Leu His Leu Pro Asn Leu Asn Glu Glu Gln Arg Asn Lys Phe Ile Gln
            20                  25                  30
Ser Leu Lys Asp Asp Pro Ser Gln Ser Ala Asn Leu Leu Ala Glu Ala
        35                  40                  45
Lys Lys Leu Asn Asp Ala Gln Ala Pro Lys Lys Phe Asn Lys Glu Gln
    50                  55                  60
Gln Asn Ala Phe Tyr Glu Ile Leu His Leu Pro Asn Leu Asn Glu Glu
65                  70                  75                  80
Gln Arg Asn Lys Phe Ile Gln Ser Leu Lys Asp Asp Pro Ser Gln Ser
                85                  90                  95
Ala Asn Leu Leu Ala Glu Ala Lys Lys Leu Asn Asp Ala Gln Ala Pro
            100                 105                 110
Lys Lys Phe Asn Lys Glu Gln Gln Asn Ala Phe Tyr Glu Ile Leu His
        115                 120                 125
Leu Pro Asn Leu Asn Glu Glu Gln Arg Asn Lys Phe Ile Gln Ser Leu
    130                 135                 140
Lys Asp Asp Pro Ser Gln Ser Ala Asn Leu Leu Ala Glu Ala Lys Lys
145                 150                 155                 160
Leu Asn Asp Ala Gln Ala Pro Lys Lys Phe Asn Lys Glu Gln Gln Asn
```

```
                165                 170                 175
Ala Phe Tyr Glu Ile Leu His Leu Pro Asn Leu Asn Glu Glu Gln Arg
            180                 185                 190

Asn Lys Phe Ile Gln Ser Leu Lys Asp Asp Pro Ser Gln Ser Ala Asn
        195                 200                 205

Leu Leu Ala Glu Ala Lys Lys Leu Asn Asp Ala Gln Ala Pro Lys Lys
    210                 215                 220

Phe Asn Lys Glu Gln Gln Asn Ala Phe Tyr Glu Ile Leu His Leu Pro
225                 230                 235                 240

Asn Leu Asn Glu Glu Gln Arg Asn Lys Phe Ile Gln Ser Leu Lys Asp
                245                 250                 255

Asp Pro Ser Gln Ser Ala Asn Leu Leu Ala Glu Ala Lys Lys Leu Asn
            260                 265                 270

Asp Ala Gln Ala Pro Lys
        275

<210> SEQ ID NO 70
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Phe Asn Lys Glu Gln Gln Asn Ala Phe Tyr Glu Ile Leu His Leu Pro
1               5                   10                  15

Asn Leu Asn Glu Glu Gln Arg Asn Lys Phe Ile Gln Ser Leu Lys Asp
            20                  25                  30

Asp Pro Ser Gln Ser Ala Asn Leu Leu Ala Glu Ala Lys Lys Leu Asn
        35                  40                  45

Asp Ala Gln Ala Pro Lys
    50

<210> SEQ ID NO 71
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Phe Asn Lys Glu Gln Gln Asn Ala Phe Tyr Glu Ile Leu His Leu Pro
1               5                   10                  15

Asn Leu Thr Glu Glu Gln Arg Asn Lys Phe Ile Gln Ser Leu Lys Asp
            20                  25                  30

Asp Pro Ser Val Ser Lys Glu Ile Leu Ala Glu Ala Lys Lys Leu Asn
        35                  40                  45

Asp Ala Gln Ala Pro Lys
    50

<210> SEQ ID NO 72
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72
```

```
Phe Asn Lys Glu Gln Gln Asn Ala Phe Tyr Glu Ile Leu His Leu Pro
1               5                   10                  15

Asn Leu Asn Glu Glu Gln Arg Asn Lys Phe Ile Gln Ser Leu Lys Asp
            20                  25                  30

Asp Pro Ser Gln Ser Ala Asn Leu Leu Ala Glu Ala Lys Lys Leu Asn
        35                  40                  45

Asp Ala Gln Ala Pro Lys
    50

<210> SEQ ID NO 73
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Phe Asn Lys Glu Gln Gln Asn Ala Phe Tyr Glu Ile Leu His Leu Pro
1               5                   10                  15

Asn Leu Asn Glu Glu Gln Arg Asn Lys Phe Ile Gln Ser Leu Lys Asp
            20                  25                  30

Asp Pro Ser Gln Ser Ala Asn Leu Leu Ala Glu Ala Lys Lys Leu Asn
        35                  40                  45

Asp Ala Gln Ala Pro Lys Phe Asn Lys Glu Gln Gln Asn Ala Phe Tyr
    50                  55                  60

Glu Ile Leu His Leu Pro Asn Leu Asn Glu Glu Gln Arg Asn Lys Phe
65                  70                  75                  80

Ile Gln Ser Leu Lys Asp Asp Pro Ser Gln Ser Ala Asn Leu Leu Ala
                85                  90                  95

Glu Ala Lys Lys Leu Asn Asp Ala Gln Ala Pro Lys
            100                 105

<210> SEQ ID NO 74
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Phe Asn Lys Glu Gln Gln Asn Ala Phe Tyr Glu Ile Leu His Leu Pro
1               5                   10                  15

Asn Leu Thr Glu Glu Gln Arg Asn Lys Phe Ile Gln Ser Leu Lys Asp
            20                  25                  30

Asp Pro Ser Val Ser Lys Glu Ile Leu Ala Glu Ala Lys Lys Leu Asn
        35                  40                  45

Asp Ala Gln Ala Pro Lys Phe Asn Lys Glu Gln Gln Asn Ala Phe Tyr
    50                  55                  60

Glu Ile Leu His Leu Pro Asn Leu Thr Glu Glu Gln Arg Asn Lys Phe
65                  70                  75                  80

Ile Gln Ser Leu Lys Asp Asp Pro Ser Val Ser Lys Glu Ile Leu Ala
                85                  90                  95

Glu Ala Lys Lys Leu Asn Asp Ala Gln Ala Pro Lys
            100                 105

<210> SEQ ID NO 75
```

<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Phe Asn Lys Glu Gln Gln Asn Ala Phe Tyr Glu Ile Leu His Leu Pro
1               5                   10                  15

Asn Leu Asn Glu Glu Gln Arg Asn Lys Phe Ile Gln Ser Leu Lys Asp
            20                  25                  30

Asp Pro Ser Gln Ser Ala Asn Leu Leu Ala Glu Ala Lys Lys Leu Asn
        35                  40                  45

Asp Ala Gln Ala Pro Lys Phe Asn Lys Glu Gln Gln Asn Ala Phe Tyr
    50                  55                  60

Glu Ile Leu His Leu Pro Asn Leu Asn Glu Glu Gln Arg Asn Lys Phe
65                  70                  75                  80

Ile Gln Ser Leu Lys Asp Asp Pro Ser Gln Ser Ala Asn Leu Leu Ala
                85                  90                  95

Glu Ala Lys Lys Leu Asn Asp Ala Gln Ala Pro Lys
            100                 105

<210> SEQ ID NO 76
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Lys Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Phe Asn Lys Glu Gln Gln
    50                  55                  60

Asn Ala Phe Tyr Glu Ile Leu His Leu Pro Asn Leu Asn Glu Glu Gln
65                  70                  75                  80

Arg Asn Lys Phe Ile Gln Ser Leu Lys Asp Asp Pro Ser Gln Ser Ala
                85                  90                  95

Asn Leu Leu Ala Glu Ala Lys Lys Leu Asn Asp Ala Gln Ala Pro Lys
            100                 105                 110

<210> SEQ ID NO 77
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Lys Phe Ile Gln
            20                  25                  30

Ser Leu Lys Asp Asp Pro Ser Val Ser Lys Glu Ile Leu Ala Glu Ala
                35                  40                  45

Lys Lys Leu Asn Asp Ala Gln Ala Pro Lys Phe Asn Lys Glu Gln Gln
 50                  55                  60

Asn Ala Phe Tyr Glu Ile Leu His Leu Pro Asn Leu Thr Glu Glu Gln
65                  70                  75                  80

Arg Asn Lys Phe Ile Gln Ser Leu Lys Asp Asp Pro Ser Val Ser Lys
                85                  90                  95

Glu Ile Leu Ala Glu Ala Lys Lys Leu Asn Asp Ala Gln Ala Pro Lys
            100                 105                 110

<210> SEQ ID NO 78
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Lys Phe Ile Gln
                20                  25                  30

Ser Leu Lys Asp Asp Pro Ser Gln Ser Ala Asn Leu Leu Ala Glu Ala
                35                  40                  45

Lys Lys Leu Asn Asp Ala Gln Ala Pro Lys Phe Asn Lys Glu Gln Gln
 50                  55                  60

Asn Ala Phe Tyr Glu Ile Leu His Leu Pro Asn Leu Asn Glu Glu Gln
65                  70                  75                  80

Arg Asn Lys Phe Ile Gln Ser Leu Lys Asp Asp Pro Ser Gln Ser Ala
                85                  90                  95

Asn Leu Leu Ala Glu Ala Lys Lys Leu Asn Asp Ala Gln Ala Pro Lys
            100                 105                 110

<210> SEQ ID NO 79
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Phe Asn Lys Glu Gln Gln Asn Ala Phe Tyr Glu Ile Leu His Leu Pro
1               5                   10                  15

Asn Leu Asn Glu Glu Gln Arg Asn Lys Phe Ile Gln Ser Leu Lys Asp
                20                  25                  30

Asp Pro Ser Gln Ser Ala Asn Leu Leu Ala Glu Ala Lys Lys Leu Asn
                35                  40                  45

Asp Ala Gln Ala Pro Lys Phe Asn Lys Glu Gln Gln Asn Ala Phe Tyr
 50                  55                  60

Glu Ile Leu His Leu Pro Asn Leu Asn Glu Glu Gln Arg Asn Lys Phe
65                  70                  75                  80

Ile Gln Ser Leu Lys Asp Asp Pro Ser Gln Ser Ala Asn Leu Leu Ala
                85                  90                  95

Glu Ala Lys Lys Leu Asn Asp Ala Gln Ala Pro Lys Phe Asn Lys Glu
            100                 105                 110

```
Gln Gln Asn Ala Phe Tyr Glu Ile Leu His Leu Pro Asn Leu Asn Glu
            115                 120                 125

Glu Gln Arg Asn Lys Phe Ile Gln Ser Leu Lys Asp Asp Pro Ser Gln
        130                 135                 140

Ser Ala Asn Leu Leu Ala Glu Ala Lys Lys Leu Asn Asp Ala Gln Ala
145                 150                 155                 160

Pro Lys Phe Asn Lys Glu Gln Gln Asn Ala Phe Tyr Glu Ile Leu His
                165                 170                 175

Leu Pro Asn Leu Asn Glu Gln Arg Asn Lys Phe Ile Gln Ser Leu
            180                 185                 190

Lys Asp Asp Pro Ser Gln Ser Ala Asn Leu Leu Ala Glu Ala Lys Lys
        195                 200                 205

Leu Asn Asp Ala Gln Ala Pro Lys Phe Asn Lys Glu Gln Gln Asn Ala
    210                 215                 220

Phe Tyr Glu Ile Leu His Leu Pro Asn Leu Asn Glu Gln Arg Asn
225                 230                 235                 240

Lys Phe Ile Gln Ser Leu Lys Asp Asp Pro Ser Gln Ser Ala Asn Leu
                245                 250                 255

Leu Ala Glu Ala Lys Lys Leu Asn Asp Ala Gln Ala Pro Lys
        260                 265                 270

<210> SEQ ID NO 80
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Phe Asn Lys Glu Gln Gln Asn Ala Phe Tyr Glu Ile Leu His Leu Pro
1               5                   10                  15

Asn Leu Thr Glu Glu Gln Arg Asn Lys Phe Ile Gln Ser Leu Lys Asp
            20                  25                  30

Asp Pro Ser Val Ser Lys Glu Ile Leu Ala Glu Ala Lys Lys Leu Asn
        35                  40                  45

Asp Ala Gln Ala Pro Lys Phe Asn Lys Glu Gln Gln Asn Ala Phe Tyr
    50                  55                  60

Glu Ile Leu His Leu Pro Asn Leu Thr Glu Glu Gln Arg Asn Lys Phe
65                  70                  75                  80

Ile Gln Ser Leu Lys Asp Asp Pro Ser Val Ser Lys Glu Ile Leu Ala
                85                  90                  95

Glu Ala Lys Lys Leu Asn Asp Ala Gln Ala Pro Lys Phe Asn Lys Glu
            100                 105                 110

Gln Gln Asn Ala Phe Tyr Glu Ile Leu His Leu Pro Asn Leu Thr Glu
        115                 120                 125

Glu Gln Arg Asn Lys Phe Ile Gln Ser Leu Lys Asp Asp Pro Ser Val
    130                 135                 140

Ser Lys Glu Ile Leu Ala Glu Ala Lys Lys Leu Asn Asp Ala Gln Ala
145                 150                 155                 160

Pro Lys Phe Asn Lys Glu Gln Gln Asn Ala Phe Tyr Glu Ile Leu His
                165                 170                 175

Leu Pro Asn Leu Thr Glu Glu Gln Arg Asn Lys Phe Ile Gln Ser Leu
            180                 185                 190

Lys Asp Asp Pro Ser Val Ser Lys Glu Ile Leu Ala Glu Ala Lys Lys
        195                 200                 205
```

Leu Asn Asp Ala Gln Ala Pro Lys Phe Asn Lys Glu Gln Gln Asn Ala
    210                 215                 220

Phe Tyr Glu Ile Leu His Leu Pro Asn Leu Thr Glu Gln Arg Asn
225                 230                 235                 240

Lys Phe Ile Gln Ser Leu Lys Asp Asp Pro Ser Val Ser Lys Glu Ile
                245                 250                 255

Leu Ala Glu Ala Lys Lys Leu Asn Asp Ala Gln Ala Pro Lys
            260                 265                 270

<210> SEQ ID NO 81
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Phe Asn Lys Glu Gln Gln Asn Ala Phe Tyr Glu Ile Leu His Leu Pro
1               5                   10                  15

Asn Leu Asn Glu Glu Gln Arg Asn Lys Phe Ile Gln Ser Leu Lys Asp
            20                  25                  30

Asp Pro Ser Gln Ser Ala Asn Leu Leu Ala Glu Ala Lys Lys Leu Asn
        35                  40                  45

Asp Ala Gln Ala Pro Lys Phe Asn Lys Glu Gln Gln Asn Ala Phe Tyr
    50                  55                  60

Glu Ile Leu His Leu Pro Asn Leu Asn Glu Glu Gln Arg Asn Lys Phe
65                  70                  75                  80

Ile Gln Ser Leu Lys Asp Asp Pro Ser Gln Ser Ala Asn Leu Leu Ala
                85                  90                  95

Glu Ala Lys Lys Leu Asn Asp Ala Gln Ala Pro Lys Phe Asn Lys Glu
            100                 105                 110

Gln Gln Asn Ala Phe Tyr Glu Ile Leu His Leu Pro Asn Leu Asn Glu
        115                 120                 125

Glu Gln Arg Asn Lys Phe Ile Gln Ser Leu Lys Asp Asp Pro Ser Gln
    130                 135                 140

Ser Ala Asn Leu Leu Ala Glu Ala Lys Lys Leu Asn Asp Ala Gln Ala
145                 150                 155                 160

Pro Lys Phe Asn Lys Glu Gln Gln Asn Ala Phe Tyr Glu Ile Leu His
                165                 170                 175

Leu Pro Asn Leu Asn Glu Glu Gln Arg Asn Lys Phe Ile Gln Ser Leu
            180                 185                 190

Lys Asp Asp Pro Ser Gln Ser Ala Asn Leu Leu Ala Glu Ala Lys Lys
        195                 200                 205

Leu Asn Asp Ala Gln Ala Pro Lys Phe Asn Lys Glu Gln Gln Asn Ala
    210                 215                 220

Phe Tyr Glu Ile Leu His Leu Pro Asn Leu Asn Glu Glu Gln Arg Asn
225                 230                 235                 240

Lys Phe Ile Gln Ser Leu Lys Asp Asp Pro Ser Gln Ser Ala Asn Leu
                245                 250                 255

Leu Ala Glu Ala Lys Lys Leu Asn Asp Ala Gln Ala Pro Lys
            260                 265                 270

<210> SEQ ID NO 82
<211> LENGTH: 274
<212> TYPE: PRT

-continued

<213> ORGANISM: Artificial Sequence
<220> FEATURE:
<223> OTHER INFORMATION: Description of Artificial Sequence: Synthetic
      polypeptide

<400> SEQUENCE: 82

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Lys Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Phe Asn Lys Glu Gln Gln
50                  55                  60

Asn Ala Phe Tyr Glu Ile Leu His Leu Pro Asn Leu Asn Glu Glu Gln
65                  70                  75                  80

Arg Asn Lys Phe Ile Gln Ser Leu Lys Asp Asp Pro Ser Gln Ser Ala
                85                  90                  95

Asn Leu Leu Ala Glu Ala Lys Lys Leu Asn Asp Ala Gln Ala Pro Lys
            100                 105                 110

Phe Asn Lys Glu Gln Gln Asn Ala Phe Tyr Glu Ile Leu His Leu Pro
        115                 120                 125

Asn Leu Asn Glu Glu Gln Arg Asn Lys Phe Ile Gln Ser Leu Lys Asp
130                 135                 140

Asp Pro Ser Gln Ser Ala Asn Leu Leu Ala Glu Ala Lys Lys Leu Asn
145                 150                 155                 160

Asp Ala Gln Ala Pro Lys Phe Asn Lys Glu Gln Gln Asn Ala Phe Tyr
                165                 170                 175

Glu Ile Leu His Leu Pro Asn Leu Asn Glu Glu Gln Arg Asn Lys Phe
            180                 185                 190

Ile Gln Ser Leu Lys Asp Asp Pro Ser Gln Ser Ala Asn Leu Leu Ala
        195                 200                 205

Glu Ala Lys Lys Leu Asn Asp Ala Gln Ala Pro Lys Phe Asn Lys Glu
210                 215                 220

Gln Gln Asn Ala Phe Tyr Glu Ile Leu His Leu Pro Asn Leu Asn Glu
225                 230                 235                 240

Glu Gln Arg Asn Lys Phe Ile Gln Ser Leu Lys Asp Asp Pro Ser Gln
                245                 250                 255

Ser Ala Asn Leu Leu Ala Glu Ala Lys Lys Leu Asn Asp Ala Gln Ala
            260                 265                 270

Pro Lys

<210> SEQ ID NO 83
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Lys Phe Ile Gln
            20                  25                  30

Ser Leu Lys Asp Asp Pro Ser Val Ser Lys Glu Ile Leu Ala Glu Ala
        35                  40                  45

-continued

```
Lys Lys Leu Asn Asp Ala Gln Ala Pro Lys Phe Asn Lys Glu Gln Gln
             50                  55                  60

Asn Ala Phe Tyr Glu Ile Leu His Leu Pro Asn Leu Thr Glu Glu Gln
 65                  70                  75                  80

Arg Asn Lys Phe Ile Gln Ser Leu Lys Asp Asp Pro Ser Val Ser Lys
                 85                  90                  95

Glu Ile Leu Ala Glu Ala Lys Lys Leu Asn Asp Ala Gln Ala Pro Lys
            100                 105                 110

Phe Asn Lys Glu Gln Gln Asn Ala Phe Tyr Glu Ile Leu His Leu Pro
            115                 120                 125

Asn Leu Thr Glu Glu Gln Arg Asn Lys Phe Ile Gln Ser Leu Lys Asp
            130                 135                 140

Asp Pro Ser Val Ser Lys Glu Ile Leu Ala Glu Ala Lys Lys Leu Asn
145                 150                 155                 160

Asp Ala Gln Ala Pro Lys Phe Asn Lys Glu Gln Gln Asn Ala Phe Tyr
                165                 170                 175

Glu Ile Leu His Leu Pro Asn Leu Thr Glu Glu Gln Arg Asn Lys Phe
            180                 185                 190

Ile Gln Ser Leu Lys Asp Asp Pro Ser Val Ser Lys Glu Ile Leu Ala
            195                 200                 205

Glu Ala Lys Lys Leu Asn Asp Ala Gln Ala Pro Lys Phe Asn Lys Glu
            210                 215                 220

Gln Gln Asn Ala Phe Tyr Glu Ile Leu His Leu Pro Asn Leu Thr Glu
225                 230                 235                 240

Glu Gln Arg Asn Lys Phe Ile Gln Ser Leu Lys Asp Asp Pro Ser Val
                245                 250                 255

Ser Lys Glu Ile Leu Ala Glu Ala Lys Lys Leu Asn Asp Ala Gln Ala
            260                 265                 270

Pro Lys

<210> SEQ ID NO 84
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Val Asp Asn Lys Phe Asn Lys Glu Gln Gln Asn Ala Phe Tyr Glu Ile
 1               5                  10                  15

Leu His Leu Pro Asn Leu Asn Glu Glu Gln Arg Asn Lys Phe Ile Gln
                 20                  25                  30

Ser Leu Lys Asp Asp Pro Ser Gln Ser Ala Asn Leu Leu Ala Glu Ala
             35                  40                  45

Lys Lys Leu Asn Asp Ala Gln Ala Pro Lys Phe Asn Lys Glu Gln Gln
             50                  55                  60

Asn Ala Phe Tyr Glu Ile Leu His Leu Pro Asn Leu Asn Glu Glu Gln
 65                  70                  75                  80

Arg Asn Lys Phe Ile Gln Ser Leu Lys Asp Asp Pro Ser Gln Ser Ala
                 85                  90                  95

Asn Leu Leu Ala Glu Ala Lys Lys Leu Asn Asp Ala Gln Ala Pro Lys
            100                 105                 110

Phe Asn Lys Glu Gln Gln Asn Ala Phe Tyr Glu Ile Leu His Leu Pro
            115                 120                 125
```

Asn Leu Asn Glu Glu Gln Arg Asn Lys Phe Ile Gln Ser Leu Lys Asp
            130                 135                 140

Asp Pro Ser Gln Ser Ala Asn Leu Leu Ala Glu Ala Lys Lys Leu Asn
145                 150                 155                 160

Asp Ala Gln Ala Pro Lys Phe Asn Lys Glu Gln Gln Asn Ala Phe Tyr
                165                 170                 175

Glu Ile Leu His Leu Pro Asn Leu Asn Glu Glu Gln Arg Asn Lys Phe
            180                 185                 190

Ile Gln Ser Leu Lys Asp Asp Pro Ser Gln Ser Ala Asn Leu Leu Ala
        195                 200                 205

Glu Ala Lys Lys Leu Asn Asp Ala Gln Ala Pro Lys Phe Asn Lys Glu
    210                 215                 220

Gln Gln Asn Ala Phe Tyr Glu Ile Leu His Leu Pro Asn Leu Asn Glu
225                 230                 235                 240

Glu Gln Arg Asn Lys Phe Ile Gln Ser Leu Lys Asp Asp Pro Ser Gln
                245                 250                 255

Ser Ala Asn Leu Leu Ala Glu Ala Lys Lys Leu Asn Asp Ala Gln Ala
            260                 265                 270

Pro Lys

<210> SEQ ID NO 85
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Val Asp Asn Lys Phe Asn
    50                  55                  60

Lys Glu Gln Gln Asn Ala Phe Tyr Glu Ile Leu His Leu Pro Asn Leu
65                  70                  75                  80

Asn Glu Glu Gln Arg Asn Ala Phe Ile Gln Ser Leu Lys Asp Asp Pro
                85                  90                  95

Ser Gln Ser Ala Asn Leu Leu Ala Glu Ala Lys Lys Leu Asn Asp Ala
            100                 105                 110

Gln Ala Pro Lys
        115

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
catcaccatc atcaccac                                                 18

```
<210> SEQ ID NO 87
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys Asp Asn Lys Phe Asn Lys
    50                  55                  60

Glu Gln Gln Asn Ala Phe Tyr Glu Ile Leu His Leu Pro Asn Leu Asn
65                  70                  75                  80

Glu Glu Gln Arg Asn Ala Phe Ile Gln Ser Leu Lys Asp Asp Pro Ser
                85                  90                  95

Gln Ser Ala Asn Leu Leu Ala Glu Ala Lys Lys Leu Asn Asp Ala Gln
            100                 105                 110

Ala Pro Lys
        115

<210> SEQ ID NO 88
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys Asn Lys Phe Asn Lys Glu
    50                  55                  60

Gln Gln Asn Ala Phe Tyr Glu Ile Leu His Leu Pro Asn Leu Asn Glu
65                  70                  75                  80

Glu Gln Arg Asn Ala Phe Ile Gln Ser Leu Lys Asp Asp Pro Ser Gln
                85                  90                  95

Ser Ala Asn Leu Leu Ala Glu Ala Lys Lys Leu Asn Asp Ala Gln Ala
            100                 105                 110

Pro Lys

<210> SEQ ID NO 89
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89
```

Ala Asp Asn Lys Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro Lys Phe Asn Lys Glu Gln Gln
50                  55                  60

Asn Ala Phe Tyr Glu Ile Leu Asn Met Pro Asn Leu Asn Glu Glu Gln
65                  70                  75                  80

Arg Asn Gly Phe Ile Gln Ser Leu Lys Asp Asp Pro Ser Gln Ser Ala
                85                  90                  95

Asn Leu Leu Ala Glu Ala Lys Lys Leu Asn Glu Ser Gln Ala Pro Lys
            100                 105                 110

<210> SEQ ID NO 90
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ala Asp Asn Lys Phe Asn Lys Asp Gln Gln Ser Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Thr Asn Val Leu Gly Glu Ala
        35                  40                  45

Lys Lys Leu Asn Glu Ser Gln Ala Pro Lys Phe Asn Lys Asp Gln Gln
50                  55                  60

Ser Ala Phe Tyr Glu Ile Leu Asn Met Pro Asn Leu Asn Glu Glu Gln
65                  70                  75                  80

Arg Asn Gly Phe Ile Gln Ser Leu Lys Asp Asp Pro Ser Gln Ser Thr
                85                  90                  95

Asn Val Leu Gly Glu Ala Lys Lys Leu Asn Glu Ser Gln Ala Pro Lys
            100                 105                 110

<210> SEQ ID NO 91
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Val Asp Asn Lys Phe Asn
50                  55                  60

Lys Glu Gln Gln Asn Ala Phe Tyr Glu Ile Leu His Leu Pro Asn Leu
65                  70                  75                  80

```
Asn Glu Glu Gln Arg Asn Ala Phe Ile Gln Ser Leu Lys Asp Asp Pro
                85                  90                  95

Ser Gln Ser Ala Asn Leu Leu Ala Glu Ala Lys Lys Leu Asn Asp Ala
            100                 105                 110

Gln Ala Pro Lys Val Asp Asn Lys Phe Asn Lys Glu Gln Gln Asn Ala
        115                 120                 125

Phe Tyr Glu Ile Leu His Leu Pro Asn Leu Asn Glu Glu Gln Arg Asn
    130                 135                 140

Ala Phe Ile Gln Ser Leu Lys Asp Asp Pro Ser Gln Ser Ala Asn Leu
145                 150                 155                 160

Leu Ala Glu Ala Lys Lys Leu Asn Asp Ala Gln Ala Pro Lys Val Asp
                165                 170                 175

Asn Lys Phe Asn Lys Glu Gln Gln Asn Ala Phe Tyr Glu Ile Leu His
            180                 185                 190

Leu Pro Asn Leu Asn Glu Glu Gln Arg Asn Ala Phe Ile Gln Ser Leu
        195                 200                 205

Lys Asp Asp Pro Ser Gln Ser Ala Asn Leu Leu Ala Glu Ala Lys Lys
    210                 215                 220

Leu Asn Asp Ala Gln Ala Pro Lys Val Asp Asn Lys Phe Asn Lys Glu
225                 230                 235                 240

Gln Gln Asn Ala Phe Tyr Glu Ile Leu His Leu Pro Asn Leu Asn Glu
                245                 250                 255

Glu Gln Arg Asn Ala Phe Ile Gln Ser Leu Lys Asp Asp Pro Ser Gln
            260                 265                 270

Ser Ala Asn Leu Leu Ala Glu Ala Lys Lys Leu Asn Asp Ala Gln Ala
        275                 280                 285

Pro Lys
    290

<210> SEQ ID NO 92
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys Ala Asp Asn Lys Phe Asn
    50                  55                  60

Lys Glu Gln Gln Asn Ala Phe Tyr Glu Ile Leu His Leu Pro Asn Leu
65                  70                  75                  80

Thr Glu Glu Gln Arg Asn Gly Phe Ile Gln Ser Leu Lys Asp Asp Pro
                85                  90                  95

Ser Val Ser Lys Glu Ile Leu Ala Glu Ala Lys Lys Leu Asn Asp Ala
            100                 105                 110

Gln Ala Pro Lys
        115

<210> SEQ ID NO 93
```

-continued

<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Ala Phe Asn Lys Glu Gln Gln Asn Ala Phe Tyr Glu Ile Leu His Leu
1               5                   10                  15

Pro Asn Leu Thr Glu Glu Gln Arg Asn Lys Phe Ile Gln Ser Leu Lys
            20                  25                  30

Asp Asp Pro Ser Val Ser Lys Glu Ile Leu Ala Glu Ala Lys Lys Leu
        35                  40                  45

Asn Asp Ala Gln Ala Pro Lys Phe Asn Lys Glu Gln Gln Asn Ala Phe
    50                  55                  60

Tyr Glu Ile Leu His Leu Pro Asn Leu Thr Glu Glu Gln Arg Asn Lys
65                  70                  75                  80

Phe Ile Gln Ser Leu Lys Asp Asp Pro Ser Val Ser Lys Glu Ile Leu
                85                  90                  95

Ala Glu Ala Lys Lys Leu Asn Asp Ala Gln Ala Pro Lys Phe Asn Lys
            100                 105                 110

Glu Gln Gln Asn Ala Phe Tyr Glu Ile Leu His Leu Pro Asn Leu Thr
        115                 120                 125

Glu Glu Gln Arg Asn Lys Phe Ile Gln Ser Leu Lys Asp Asp Pro Ser
    130                 135                 140

Val Ser Lys Glu Ile Leu Ala Glu Ala Lys Lys Leu Asn Asp Ala Gln
145                 150                 155                 160

Ala Pro Lys Phe Asn Lys Glu Gln Gln Asn Ala Phe Tyr Glu Ile Leu
                165                 170                 175

His Leu Pro Asn Leu Thr Glu Glu Gln Arg Asn Lys Phe Ile Gln Ser
            180                 185                 190

Leu Lys Asp Asp Pro Ser Val Ser Lys Glu Ile Leu Ala Glu Ala Lys
        195                 200                 205

Lys Leu Asn Asp Ala Gln Ala Pro Lys Phe Asn Lys Glu Gln Gln Asn
    210                 215                 220

Ala Phe Tyr Glu Ile Leu His Leu Pro Asn Leu Thr Glu Glu Gln Arg
225                 230                 235                 240

Asn Lys Phe Ile Gln Ser Leu Lys Asp Asp Pro Ser Val Ser Lys Glu
                245                 250                 255

Ile Leu Ala Glu Ala Lys Lys Leu Asn Asp Ala Gln Ala Pro Lys
            260                 265                 270

<210> SEQ ID NO 94
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Ala Phe Asn Lys Glu Gln Gln Asn Ala Phe Tyr Glu Ile Leu His Leu
1               5                   10                  15

Pro Asn Leu Thr Glu Glu Gln Arg Asn Gly Phe Ile Gln Ser Leu Lys
            20                  25                  30

Asp Asp Pro Ser Val Ser Lys Glu Ile Leu Ala Glu Ala Lys Lys Leu
        35                  40                  45

```
Asn Asp Ala Gln Ala Pro Lys Phe Asn Lys Glu Gln Gln Asn Ala Phe
         50                  55                  60

Tyr Glu Ile Leu His Leu Pro Asn Leu Thr Glu Gln Arg Asn Gly
 65              70                  75                  80

Phe Ile Gln Ser Leu Lys Asp Asp Pro Ser Val Ser Lys Glu Ile Leu
                 85                  90                  95

Ala Glu Ala Lys Lys Leu Asn Asp Ala Gln Ala Pro Lys Phe Asn Lys
            100                 105                 110

Glu Gln Gln Asn Ala Phe Tyr Glu Ile Leu His Leu Pro Asn Leu Thr
        115                 120                 125

Glu Glu Gln Arg Asn Gly Phe Ile Gln Ser Leu Lys Asp Asp Pro Ser
    130                 135                 140

Val Ser Lys Glu Ile Leu Ala Glu Ala Lys Lys Leu Asn Asp Ala Gln
145                 150                 155                 160

Ala Pro Lys Phe Asn Lys Glu Gln Gln Asn Ala Phe Tyr Glu Ile Leu
                165                 170                 175

His Leu Pro Asn Leu Thr Glu Glu Gln Arg Asn Gly Phe Ile Gln Ser
            180                 185                 190

Leu Lys Asp Asp Pro Ser Val Ser Lys Glu Ile Leu Ala Glu Ala Lys
        195                 200                 205

Lys Leu Asn Asp Ala Gln Ala Pro Lys Phe Asn Lys Glu Gln Gln Asn
    210                 215                 220

Ala Phe Tyr Glu Ile Leu His Leu Pro Asn Leu Thr Glu Glu Gln Arg
225                 230                 235                 240

Asn Gly Phe Ile Gln Ser Leu Lys Asp Asp Pro Ser Val Ser Lys Glu
                245                 250                 255

Ile Leu Ala Glu Ala Lys Lys Leu Asn Asp Ala Gln Ala Pro Lys
            260                 265                 270

<210> SEQ ID NO 95
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ala Asp Asn Lys Phe Asn Lys Glu Gln Gln Asn Ala Phe Tyr Glu Ile
 1               5                  10                  15

Leu His Leu Pro Asn Leu Thr Glu Glu Gln Arg Asn Lys Phe Ile Gln
                20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys Ala Asp Asn Lys Phe Asn
 50                  55                  60

Lys Glu Gln Gln Asn Ala Phe Tyr Glu Ile Leu His Leu Pro Asn Leu
 65                  70                  75                  80

Thr Glu Glu Gln Arg Asn Lys Phe Ile Gln Ser Leu Lys Asp Asp Pro
                 85                  90                  95

Ser Val Ser Lys Glu Ile Leu Ala Glu Ala Lys Lys Leu Asn Asp Ala
            100                 105                 110

Gln Ala Pro Lys Ala Asp Asn Lys Phe Asn Lys Glu Gln Gln Asn Ala
        115                 120                 125

Phe Tyr Glu Ile Leu His Leu Pro Asn Leu Thr Glu Glu Gln Arg Asn
```

```
              130                 135                 140
Lys Phe Ile Gln Ser Leu Lys Asp Asp Pro Ser Val Ser Lys Glu Ile
145                 150                 155                 160

Leu Ala Glu Ala Lys Lys Leu Asn Asp Ala Gln Ala Pro Lys Ala Asp
                165                 170                 175

Asn Lys Phe Asn Lys Glu Gln Gln Asn Ala Phe Tyr Glu Ile Leu His
            180                 185                 190

Leu Pro Asn Leu Thr Glu Glu Gln Arg Asn Lys Phe Ile Gln Ser Leu
        195                 200                 205

Lys Asp Asp Pro Ser Val Ser Lys Glu Ile Leu Ala Glu Ala Lys Lys
    210                 215                 220

Leu Asn Asp Ala Gln Ala Pro Lys Ala Asp Asn Lys Phe Asn Lys Glu
225                 230                 235                 240

Gln Gln Asn Ala Phe Tyr Glu Ile Leu His Leu Pro Asn Leu Thr Glu
                245                 250                 255

Glu Gln Arg Asn Lys Phe Ile Gln Ser Leu Lys Asp Asp Pro Ser Val
            260                 265                 270

Ser Lys Glu Ile Leu Ala Glu Ala Lys Lys Leu Asn Asp Ala Gln Ala
        275                 280                 285

Pro Lys
    290

<210> SEQ ID NO 96
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys Ala Asp Asn Lys Phe Asn
    50                  55                  60

Lys Glu Gln Gln Asn Ala Phe Tyr Glu Ile Leu His Leu Pro Asn Leu
65                  70                  75                  80

Thr Glu Glu Gln Arg Asn Gly Phe Ile Gln Ser Leu Lys Asp Asp Pro
                85                  90                  95

Ser Val Ser Lys Glu Ile Leu Ala Glu Ala Lys Lys Leu Asn Asp Ala
            100                 105                 110

Gln Ala Pro Lys Ala Asp Asn Lys Phe Asn Lys Glu Gln Gln Asn Ala
        115                 120                 125

Phe Tyr Glu Ile Leu His Leu Pro Asn Leu Thr Glu Glu Gln Arg Asn
    130                 135                 140

Gly Phe Ile Gln Ser Leu Lys Asp Asp Pro Ser Val Ser Lys Glu Ile
145                 150                 155                 160

Leu Ala Glu Ala Lys Lys Leu Asn Asp Ala Gln Ala Pro Lys Ala Asp
                165                 170                 175

Asn Lys Phe Asn Lys Glu Gln Gln Asn Ala Phe Tyr Glu Ile Leu His
            180                 185                 190
```

```
Leu Pro Asn Leu Thr Glu Glu Gln Arg Asn Gly Phe Ile Gln Ser Leu
        195                 200                 205

Lys Asp Asp Pro Ser Val Ser Lys Glu Ile Leu Ala Glu Ala Lys Lys
    210                 215                 220

Leu Asn Asp Ala Gln Ala Pro Lys Ala Asp Asn Lys Phe Asn Lys Glu
225                 230                 235                 240

Gln Gln Asn Ala Phe Tyr Glu Ile Leu His Leu Pro Asn Leu Thr Glu
                245                 250                 255

Glu Gln Arg Asn Gly Phe Ile Gln Ser Leu Lys Asp Asp Pro Ser Val
            260                 265                 270

Ser Lys Glu Ile Leu Ala Glu Ala Lys Lys Leu Asn Asp Ala Gln Ala
        275                 280                 285

Pro Lys
    290

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 97

His His His His His His
1               5
```